United States Patent [19]

Hanna et al.

[11] Patent Number: 5,766,510
[45] Date of Patent: Jun. 16, 1998

[54] LIQUID CRYSTALLINE COMPOUND AND USE THEREOF

[75] Inventors: Junichi Hanna; Masahiro Funahashi; Masanori Akada; Masayuki Ando; Yozo Kosaka, all of Tokyo-To, Japan

[73] Assignee: Dai Nippon Printing Co., Ltd., Japan

[21] Appl. No.: 701,436

[22] Filed: Aug. 22, 1996

[30] Foreign Application Priority Data

| Aug. 25, 1995 | [JP] | Japan | 7-239037 |
| Aug. 25, 1995 | [JP] | Japan | 7-239038 |
| Mar. 25, 1996 | [JP] | Japan | 8-093044 |
| Mar. 25, 1996 | [JP] | Japan | 8-093045 |

[51] Int. Cl.$^6$ .................. C09K 19/32; C07D 277/62; C07D 513/02
[52] U.S. Cl. .................. 252/299.62; 548/148; 548/151; 548/152; 548/178; 548/179
[58] Field of Search .................. 252/299.01, 299.61, 252/299.62; 428/1; 548/148, 151, 152, 178, 179

[56] References Cited

U.S. PATENT DOCUMENTS

| 5,262,083 | 11/1993 | Mori et al. | 252/299.61 |
| 5,268,123 | 12/1993 | Mori et al. | 252/299.61 |
| 5,305,131 | 4/1994 | Terada et al. | 359/104 |

*Primary Examiner*—Shean C. Wu
*Attorney, Agent, or Firm*—Parkhurst & Wendel, L.L.P.

[57] ABSTRACT

A process for producing a liquid crystalline compound represented by the following general formula (A):

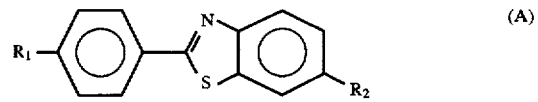

4 Claims, 2 Drawing Sheets 5,766,510

1
LIQUID CRYSTALLINE COMPOUND AND USE THEREOF

BACKGROUND OF THE INVENTION

The present invention relates to a liquid crystalline compound and use thereof. More particularly, the present invention relates to a process for producing a novel liquid crystalline compound, which exhibits liquid crystallinity and, in addition, photoconductivity and fluorescence, and use of the liquid crystalline compound in a liquid crystalline charge transport material.

Liquid crystalline compounds having various structures are known in the art and have been extensively used as a liquid crystal display material.

Materials, wherein a charge transport molecule which serves as a charge transport site are dissolved or dispersed in a matrix material, such as a polycarbonate resin, or materials, wherein a charge transport molecule structure pends as a pendant on a polymer backbone, such as polyvinyl carbazole, are known in the art. These materials have been extensively used as materials for photoconductors in copying machines, printers and the like.

For the above conventional charge transport materials, in the case of dispersive charge transport materials, that the charge transport molecule has high solubility in the polymer as a matrix is preferred from the viewpoint of improving the charge transport capability. In fact, however, bringing the charge transport molecule to a high concentration in the matrix leads to crystallization of the charge transport molecule in the matrix, and, for this reason, the upper limit of the concentration of the charge transport molecule is generally 20 to 50% by weight although it varies depending upon the kind of the charge transport molecule. This means that the matrix not having charge transport capability occupies not less than 50% by weight of the whole material. This in turn raises a new problem that the charge transport capability and response speed of a film formed from the material are limited by the excess matrix present in the material.

On the other hand, in the case of the pendant type charge transport polymer, the proportion of the pendant having charge transport capability can be increased. This polymer, however, involves many practical problems associated with mechanical strength, environmental stability and durability of the formed film, film-forming properties and the like. In this type of charge transport material, the charge transport pendants are locally located in close proximity, and the local proximity portion serves as a stable site in hopping of charges and functions as a kind of trap, unfavorably resulting in lowered charge mobility.

For all the above charge transport materials, electrical properties of such amorphous materials raise a problem that, unlike crystalline materials, the hopping site fluctuates in terms of space, as well as in terms of energy. For this reason, the charge transport depends greatly upon the concentration of the charge transport site, and the mobility is generally about $10^{-6}$ to $10^{-5}$ cm$^2$/vs which is much smaller than that of the molecular crystal, 0.1 to 1 cm$^2$/vs. Further, the amorphous materials have an additional problem that the charge transport properties depend greatly upon temperature and field strength. This is greatly different from the crystalline charge transport materials.

A polycrystalline charge transport material is a promissing material in applications where a charge transport layer having a large area is necessary, because it can form an even 2
charge transport film having a large area can be evenly formed. The polycrystalline material, however, is inherently an uneven material from the microscopic viewpoint and involves a problem that a defect formed in the interface of particles should be inhibited.

Accordingly, the present invention aims to solve the above problems of the prior art and to provide a novel charge transport material which simultaneously realizes advantages of the amorphous materials, that is, structural flexibility and evenness in a large area, and advantages of the crystalline materials having molecular orientation and is excellent in high-quality charge transport capability, thin film-forming properties, various types of durability and the like.

DISCLOSURE OF INVENTION

An object of the present invention is to provide a novel liquid crystalline compound which exhibits liquid crystallinity and, in addition, photoconductivity and fluorescence and a process for producing the same.

Another object of the present invention is to provide a novel charge transport material which simultaneously realizes advantages of the amorphous materials, that is, structural flexibility and evenness in a large area, and advantages of the crystalline materials having molecular orientation and is excellent in high-quality charge transport capability, thin film-forming properties, various types of durability and the like.

According to one aspect of the present invention, there is provided a process for producing a liquid crystalline compound represented by the general formula (A) described below, comprising the steps of: reacting a compound represented by the general formula (1), described below, with a compound represented by the general formula (2) described below, brominating the reaction product to give a compound represented by the general formula (3) described below; and substituting the bromine atom with an $R_2$ group.

According to another aspect of the present invention, there is provided a process for producing a liquid crystalline compound represented by the general formula (B) described below, comprising the step of: reacting a compound represented by the general formula (4), described below, with a compound represented by the general formula (5) described below.

According to a further aspect of the present invention, there is provided a process for producing a liquid crystalline compound represented by the general formula (C) described below, comprising the step of: reacting two moles of a compound represented by the general formula (6), described below, with one mole of a compound represented by the general formula (7) described below.

According to a yet further aspect of the present invention, there is provided a process for producing a liquid crystalline compound represented by the general formula (D) described below, comprising the step of: reacting two moles of a compound represented by the general formula (8), described below, with one mole of a compound represented by the general formula (9) described below.

According to a yet further aspect of the present invention, there is provided a liquid crystalline charge transport material which exhibits smectic liquid crystallinity and has a reduction potential relative to a standard reference electrode (SCE) in the range of from −0.3 to −0.6 (Vvs. SEC).

According to a yet further aspect of the present invention, there is provided a liquid crystalline charge transport material which exhibits smectic liquid crystallinity and has an

BEST MODE FOR CARRYING OUT THE INVENTION

Process for producing liquid crystalline compound

Figure 1:
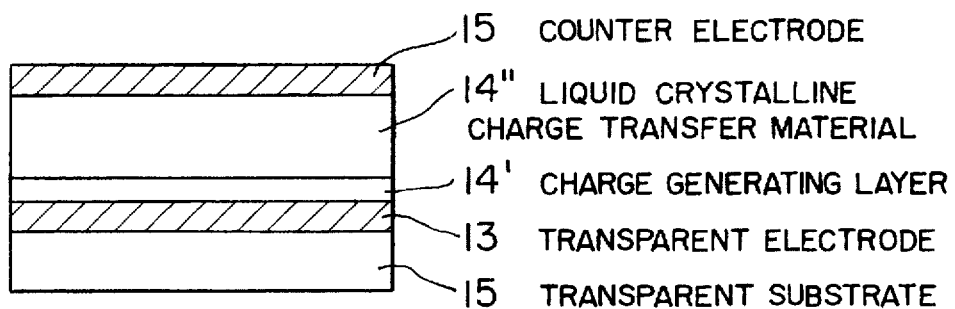
FIGS. 1, 2, 3 and 4 are cross-sectional views of embodiments where the crystalline charge transport material according to the present invention has been applied to a charge transport layer in an image recording device.

The first invention relates to a process for producing a liquid crystalline compound represented by the general formula (A), comprising the steps of: reacting a compound represented by the general formula (1) with a compound represented by the general formula (2); brominating the reaction product to give a compound represented by the general formula (3); and substituting the bromine atom of the compound (3) with an $R_2$ group:

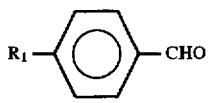
(1)

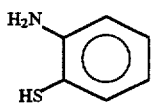
(2)

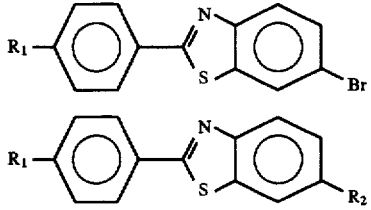
(3)

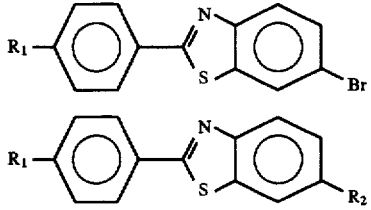
(A)

wherein $R_1$ and $R_2$ represent (a) a cyano group, (b) a nitro group, (c) a fluorine atom, or (d) a $C_1$–$C_{22}$ straight-chain or branched, saturated or unsaturated, alkyl or alkoxy group attached to the aromatic ring through an oxygen atom, or a sulfur atom, provided that at least one of $R_1$ and $R_2$ represents said alkyl or alkoxy group.

The second invention relates to a process for producing a liquid crystalline compound represented by the general formula (B), comprising the step of: reacting a compound represented by the general formula (4) with a compound represented by the general formula (5):

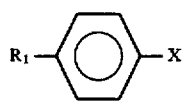
(4)

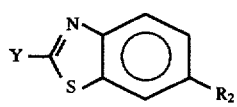
(5)

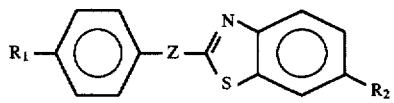
(B)

wherein $R_1$ and $R_2$ represent a $C_1$–$C_{22}$ straight-chain or branched saturated or unsaturated alkyl or alkoxy group attached to the aromatic ring through a cyano group, a nitro group, a fluorine atom, an oxygen atom, or a sulfur atom, provided that at least one of $R_1$ and $R_2$ represents said alkyl or alkoxy group; and X and Y are respectively groups which are reacted with each other to form a —COO—, —OCO—, —N═N—, —CH═N—, —N═N—, —CH$_2$S—, —CH═CH—, or acetylene group.

The third invention relates to a process for producing a liquid crystalline compound represented by the general formula (C), comprising the step of: reacting 2 moles of a compound represented by the general formula (6) with one mole of a compound represented by the general formula (7):

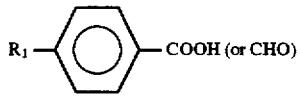
(6)

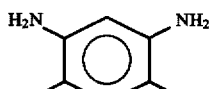
(7)

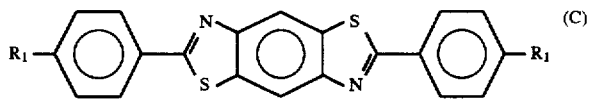
(C)

wherein $R_1$ is a $C_1$–$C_{22}$ straight-chain or branched saturated or unsaturated alkyl or alkoxy group attached to the aromatic ring through an oxygen or sulfur atom.

The fourth invention relates to a process for producing a liquid crystalline compound represented by the general formula (D), comprising the step of: reacting two moles of a compound represented by the general formula (8) with one mole of a compound represented by the general formula (9):

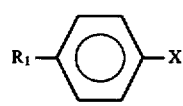
(8)

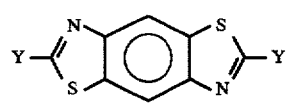
(9)

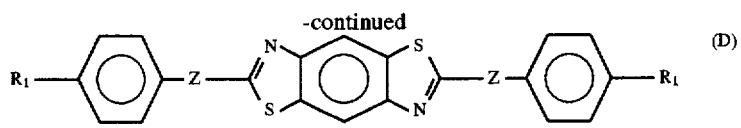

wherein $R_1$ is a $C_1$–$C_{22}$ straight-chain or branched saturated or unsaturated alkyl or alkoxy group attached to the aromatic ring through an oxygen or sulfur atom; and X and Y are respectively groups which are reacted with each other to form a —COO—, —OCO—, —N=N—, —CH=N—, —N=N—, —CH$_2$S—, —CH=CH—, or acetylene group.

According to a specific one embodiment of the present invention, there is provided a process for producing a liquid crystalline compound represented by the following general formula (I), comprising the steps of: reacting a 4-alkoxybenzaldehyde with o-aminobenzenethiol to synthesize a 2-(4'-alkoxyphenyl)benzothiazole; brominating the 2-(4'-alkoxyphenyl)benzothiazole to synthesize a 2-(4'-alkoxyphenyl)-6-bromobenzothiazole; and reacting the resultant bromide with an alkanethiol:

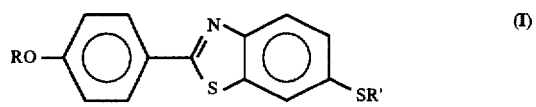

wherein R represents a $C_4$–$C_{20}$ alkyl group; and R' represents a $C_4$–$C_{20}$ alkyl group, provided that the total number of carbon atoms contained in R and R' is 10 or more.

A further preferred embodiment of the production process will be described.

According to the present invention, a 4-alkoxybenzaldehyde is reacted with 1 mole or more, preferably 1.1 to 1.5 moles or more, based on one mole of the 4-alkoxybenzaldehyde, of o-aminobenzenethiol in a solvent suitable for a dehydration reaction (oxidative cyclization), preferably dimethylsulfoxide, at a temperature of 100° C. or above, preferably 120° to 160° C., for about 30 min to 2 hr.

In this reaction, the aldehyde group, the amino group, and the thiol group are combined together to form a thiazole ring, thus giving a 2-(4'-alkoxyphenyl)benzothiazole as an intermediate. This reaction can be easily achieved, and the intermediate is produced in a high yield of not less than 90%. The intermediate may be purified before use in the subsequent step or alternatively used in the subsequent step without purification.

The 2-(4'-alkoxyphenyl)benzothiazole is then brominated. In the bromination, the 2-(4'-alkoxyphenyl)benzothiazole is dissolved in a suitable solvent, such as glacial acetic acid, and bromine in an equimolar or slightly excessive molar amount is dropwise added thereto. In this reaction, bromine is easily substituted in the 6-position of the benzothiazole ring to give a 2-(4'-alkoxyphenyl)-6-bromobenzothiazole, and the reaction under mild conditions with heating can give the bromide in a yield of not less than 60%. When this intermediate contains a dibromination product and/or a substance remaining unreacted as impurities, it is preferably purified by recrystallization before use in the subsequent step.

Finally, the above bromide is reacted with an alkanethiol to give a liquid crystalline compound according to the present invention. Since this reaction is an aromatic nucleophilic displacement reaction by taking advantage of a thiolate anion, it is preferably performed in an alkaline atmosphere. For example, a liquid crystalline compound represented by the general formula (I) is produced by suspending an oil dispersion of sodium hydride in an ether, dropwise adding a corresponding alkanethiol to the suspension to produce a sodium salt of the alkanethiol, and reacting the sodium salt with the above bromide in a suitable solvent at a temperature of about 30° to 100° C. for 30 min to 2 hr.

According to the process of the present invention, the number of carbon atoms of the alkyl group in the 4-alkoxybenzaldehyde and the alkanethiol is important, and the number of carbon atoms of the alkyl group is preferably not less than 4, preferably 4 to 20 from the viewpoint of developing excellent liquid crystallinity. For the alkanethiol, the number of carbon atoms of the alkyl group is 4 or more, preferably 4 to 20. These alkyl groups may be somewhat branched. However, in order to develop excellent liquid crystallinity, the alkyl group is more preferably linear with the total number of carbon atoms of R and R' being 10 or more, preferably 12 to 40.

Further, liquid crystalline compounds represented by the following general formula (II) also fall within the scope of the present invention:

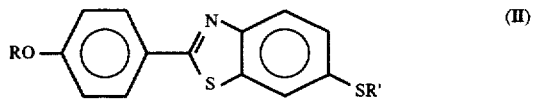

wherein R represents $C_7H_{15}$ and R' represents $C_6H_{13}$, $C_8H_{17}$, $C_{10}H_{21}$ or $C_{12}H_{25}$.

The above liquid crystalline compounds according to the present invention can be produced in a high yield from a p-alkoxybenzaldehyde, for example, by the following reaction scheme:

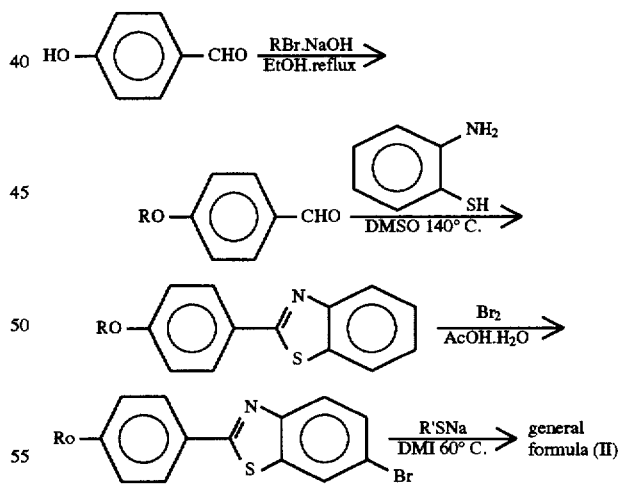

wherein R and R' are as defined above and DMI represents N,N'-dimethylimidazolidinone.

The present invention provides a novel liquid crystalline compound which exhibits liquid crystallinity and, in addition, photoconductivity and fluorescence. The novel liquid crystalline compound is useful as a material for a liquid crystal display, a photosensitive material for electrophotography and the like. In particular, the liquid crystalline compound of the present invention has strong fluorescence and, hence, when used as a material for a color liquid crystal display or used in combination with a dichroic dye, can effectively utilize an ultraviolet portion in a backlight source, offering a display image having excellent sharpness and brightness.

Liquid crystalline charge transport material

According to a further aspect of the present invention, there is provided a liquid crystalline charge transport material which exhibits smectic liquid crystallinity and has a reduction potential relative to a standard reference electrode (SCE) in the range of from −0.3 to −0.6 (Vvs. SEC). According to a further aspect of the present invention, there is provided a liquid crystalline charge transport material which exhibits smectic liquid crystallinity and has an oxidation potential relative to a standard reference electrode (SCE) in the range of from 0.2 to 1.3 (Vvs. SEC).

A liquid crystalline molecule, by virtue of its molecular structure, has self-orientation, and, in the case of charge transport utilizing this molecule as a hopping site, unlike the above molecule dispersive material, the spacial and energy scattering of the hopping site is inhibited, enabling a band-like transport property such as found in a molecular crystal to be realized. This enables a mobility of about $10^{-3}$ to $10^{-2}$ cm$^2$/vs, that is, a larger mobility than that in the conventional molecular dispersive material, to be realized, and, in addition, the charge transport properties do not depend upon electric field.

In order that the material serves as a hole transport material, the molecule should have a low ionization potential, and, hence, the oxidation potential should be in the range of from 0.2 to 1.3 (Vvs. SEC) relative to a standard reference electrode (SCE). Further, in order that the material serves as an electron transport material, the molecule should have high electron affinity, and, hence, the reduction potential should be in the range of from −0.3 to −0.6 (Vvs.SEC). The above requirements are the same as the well known requirements for a charge transport molecule used in the conventional molecule dispersive material.

Preferred liquid crystalline charge transport materials of the present invention will be listed in Tables 1 to 71. Among the charge transport materials listed in these tables, more preferred materials are those which satisfy the above requirements, have (aromatic ring of 6 π electron system) n (wherein n is an integer of 1 to 4) cores and exhibit smectic liquid crystallinity, those wherein the aromatic ring of 6 π a electron system is linked through a carbon-carbon double bond or a carbon-carbon triple bond, and those which has a core of a benzothiazole ring, a benzoxazole ring, a benzimidazole ring, a naphthalene ring, or other aromatic ring of 10 π electron system and exhibit smectic liquid crystallinity.

The liquid crystalline charge transport materials according to the present invention are useful for various applications such as photosensors, electroluminescence devices, photoconductors, space modulating devices, and thin film transistors.

The liquid crystalline charge transfer materials according to the present invention can realize high-speed mobility and inhibition of the creation of structural traps. Therefore, high-speed response photosensors may be mentioned as the first application thereof. Next, by virtue of excellent charge transport properties, the liquid crystalline charge transfer materials according to the present invention can be used as a charge transfer layer in electroluminescence devices. Further, since electric field orientation and photoconductivity can be simultaneously switched, they can be used in image display devices.

The application to image display devices will be described as a representative example. In an image display device, when a device comprising a transparent substrate, such as glass, a transparent electrode, such as ITO (indium-tin-oxide), a charge generating layer capable of generating carriers according to exposure, the liquid crystalline charge transport material of the present invention, and a counter electrode (such as a gold electrode) laminated in that order is subjected to imagewise exposure (input image) through the bottom of the device as shown in the schematic diagram, the liquid crystalline charge transport material is aligned according to the exposure, resulting in flow of carriers in the counter electrode (gold electrode). The input image can be reproduced by optical reading of the alignment of the liquid crystal. The larger the smectic properties of the liquid crystal, the longer the storage time of the alignment of the liquid crystal and the longer the storage time of the input information.

Figure 2:
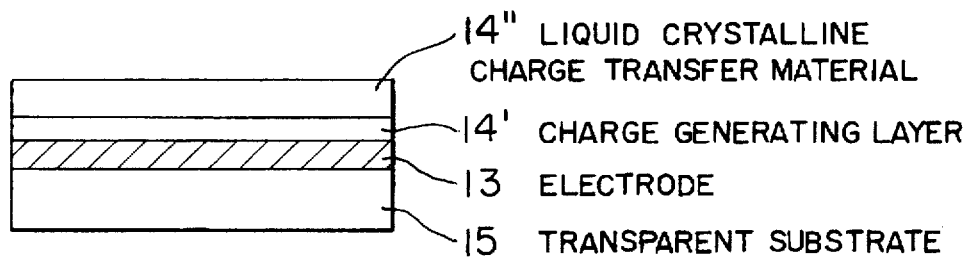
Figure 3:
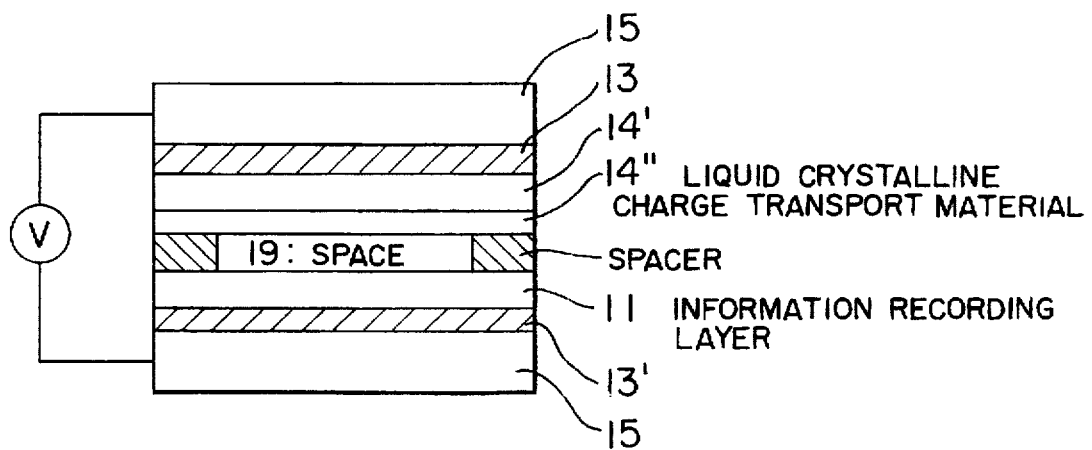

FIGS. 1 to 3 are explanatory diagrams of embodiments where the liquid crystalline charge transport material according to the present invention has been applied to a charge transport layer in an image recording device. FIG. 1 is a schematic view of a photosensor, an embodiment where the liquid crystalline charge transport material according to the present invention has been applied to a charge transport layer. Use of the photosensor will be described in more detail. As shown in FIG. 3, the device is subjected to pattern exposure from the direction of the above in the drawing while applying a voltage across the upper and lower electrodes 15. Carriers are generated in a pattern form in 14', and charges transported by a charge transport layer 14" are discharged in a space 19 and reach the surface of an information recording layer 11.

The information recording layer is, for example, a liquid crystal/polymer composite layer formed of a composite of a smectic liquid crystal and a polymer. The liquid crystal is aligned in a pattern form in an electric field of accumulated charges and accumulated, enabling optical recording to be performed.

Figure 4:
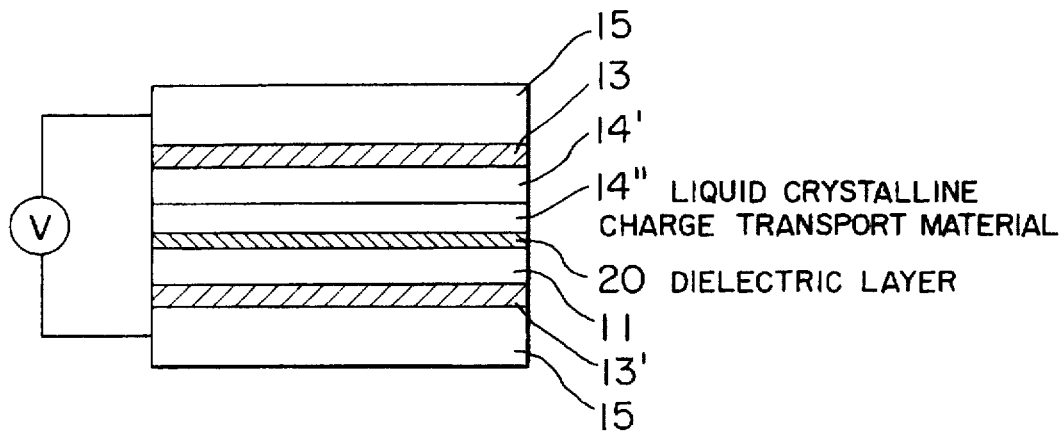

In the embodiment shown in FIG. 4, exposure with a voltage being applied may be carried out in the same manner as described above in connection with the embodiment shown in FIG. 3. The generated charges (image) are accumulated on the top surface of a dielectric layer 20, and the liquid crystal is aligned in a pattern form in an electric field of charges accumulated in the same manner as described above in connection with the embodiment shown in FIG. 3 and accumulated, enabling optical reading to be performed.

Figure 5:
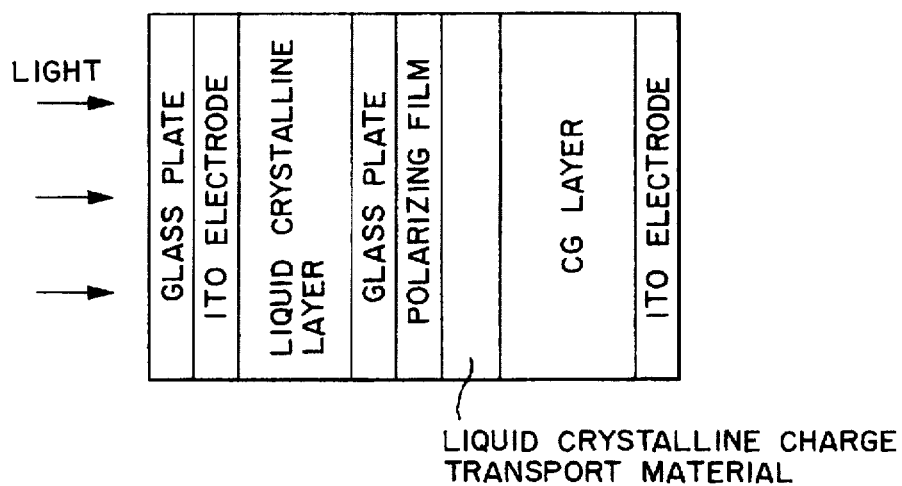
FIG. 5 is a cross-sectional view of an embodiment where the liquid crystalline charge transport material has been applied to a space light modulating device.
Figure 6:
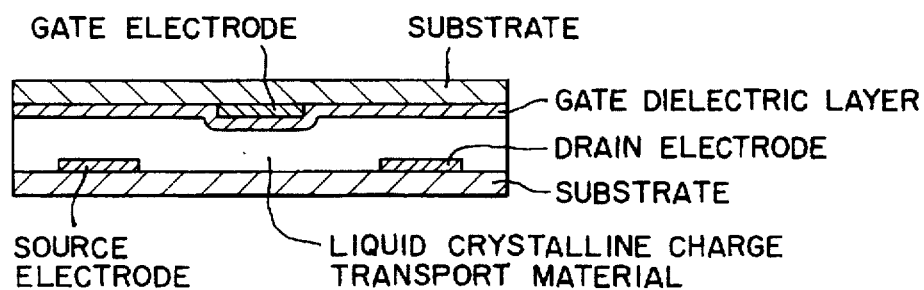
FIG. 6 is a cross-sectional view of an embodiment where the liquid crystalline charge transport material according to the present invention has been applied to a thin film transistor.

Further, the liquid crystalline charge transport material according to the present invention can be used also in a pace optical light modulating device schematically shown in FIG. 5. Furthermore, the liquid crystalline charge transport materials of the present invention can also be used as an active layer of a thin film transistor. For example, as shown in FIG. 6, the liquid crystalline material may be disposed on a substrate having thereon source, drain, and gate electrodes.

Thus, the liquid crystalline charge transport materials according to the present invention are useful for various applications such as photosensors, electroluminescence devices, photoconductors, space modulating devices, and thin film transistors.

TABLE 1

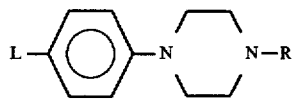

| No | L | R | Cr | LC |
|---|---|---|---|---|
| 7109 | O$_2$N— | —CO—C$_{10}$H$_{20}$—Si$_4$O$_4$Me$_7$-cy | K? | A58 I |
| 7122 | NC—CH=CH— | —C$_4$H$_9$ | K61.1 | A57.7 N113.8 I |
| 7123 | NC—CH=CH— | —C$_5$H$_{11}$ | K61.8 | A93.3 N122.2 I |
| 7124 | NC—CH=CH— | —C$_6$H$_{13}$ | K79.7 | A113 N120.6 I |
| 7125 | NC—CH=CH— | —C$_7$H$_{15}$ | K70.2 | A125 I |
| 7126 | NC—CH=CH— | —C$_8$H$_{17}$ | K59.3 | A127.4 I |
| 7127 | NC—CH=CH— | —C$_9$H$_{19}$ | K55 | A131 I |
| 7130 | C$_5$H$_{13}$— | —C$_9$H$_{19}$ | K42.5 | B65.5 I |
| 7131 | C$_7$H$_{16}$— | —C$_7$H$_{15}$ | K52.5 | B68 I |
| 7132 | C$_2$H$_5$—OOC—CH=CH— | —C$_4$H$_9$ | K96.3 | S104 S153.9 I |
| 7133 | C$_2$H$_5$—OOC—CH=CH— | —C$_5$H$_{11}$ | K88.8 | S88.5 S149.1 I |
| 7134 | C$_2$H$_5$—OOC—CH=CH— | —C$_6$H$_{13}$ | K74.2 | S81 S146.2 I |
| 7135 | C$_2$H$_5$—OOC—CH=CH— | —C$_7$H$_{15}$ | K61 | S74 S142.5 I |
| 7136 | C$_2$H$_5$—OOC—CH=CH— | —C$_8$H$_{17}$ | K62 | S75 S143 I |
| 7137 | C$_2$H$_5$—OOC—CH=CH— | —C$_9$H$_{19}$ | K60 | S73 S141.4 I |
| 7138 | CH$_3$—O— | —C$_3$H$_7$ | K51.9 | S27.9 A33.6 I |
| 7139 | CH$_3$—O— | —C$_4$H$_9$ | K38.7 | S26.2 A36.7 I |
| 7140 | CH$_3$—O— | —C$_5$H$_{11}$ | K38 | S23.5 A31.2 I |
| 7141 | CH$_3$—O— | —C$_6$H$_{13}$ | K31.6 | S14 A28.7 I |
| 7142 | CH$_3$—O— | —C$_7$H$_{15}$ | K36.1 | S23.8 A27.7 N33.6 I |
| 7148 | C$_2$H$_5$—O— | —C$_4$H$_9$ | K49.3 | A67.1 I |
| 7149 | C$_4$H$_9$—O— | —C$_4$H$_9$ | K7.4 | S76 A96.2 I |
| 7150 | C$_4$H$_9$—O— | —C$_5$H$_{11}$ | K11.3 | S53.4 I |
| 7151 | C$_4$H$_9$—O— | —C$_6$H$_{13}$ | K20.8 | S54.5 A83.4 I |
| 7152 | C$_5$H$_{11}$—O— | —C$_3$H$_7$ | K36.5 | S74 S76.5 I |
| 7153 | C$_5$H$_{11}$—O— | —C$_4$H$_9$ | K59.5 | S61.5 S81.2 I |
| 7154 | C$_5$H$_{11}$—O— | —C$_5$H$_{11}$ | K39.5 | S54 S84.8 I |
| 7155 | C$_5$H$_{11}$—O— | —C$_6$H$_{13}$ | K40.5 | S46.5 S85.5 I |

TABLE 2

| No | L | R | Cr | LC |
|---|---|---|---|---|
| 7156 | C$_5$H$_{11}$—O— | —C$_7$H$_{15}$ | K35.4 | S84.8 I |
| 7157 | C$_5$H$_{11}$—O— | —C$_8$H$_{17}$ | K39.5 | S84 I |
| 7158 | C$_5$H$_{11}$—O— | —C$_9$H$_{19}$ | K42.5 | S82.5 I |
| 7159 | C$_6$H$_{13}$—O— | —C$_4$H$_9$ | K18.2 | S43.4 A74.1 I |
| 7160 | C$_6$H$_{13}$—O— | —C$_9$H$_{19}$ | K35 | B87 I |
| 7161 | C$_7$H$_{15}$—O— | —C$_3$H$_7$ | K47 | B72 I |
| 7162 | C$_7$H$_{15}$—O— | —C$_7$H$_{15}$ | K53.5 | B85.5 I |
| 7163 | C$_5$H$_{11}$—CO— | —C$_5$H$_{11}$ | K75.5 | S104.5 I |
| 7164 | C$_5$H$_{11}$—CO— | —C$_6$H$_{13}$ | K80.5 | S102 S103 I |
| 7165 | C$_5$H$_{11}$—CO— | —C$_7$H$_{15}$ | K71 | S95 S101 I |
| 7166 | C$_5$H$_{11}$—CO— | —C$_8$H$_{17}$ | K87 | S95.3 S98 I |
| 7167 | C$_5$H$_{11}$—CO— | —C$_9$H$_{19}$ | K84.5 | S93.8 S99.6 I |
| 7168 | C$_6$H$_{13}$—CO— | —C$_8$H$_{17}$ | K72 | S101.8 S105.8 I |
| 7169 | C$_7$H$_{15}$—CO— | —C$_8$H$_{17}$ | K86.6 | S97 S104.5 I |

TABLE 3

| No | L | R | Cr | LC |
|---|---|---|---|---|
| 26206 | C$_3$H$_7$— | —C$_3$H$_7$ | K90 | P120 P190 I |
| 26207 | C$_4$H$_9$— | —C$_4$H$_9$ | K57 | P119 P190 I |
| 26208 | C$_5$H$_{11}$— | —C$_5$H$_{11}$ | K41 | P114 P190 I |
| 26209 | C$_6$H$_{13}$— | —C$_6$H$_{13}$ | K55 | P184 I |
| 26210 | C$_7$H$_{15}$— | —C$_7$H$_{15}$ | K28 | P180 I |

TABLE 3-continued

| No | L | R | Cr | LC |
|---|---|---|---|---|
| 26211 | C$_8$H$_{17}$— | —C$_8$H$_{17}$ | K39 | P173 I |
| 26212 | C$_9$H$_{19}$— | —C$_9$H$_{19}$ | K45 | P165 I |
| 26213 | C$_{10}$H$_{21}$— | —C$_{10}$H$_{21}$ | K62 | P160 I |
| 26217 | C$_2$H$_5$— | —O—C$_2$H$_5$ | K166 | S182 I |
| 26221 | C$_3$H$_7$—O— | —O—C$_3$H$_7$ | K210 | P215 I |
| 26222 | C$_4$H$_9$—O— | —O—C$_4$H$_9$ | K197 | P227 I |
| 26223 | C$_5$H$_{11}$—O— | —O—C$_5$H$_{11}$ | K185 | P218 I |
| 26224 | C$_6$H$_{13}$—O— | —O—C$_6$H$_{13}$ | K172 | P218 I |
| 26225 | C$_7$H$_{15}$—O— | —O—C$_7$H$_{15}$ | K166 | P209 I |
| 26226 | C$_8$H$_{17}$—O— | —O—C$_8$H$_{17}$ | K163 | P203 I |
| 26227 | C$_9$H$_{19}$—O— | —O—C$_9$H$_{19}$ | K162 | P194 I |
| 26228 | C$_{10}$H$_{21}$—O— | —O—C$_{10}$H$_{24}$ | K161 | P189 I |
| 26230 | CH$_3$—O— | —OOC—C$_2$H$_5$ | K148 | S155 N193 I |

| No | L | R | Cr | LC |
|---|---|---|---|---|
| 28692 | C$_3$H$_7$— | —C$_3$H$_7$ | K163.3 | B171.5 I |
| 28693 | C$_4$H$_9$— | —C$_4$H$_9$ | K36.3 | E106.9 S113.4 B179.5 I |
| 28694 | C$_5$H$_{11}$— | —C$_5$H$_{11}$ | K50 | B155.9 U |
| 28695 | C$_6$H$_{13}$— | —C$_6$H$_{13}$ | K30 | E76.7 S107.9 B182.8 I |
| 28696 | C$_7$H$_{15}$— | —C$_7$H$_{15}$ | K27.7 | E82 S100.4 B175.5 I |
| 28697 | C$_8$H$_{17}$— | —C$_8$H$_{17}$ | K58.1 | E64.5 S93.4 B178.3 I |
| 28698 | C$_9$H$_{19}$— | —C$_9$H$_{19}$ | K52.6 | E75.3 S87.3 B174.1 I |

TABLE 4

| No | L | R | Cr | LC |
|---|---|---|---|---|
| 22075 | $C_6H_{13}$—CHMe—OOC— | —O—$C_{10}H_{21}$ 1 | K? | A? I |
| 22076 | $C_2H_5$—CHMe—$CH_2$—OOC— | —O—$C_{10}H_{21}$ 1 | K22 | A48 I |
| 22077 | $C_6H_{13}$—$CHCF_3$—OOC— | —O—$C_{10}H_{21}$ 1 | K-13 | A-6 I |

| No | L | R | Cr | LC |
|---|---|---|---|---|
| 8085 | $C_8H_{17}$—O— | —$C_5H_{11}$ | K36 | C44.5 A75 N83.5 I |

TABLE 5

| No | L | R | Cr | LC |
|---|---|---|---|---|
| 22305 | $C_7H_{15}$— | —$C_7H_{15}$ | K83.1 | C58 N109.5 I |
| 22307 | $C_6H_{13}$—O— | —$C_5H_{11}$ | K81 | A85 N120 I |
| 22309 | $C_8H_{17}$—O— | —$C_7H_{15}$ | K73 | A106.1 N111.3 I |
| 22317 | $C_7H_{15}$— | —O—$C_7H_{15}$ | K83.1 | C58 N109.5 I |
| 22318 | $C_8H_{17}$— | —O—$C_6H_{13}$ | K70 | C73 N109 I |
| 22320 | $C_6H_{13}$—O— | —O—$C_7H_{15}$ | K82 | C88.4 N133.4 I |
| 22321 | $C_6H_{13}$—O— | —O—$C_8H_{17}$ | K85.1 | C89.1 N133.3 I |
| 22322 | $C_7H_{15}$—O— | —O—$C_7H_{15}$ | K88.9 | C94.7 A105.5 N129.8 I |
| 22323 | $C_7H_{15}$—O— | —O—$C_8H_{17}$ | K82.5 | C103.8 A110.7 N132.2 I |
| 22324 | $C_7H_{15}$—O— | —O—$C_9H_{19}$ | K90.4 | C103 A113.8 N128 I |
| 22325 | $C_8H_{17}$—O— | —O—$C_7H_{15}$ | K84.7 | C93.8 A115.7 N129.7 I |
| 22326 | $C_8H_{17}$—O— | —O—$C_8H_{17}$ | K85.5 | C101.8 A119.8 N131 I |
| 22327 | $C_8H_{17}$—O— | —O—$C_9H_{19}$ | K90 | C104.2 A122.4 N131.8 I |

TABLE 6

| No | L | R | Cr | LC |
|---|---|---|---|---|
| 22328 | $C_9H_{19}$—O— | —O—$C_8H_{17}$ | K87 | C106.3 A122.5 N129.8 I |
| 22329 | $C_9H_{19}$—O— | —O—$C_9H_{19}$ | K89.4 | C115.5 A125.7 N128.4 I |

TABLE 6-continued

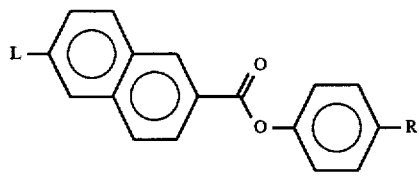

| No | L | R | | Cr | LC |
|---|---|---|---|---|---|
| 22333 | $C_4H_9-$ | $-CO-C_4H_9$ | | K116 | S120 N130 I |
| 22334 | $C_{10}H_{21}-O-$ | $-COO-CH(C_3H_6-/-C_2H_5)_2$ | R | K<30 | A25 I |
| 22337 | $C_8H_{17}-O-$ | $-COO-CHMe-C_6H_{13}$ | R | K69.3 | A62.1 I |
| 22338 | $C_{10}H_{21}-O-$ | $-COO-CHMe-C_6H_{13}$ | R | K60 | A20 U |
| 22341 | $C_{10}H_{21}-O-$ | $-COO-CH_2-CHMe-C_2H_5$ | 1 | K85.2 | A103.6 I |
| 22342 | $C_9H_{19}-O-$ | $-CH=CH-COO-CHCF_3-C_6H_{13}$ | R | K51 | CA63 A69 I |
| 22343 | $C_{10}H_{21}-O-$ | $-CH=CH-COO-CHCF_3-C_6H_{13}$ | R | K50 | CA56 A66 I |
| 22344 | $C_{11}H_{23}-O-$ | $-CH=CH-COO-CHCF_3-C_6H_{13}$ | R | K45 | CA52 A61 I |
| 22345 | $C_{10}H_{21}-O-$ | $-COO-CHCF_3-C_6H_{13}$ | 1 | K<-30 | A25 I |
| 22346 | $C_{10}H_{21}-O-$ | $-COO-CHCF_3-C_8H_{17}$ | 1 | K? | S6 A13.3 I |
| 22347 | $C_{10}H_{21}-O-$ | $-COO-CHCF_3-C_6H_{13}$ | 2 | K52 | A61 I |

TABLE 7

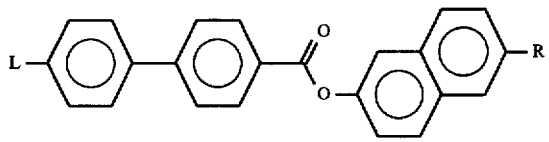

| No | L | R | | Cr | LC |
|---|---|---|---|---|---|
| 35478 | $C_4H_9-O-$ | $-CN$ | | K158 | N>300 Z |
| 35479 | $C_7H_{15}-O-$ | $-CN$ | | K132 | N292 Z |
| 35481 | $C_8H_{17}-O-$ | $-CHMe-COS-C_6H_{13}$ | 1 | K89.2 | C*120 A140.7 I |
| 35482 | $C_9H_{19}-O-$ | $-CHMe-COS-C_6H_{13}$ | 1 | K86.7 | C*125.3 A135.7 I |
| 35483 | $C_{10}H_{21}-O-$ | $-CHMe-COS-C_6H_{13}$ | 1 | K85.4 | C*127.5 A133.6 I |
| 35484 | $C_{11}H_{23}-O-$ | $-CHMe-COS-C_6H_{13}$ | 1 | K83.3 | S112.8 C*128.2 A131.1 I |
| 35485 | $C_{12}H_{25}-O-$ | $-CHMe-COS-C_6H_{13}$ | 1 | K86.9 | S104.8 C*128.6 A129.1 I |
| 35486 | $C_{13}H_{27}-O-$ | $-CHMe-COS-C_6H_{13}$ | 1 | K81.9 | S102.6 C*128.8 I |
| 35487 | $C_{14}H_{29}-O-$ | $-CHMe-COS-C_6H_{13}$ | 1 | K77.4 | S103 C*124.4 I |
| 35488 | $C_7H_{15}-O-$ | $-CHMe-COO-CHMe-C_3H_7$ | 5 | K98 | C*100.8 A141.8 N*151 I |
| 35489 | $C_8H_{17}-O-$ | $-CHMe-COO-CHMe-C_3H_7$ | 5 | K94.1 | C*101.6 A139.1 N*147.9 I |
| 35490 | $C_9H_{19}-O-$ | $-CHMe-COO-CHMe-C_3H_7$ | 5 | K79.1 | C*105.9 A134.1 A#? N*142.8 I |
| 35491 | $C_{10}H_{21}-O-$ | $-CHMe-COO-CHMe-C_3H_7$ | 5 | K66.9 | C*108.4 A#138.6 N*147.9 I |
| 35492 | $C_{11}H_{23}-O-$ | $-CHMe-COO-CHMe-C_3H_7$ | 5 | K73.3 | C*114.1 A#127.5 N*134.3 I |
| 35493 | $C_{12}H_{25}-O-$ | $-CHMe-COO-CHMe-C_3H_7$ | 5 | K69 | C*113.4 A#126.4 N*132.6 I |
| 35494 | $C_{13}H_{27}-O-$ | $-CHMe-COO-CHMe-C_3H_7$ | 5 | K68.6 | C*119.7 A#133.7 N*138.5 I |
| 35495 | $C_{14}H_{29}-O-$ | $-CHMe-COO-CHMe-C_3H_7$ | 5 | K71.7 | C*119.4 A#132.8 N*136.5 I |
| 35496 | $C_8H_{17}-O-$ | $-COO-CHCF_3-C_6H_{13}$ | 1 | K93.5 | S147.4 C*150.7 A176.4 I |
| 35497 | $C_8H_{17}-O-$ | $-COO-CHCF_3-C_8H_{17}$ | 1 | K84 | S133 C*135.6 A163.8 I |
| 35498 | $C_6H_{13}-CHCF_3-OOC-$ | $-O-C_{10}H_{21}$ | 1 | K? | S10 S75 C*106 A150.5 I |

TABLE 8

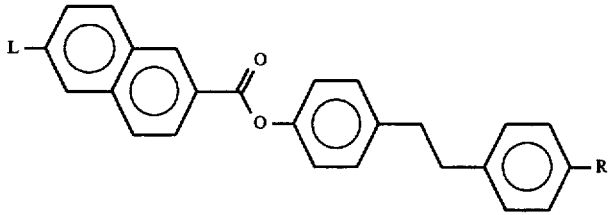

| No | L | R | Cr | LC |
|---|---|---|---|---|
| 46421 | $C_8H_{17}-$ | $-C_5H_{11}$ | K54 | S142.5 N178 I |

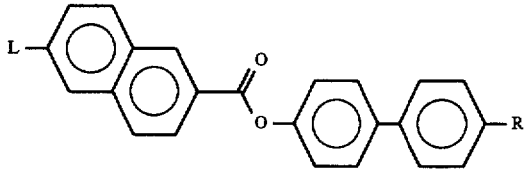

| No | L | R | | Cr | LC |
|---|---|---|---|---|---|
| 35500 | $C_7H_{15}-$ | $-F$ | | K114.9 | S187.9 N229.7 I |
| 35501 | $C_7H_{15}-O-$ | $-CN$ | | K136 | N304 Z |
| 35502 | $H_2C=CH-COO-C_5H_{12}-O-$ | $-NO_2$ | | K134 | S>180 Z |
| 35503 | $C_6H_{13}-CHCF_3-OOC-$ | $-C_{10}H_{21}$ | 1 | K49.5 | A127.7 I |
| 35504 | $C_6H_{13}-CHCF_3-OOC-$ | $-O-C_{10}H_{21}$ | 1 | K35 | S100.4 C*124.5 A152.5 I |
| 35505 | $C_6H_{13}-CHCF_3-OOC-$ | $-COO-C_{10}H_{21}$ | 1 | K40 | S96 C*97.7 A123.7 I |
| 35506 | $C_6H_{13}-CHCF_3-OOC-$ | $-OOC-C_{10}H_{21}$ | 1 | K75 | S120 C*156.9 A184.2 I |
| 35507 | $C_{10}H_{21}-O-$ | $-COO-CHCF_3-C_6H_{13}$ | 1 | K? | S97 C*120 A151.9 I |
| 35508 | $C_8H_{17}-OOC-$ | $-COO-CHCF_3-C_6H_{13}$ | 1 | K? | S64.1 C*66 A108.4 I |

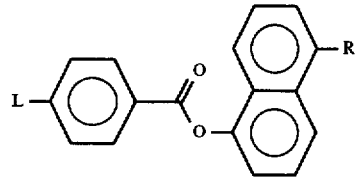

| No | L | R | | Cr | LC |
|---|---|---|---|---|---|
| 22447 | $C_5F_{11}-CH_2-O-$ | $-O-C_8H_{17}$ | | K? | A92 I |
| 22448 | $C_5F_{11}-CH_2-O-$ | $-O-C_3H_6-CHMe-C_2H_5$ | 1 | K? | C*37 A80 I |

TABLE 9

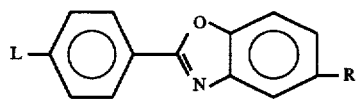

| No | L | R | | Cr | LC |
|---|---|---|---|---|---|
| 7534 | $C_8H_{17}-$ | $-C_6H_{13}$ | | K39.9 | C23 A25.5 I |
| 7538 | $C_6H_{13}-O-$ | $-C_4H_9$ | | K68.7 | C45.1 A55.8 I |
| 7539 | $C_{10}H_{21}-O-$ | $-C_8H_{17}$ | | K57.7 | C71.5 A77.3 I |
| 7542 | $C_{10}H_{21}-O-$ | $-O-C_8H_{17}$ | | K60.1 | C81.7 A89.1 I |
| 7543 | $C_8H_{17}-O-$ | $-CO-C_{10}H_{21}$ | | K106.9 | C103.8 A120.4 I |
| 7545 | $C_{10}H_{21}-O-$ | $-COO-C_8H_{17}$ | | K103.6 | A88.2 I |
| 7548 | $C_6H_{13}-COO-$ | $-C_8H_{17}$ | | K51.8 | A64.3 N49.8 U |
| 7549 | $C_6H_{13}-CHF-CH_2-O-$ | $-C_8H_{17}$ | 1 | K77.9 | A69.6 I |

TABLE 9-continued
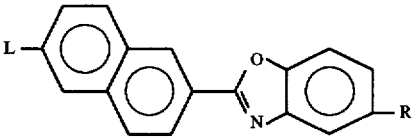
| No | L | R | Cr | LC |
|---|---|---|---|---|
| 8788 | $C_{10}H_{21}-O-$ | $-C_4H_9$ | K90.1 | A109.9 I |
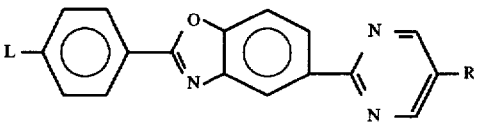
| No | L | R | Cr | LC |
|---|---|---|---|---|
| 27629 | $C_8H_{17}-$ | $-C_{12}H_{25}$ | K76.6 | C99.4 N128.2 I |
TABLE 10
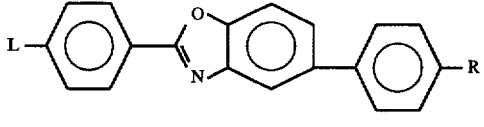
| No | L | R | Cr | LC |
|---|---|---|---|---|
| 28106 | $C_8H_{17}-$ | $-C_8H_{17}$ | K77.8 | C101.4 N121.8 I |
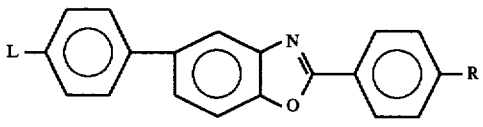
| No | L | R | Cr | LC |
|---|---|---|---|---|
| 26603 | $C_{10}H_{21}-$ | $-C_8H_{17}$ | K77.5 | C114.9 N123.8 I |
| 26604 | $C_{10}H_{21}-$ | $-O-C_{10}H_{21}$ | K92.2 | C132.8 A135.9 N143.4 I |
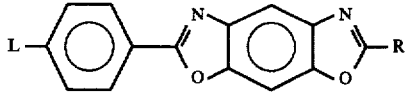
| No | L | R | Cr | LC |
|---|---|---|---|---|
| 8726 | $C_4H_9-$ | $-C_6H_{13}$ | K90 | A96 N106 I |
TABLE 11
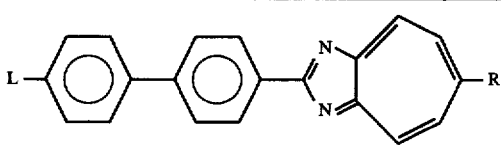
| No | L | R | Cr | LC |
|---|---|---|---|---|
| 27356 | H- | $-O-C_4H_9$ | K211 | A207 N240 I |
| 27357 | H- | $-O-C_6H_{13}$ | K183 | B225 A228 U |
TABLE 11-continued
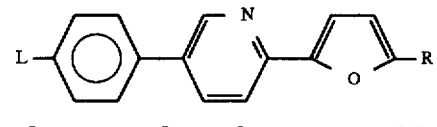
| No | L | R | Cr | LC |
|---|---|---|---|---|
| 27633 | $C_4H_9-$ | -H | K75 | S96 I |
| 27634 | $C_5H_{11}-$ | -H | K65 | S106 I |
| 27635 | $C_6H_{13}-$ | -H | K55 | S103 I |
| 27636 | $C_7H_{15}-$ | -H | K48 | S100 S103 S107 I |
| 27637 | $C_8H_{17}-$ | -H | K42 | S102 I |
| 27638 | $C_4H_9-O-$ | -H | K106 | S136 I |

TABLE 11-continued

| | | | | |
|---|---|---|---|---|
| 27639 | C$_5$H$_{11}$—O— | —H | K62 | S133 I |
| 27640 | C$_6$H$_{13}$—O— | —H | K76 | S133 I |
| 27641 | C$_7$H$_{15}$—O— | —H | K63 | S136 I |
| 27642 | C$_8$H$_{17}$—O— | —H | K54 | S137 I |

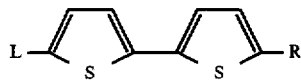

| No | L | R | Cr | LC |
|---|---|---|---|---|
| 8268 | C$_4$H$_9$—S— | —Br | K? | I |
| 8269 | C$_4$H$_9$—S— | —CN | K30.3 | N–63 E |
| 8270 | C$_7$H$_{15}$— | —C$_7$H$_{15}$ | K56 | I |
| 8278 | C$_7$H$_{15}$— | —COO—C$_2$H$_5$ | K84 | S47 I |
| 8279 | C$_4$H$_9$—O— | —COO—C$_2$H$_5$ | K87 | S86 I |
| 8280 | C$_5$H$_{11}$—O— | —COO—C$_2$H$_5$ | K72 | S90 I |
| 8281 | C$_6$H$_{13}$—O— | —COO—C$_2$H$_5$ | K60 | S82 I |
| 8282 | C$_7$H$_{15}$—O— | —COO—C$_2$H$_5$ | K86 | S82 I |
| 8283 | C$_8$H$_{17}$—O— | —COO—C$_2$H$_5$ | K72 | S84 I |

TABLE 12

| No | L | R | Cr | LC |
|---|---|---|---|---|
| 29065 | C$_3$H$_7$— | —C$_3$H$_7$ | K50 | S74 I |
| 29066 | C$_4$H$_9$— | —C$_4$H$_9$ | K50 | S75 I |
| 29067 | C$_5$H$_{11}$— | —C$_5$H$_{11}$ | K53 | S77 I |
| 29068 | C$_6$H$_{13}$— | —C$_6$H$_{13}$ | K51 | S82 I |
| 29069 | C$_7$H$_{15}$— | —C$_7$H$_{15}$ | K55 | G78 F83 C89 I |
| 29070 | C$_8$H$_{17}$— | —C$_8$H$_{17}$ | K65 | G72 F87 C91 I |
| 29071 | C$_9$H$_{19}$— | —C$_9$H$_{12}$ | K64 | G62 F91 C95 I |
| 29072 | C$_{10}$H$_{21}$— | —C$_{10}$H$_{21}$ | K71 | F95 C96 I |
| 29074 | C$_4$H$_9$— | —CO—C$_3$H$_7$ | K148.3 | A155.7 I |
| 29075 | C$_5$H$_{11}$— | —CO—C$_4$H$_9$ | K137.2 | A163 I |
| 29076 | C$_6$H$_{13}$— | —CO—C$_5$H$_{11}$ | K138.4 | A162 I |
| 29077 | C$_7$H$_{15}$— | —CO—C$_6$H$_{13}$ | K132 | C138.9 A161.8 |
| 29078 | C$_8$H$_{17}$— | —CO—C$_7$H$_{15}$ | K133 | C151 A159.7 I |
| 29079 | C$_9$H$_{19}$— | —CO—C$_8$H$_{17}$ | K129.4 | C154.2 A158.7 I |
| 29080 | C$_{10}$H$_{21}$— | —CO—C$_9$H$_{19}$ | K127 | C152 I |

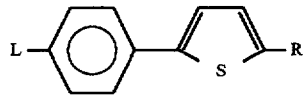

| No | L | R | Cr | LC |
|---|---|---|---|---|
| 5713 | Br— | —CO—C$_7$H$_{15}$ | K116.1 | A123.8 I |
| 5719 | NC— | —C$_8$H$_{17}$ | K49.9 | A20.8 N22.2 I |
| 5723 | NC— | —S—C$_4$H$_9$ | K32.6 | N–52 E |
| 5727 | C$_4$H$_9$SiMe$_2$—C$_3$H$_6$—O— | —C$_{10}$H$_{21}$ | K57 | S43 I |
| 5730 | C$_4$H$_9$—S— | —CN | K55.7 | N5 E |
| 5732 | C$_2$H$_5$—O— | —CO—C$_7$H$_{15}$ | K120.8 | A123.1 I |
| 5733 | C$_3$H$_7$—O— | —CO—C$_7$H$_{15}$ | K124.4 | A122.8 I |
| 5734 | C$_4$H$_9$—O— | —CO—C$_7$H$_{15}$ | K127.6 | A130.9 I |
| 5735 | C$_5$H$_{11}$—O— | —CO—C$_7$H$_{15}$ | K120.5 | A127.4 I |
| 5736 | C$_6$H$_{13}$—O— | —CO—C$_7$H$_{15}$ | K120 | A129.8 I |
| 5737 | C$_7$H$_{15}$—O— | —CO—C$_7$H$_{15}$ | K113 | A127.4 I |
| 5738 | C$_8$H$_{17}$—O— | —CO—C$_7$H$_{15}$ | K109.5 | A126.2 I |
| 5739 | C$_9$H$_{19}$—O— | —CO—C$_7$H$_{15}$ | K107.5 | A123.8 I |
| 5740 | C$_{12}$H$_{25}$—O— | —CO—C$_7$H$_{15}$ | K100.6 | S93.8 A122.2 I |

TABLE 13

| No | L | R | Cr | LC |
|---|---|---|---|---|
| 36004 | C$_5$H$_{11}$— | —C$_5$H$_{11}$ | K21.5 | B88.4 A96.7 I |
| 36005 | C$_6$H$_{13}$— | —C$_5$H$_{11}$ | K22.5 | B94.7 A97.2 I |
| 36006 | C$_7$H$_{15}$— | —C$_5$H$_{11}$ | K20.5 | B96.2 A99.8 I |
| 36007 | C$_8$H$_{17}$— | —C$_5$H$_{11}$ | K21 | B96.8 A99.1 I |
| 36008 | C$_9$H$_{19}$— | —C$_5$H$_{11}$ | K23.7 | B97.2 A100.1 I |
| 36009 | C$_{10}$H$_{21}$— | —C$_5$H$_{11}$ | K55 | B98.4 I |

TABLE 13-continued

| No | L | R | Cr | LC |
|---|---|---|---|---|

TABLE 13-continued

| No | L | R | Cr | LC |
|---|---|---|---|---|
| 27648 | C₄H₉—O— | —H | K128 | S150 I |
| 27649 | C₆H₁₃— | —C₂H₅ | K56 | S155 I |
| 27650 | C₄H₉—O— | —C₂H₅ | K102 | S180 I |
| 27651 | C₄H₉—O— | —C₅H₁₁ | K61 | S176 I |

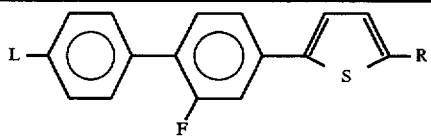

| No | L | R | Cr | LC |
|---|---|---|---|---|
| 27643 | C₅H₁₁— | —C₅H₁₁ | K42.4 | C47.9 A62 N97.8 I |
| 27644 | C₅H₁₁— | —CO—C₄H₉ | K74.9 | A186.8 I |

TABLE 14

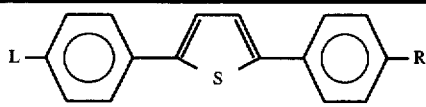

| No | L | R | Cr | LC |
|---|---|---|---|---|
| 25783 | C₆H₃— | —O—C₆H₁₃ | K148 | A152 N155 I |

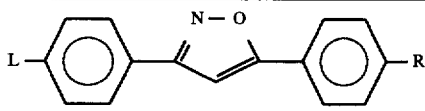

| No | L | R | Cr | LC |
|---|---|---|---|---|
| 25800 | C₆H₁₃—O— | —O—C₆H₁₃ | K110.8 | C130.6 N161 I |
| 25801 | C₇H₁₅—O— | —O—C₇H₁₅ | K109.8 | C139.4 N155.8 I |
| 25802 | C₈H₁₇—O— | —O—C₈H₁₇ | K107.3 | C149 N157.3 I |
| 25803 | C₁₀H₂₁—O— | —O—C₁₀H₂₁ | K98.6 | C147.4 I |
| 25805 | H₂C=CH—C₄H₈—O— | —O—C₄H₈—CH=CH₂ | K99 | A114 N144 I |
| 25806 | H₂C=CH—C₉H₁₈—O— | —O—C₉H₁₈—CH=CH₂ | K92 | A145 I |

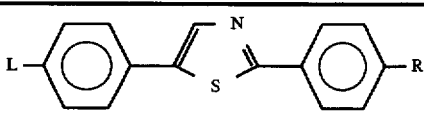

| No | L | R | Cr | LC |
|---|---|---|---|---|
| 25816 | Me₃Si—C₃H₆—O— | —C₆H₁₃ | K96 | C109 I |
| 25817 | C₄H₉SiMe₂—C₃H₆—COO— | —C₆H₁₃ | K51 | C90 I |
| 25818 | C₆H₁₃— | —C₆H₁₃ | K68.8 | A116.5 N120.1 I |
| 25819 | C₉H₁₉— | —C₆H₁₃ | K61 | C72.2 A126.8 I |
| 25828 | C₃H₇—O— | —C₆H₁₃ | K79 | C70 A101 N147.5 I |
| 25841 | C₃H₇—O— | —O—C₈H₁₇ | K78 | C98 N161 I |
| 25842 | C₄H₉—COO— | —C₆H₁₃ | K101.9 | C128.5 N149.4 I |

TABLE 15

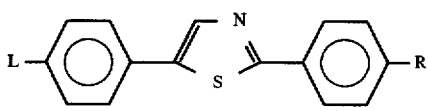

TABLE 15-continued

| No | L | R | Cr | LC |
|---|---|---|---|---|
| 25843 | $C_6H_{13}$—COO— | —$C_6H_{13}$ | K73.1 | S83.2 C139.3 N148.7 I |
| 25844 | $C_8H_{17}$—COO— | —$C_6H_{13}$ | K58 | S75.8 C146.4 N148.1 I |
| 25845 | $C_8H_{17}$—COO— | —$C_8H_{17}$ | K59.4 | S74.5 S78.5 C148.5 I |
| 25846 | $C_{10}H_{21}$—COO— | —$C_6H_{13}$ | K74.9 | S86.2 C147 I |

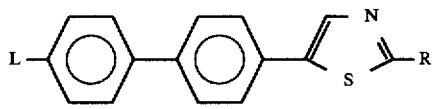

| No | L | R | Cr | LC |
|---|---|---|---|---|
| 26979 | $C_6H_{13}$— | —$C_9H_{19}$ | K134.2 | S166.3 S167.3 I |

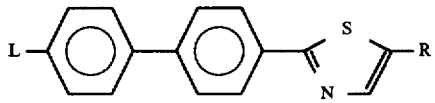

| No | L | R | Cr | LC |
|---|---|---|---|---|
| 26980 | $C_4H_9$— | —$C_7H_{15}$ | K76 | S130 N137 I |

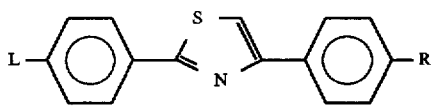

| No | L | R | Cr | LC |
|---|---|---|---|---|
| 25848 | $C_{10}H_{21}$— | —O—$CH_3$ | K95 | N154 U |
| 25849 | $C_{10}H_{21}$— | —O—$C_6H_{13}$ | K43 | C53 A142 U |
| 25850 | $C_{10}H_{21}$— | —O—$C_7H_{15}$ | K54 | B64 C110 A143 U |
| 25851 | $C_{10}H_{21}$— | —O—$C_8H_{17}$ | K59 | B73 C120 A146 U |
| 25852 | $C_{10}H_{21}$— | —O—$C_{10}H_{21}$ | K66 | B84 C137 A144.6 I |

TABLE 16

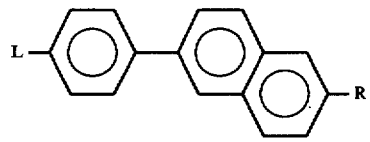

| No | L | R | Cr | LC |
|---|---|---|---|---|
| 7226 | NC— | —$C_8H_{17}$ | K48 | A91.5 N113 I |
| 7227 | NC— | —$C_9H_{19}$ | K44 | A95 N104 I |
| 7235 | NC— | —O—$C_8H_{17}$ | K85 | A94 N140 I |
| 7243 | NC— | —OOC—CH=CH—$CH_3$ | K139 | N259 Z |
| 7244 | NC— | —OOC—CH=CH—$C_2H_5$ | K113 | N229 Z |

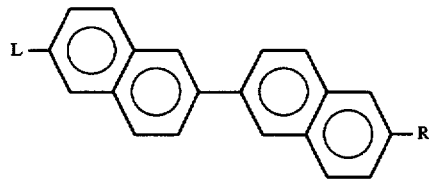

| No | L | R | Cr | LC |
|---|---|---|---|---|
| 8776 | $C_5H_{11}$— | —$C_5H_{11}$ | K146.5 | E145.5 A163.5 N171.5 I |
| 8777 | $C_6H_{13}$— | —$C_6H_{13}$ | K138 | E135.5 A156.5 I |

TABLE 16-continued

| | | | | |
|---|---|---|---|---|
| 8778 | C$_7$H$_{15}$— | —C$_7$H$_{15}$ | K125.5 | E135.5 A163 I |
| 8779 | C$_8$H$_{17}$— | —C$_8$H$_{17}$ | K123 | E129 A156.5 I |
| 8780 | C$_9$H$_{19}$— | —C$_9$H$_{19}$ | K113.5 | E110 A148 I |
| 8783 | C$_3$H$_7$—O— | —O—C$_3$H$_7$ | K194 | A237 N278 I |
| 8784 | C$_4$H$_9$—O— | —O—C$_4$H$_9$ | K136 | E190 A241 N256 I |
| 8785 | C$_5$H$_{11}$—O— | —O—C$_5$H$_{11}$ | K136 | E178 A236 N244 I |
| 8786 | C$_6$H$_{13}$—O— | —O—C$_6$H$_{13}$ | K141 | E170 A229 I |
| 8787 | C$_7$H$_{15}$—O— | —O—C$_7$H$_{15}$ | K130 | E163 N225 I |

TABLE 17

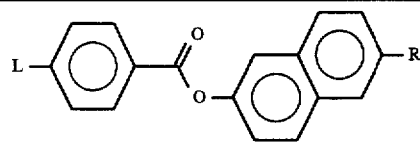

| No | L | R | Cr | LC |
|---|---|---|---|---|
| 22138 | NC— | —O—C$_8$H$_{17}$ | K128 | A122 N156 I |
| 22139 | NC— | —O—C$_9$H$_{19}$ | K125 | A140 N152 I |
| 22140 | NC— | —O—C$_{10}$H$_{21}$ | K125 | A146 N149 I |
| 22141 | NC— | —O—C$_{11}$H$_{23}$ | K122.5 | A149 I |
| 22142 | NC— | —O—C$_{12}$H$_{25}$ | K123 | A151 I |
| 22146 | O$_2$N— | —O—C$_8$H$_{17}$ | K98 | A109 N136 I |
| 22147 | O$_2$N— | —O—C$_9$H$_{19}$ | K94 | A127.5 N135 I |
| 22148 | O$_2$N— | —O—C$_{10}$H$_{21}$ | K93 | A135 N135.5 I |
| 22149 | O$_2$N— | —O—C$_{11}$H$_{23}$ | K92 | A136.5 I |
| 22150 | O$_2$N— | —O—C$_{12}$H$_{25}$ | K92 | A136.5 I |
| 22161 | C$_9$H$_{19}$— | —CN | K74 | A105.9 N131.11 |

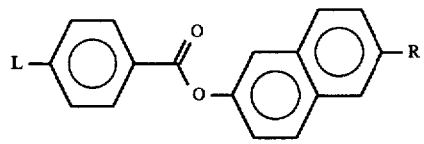

| No | L | R | | Cr | LC |
|---|---|---|---|---|---|
| 22168 | C$_{10}$H$_{21}$—O— | —CN | | K78 | R72 A139 N152 I |
| 22169 | C$_{11}$H$_{23}$—O— | —CN | | K79 | A146 N149.5 I |
| 22172 | C$_8$H$_{17}$—S— | —CN | | K99 | A109.5 N129.5 I |
| 22173 | C$_9$H$_{19}$—S— | —CN | | K107 | A122 N127 I |
| 22174 | C$_{10}$H$_{21}$—S— | —CN | | K100 | A128.5 I |
| 22175 | C$_{11}$H$_{23}$—S— | —CN | | K100 | A130.5 I |
| 22176 | C$_{12}$H$_{25}$—S— | —CN | | K104 | A133 I |
| 22181 | C$_2$H$_5$—CHMe—C$_5$H$_{10}$—O— | —CN | S | K80 | A122 N*135 I |
| 22182 | C$_9$H$_{19}$—O— | —COO—C$_3$H$_6$—SiMe$_2$C$_4$H$_9$ | | K48 | C67 A81 I |
| 22184 | C$_6$H$_{13}$—O— | —C$_5$H$_{11}$ | | K81 | A84.9 N120 I |
| 22185 | C$_8$H$_{17}$—O— | —C$_7$H$_{15}$ | | K73 | A106.1 N111.3 I |
| 22186 | C$_{10}$H$_{21}$—O— | —C$_4$H$_9$—CHMe—OOC—C$_2$H$_5$ | 1 | K22.1 | A9.1 I |
| 22187 | C$_{10}$H$_{21}$—O— | —O—C$_2$H$_4$—O—C$_4$H$_9$ | | K63 | C72.3 N98.3 I |
| 22188 | C$_{10}$H$_{21}$—O— | —O—CH$_2$—CHMe—O—C$_2$H$_5$ | 1 | K49 | C*59 A64 N*73 I |

TABLE 18

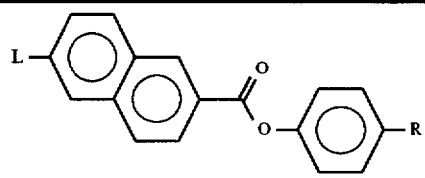

TABLE 18-continued

| No | L | R | Cr | LC |
|---|---|---|---|---|
| 22305 | $C_7H_{15}-$ | $-C_7H_{15}$ | K83.1 | C58 N109.5 I |
| 22307 | $C_6H_{13}-O-$ | $-C_5H_{11}$ | K81 | A85 N120 I |
| 22309 | $C_8H_{17}-O-$ | $-C_7H_{15}$ | K73 | A106.1 N111.3 I |
| 22317 | $C_7H_{15}-$ | $-O-C_7H_{15}$ | K83.1 | C58 N109.5 I |
| 22318 | $C_8H_{17}-$ | $-O-C_6H_{13}$ | K70 | C73 N109 I |
| 22320 | $C_6H_{13}-O-$ | $-O-C_7H_{15}$ | K82 | C88.4 N133.4 I |
| 22321 | $C_6H_{13}-O-$ | $-O-C_8H_{17}$ | K85.1 | C89.1 N133.3 I |
| 22322 | $C_7H_{15}-O-$ | $-O-C_7H_{15}$ | K88.9 | C94.7 A105.5 N129.8 I |
| 22323 | $C_7H_{15}-O-$ | $-O-C_8H_{17}$ | K82.5 | C103.8 A110.7 N132.2 I |
| 22324 | $C_7H_{15}-O-$ | $-O-C_9H_{19}$ | K90.4 | C103 A113.8 N128 I |
| 22325 | $C_8H_{17}-O-$ | $-O-C_7H_{15}$ | K84.7 | C93.8 A115.7 N129.7 I |
| 22326 | $C_8H_{17}-O-$ | $-O-C_8H_{17}$ | K85.5 | C101.8 A119.8 N131 I |
| 22327 | $C_8H_{17}-O-$ | $-O-C_9H_{19}$ | K90 | C104.2 A122.4 N131.8 I |

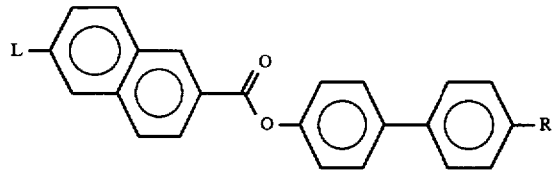

| No | L | R | Cr | LC |
|---|---|---|---|---|
| 35500 | $C_7H_{15}-$ | $-F$ | K114.9 | S187.9 N229.7 I |
| 35502 | $H_2C=CH-COO-C_6H_{12}-O-$ | $-NO_2$ | K134 | S>180 Z |
| 35503 | $C_6H_{13}-CHCF_3-OOC-$ | $-C_{10}H_{21}$ | 1 K49.5 | A127.7 I |
| 35504 | $C_6H_{13}-CHCF_3-OOC-$ | $-O-C_{10}H_{21}$ | 1 K35 | S100.4 C*24.5 A152.5 I |
| 35505 | $C_6H_{13}-CHCF_3-OOC-$ | $-COO-C_{10}H_{21}$ | 1 K40 | S96 C*97.7 A123.7 I |
| 35506 | $C_6H_{13}-CHCF_3-OOC-$ | $-OOC-C_{10}H_{21}$ | 1 K75 | S120 C*156.9 A184.2 I |
| 35507 | $C_{10}H_{21}-O-$ | $-COO-CHCF_3-C_6H_{13}$ | 1 K? | S97 C*120 A151.9 I |
| 35508 | $C_8H_{17}-OOC-$ | $-COO-CHCF_3-C_6H_{13}$ | 1 K? | S64.1 C*66 A108.4 I |

TABLE 19

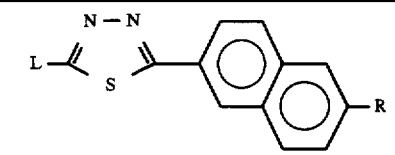

| No | L | R | Cr | LC |
|---|---|---|---|---|
| 24420 | $C_8H_{17}-$ | $-C_5H_{11}$ | K44.5 | S65 N84 I |
| 24421 | $C_8H_{17}-$ | $-C_6H_{13}$ | K46.5 | S36.5 N69.5 I |

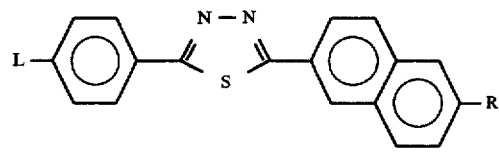

| No | L | R | Cr | LC |
|---|---|---|---|---|
| 8289 | $C_6H_{13}-$ | $-O-C_6H_{13}$ | K107.4 | C114.1 I |
| 8290 | $C_6H_{13}-$ | $-C-C_{10}H_{21}$ | K92.8 | C116.5 I |
| 8291 | $C_6H_{13}-$ | $-OOC-C_6H_{13}$ | K81.7 | C106.7 A110.9 I |

TABLE 19-continued

| 28262 | $C_6H_{13}-$ | $-O-C_4H_9$ | K79.5 | C155.1 N230.7 I |
|---|---|---|---|---|
| 28263 | $C_{10}H_{21}$ | $-O-C_{10}H_{21}$ | K80.3 | C198.2 I |
| 28265 | $C_6H_{13}-$ | $-OOC-C_6H_{13}$ | K82.3 | C199.4 N225.2 I |

TABLE 20

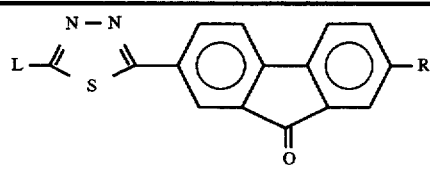

| No | L | R | Cr | LC |
|---|---|---|---|---|
| 8292 | $C_6H_{13}-$ | $-C_8H_{17}$ | K87.3 | S118.6 A186.4 I |
| 8293 | $C_8H_{17}-$ | $-C_8H_{17}$ | K82.4 | S92.7 C149 A181.2 I |

| No | L | R | Cr | LC |
|---|---|---|---|---|
| 8294 | $C_6H_{13}-$ | $-C_8H_{17}$ | K84.6 | S119.5 A147.5 I |
| 8295 | $C_8H_{17}-$ | $-C_8H_{17}$ | K34.8 | S117.5 A155.2 I |

TABLE 21

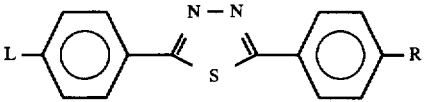

| No | L | R | Cr | LC |
|---|---|---|---|---|
| 25914 | C₅H₁₁— | —H | K76 | N56 U |
| 25915 | C₆H₁₃— | —H | K75 | S60 N80 I |
| 25916 | C₇H₁₅— | —H | K79 | S64 N86 I |
| 25917 | C₁₂H₂₅— | —H | K84 | A95 I |
| 25918 | C₂H₅—O— | —H | K120 | N165 U |
| 25919 | C₃H₇—O— | —H | K110 | N101 U |
| 25920 | C₄H₉—O— | —H | K84 | N140 U |
| 25921 | C₅H₁₁—O— | —H | K80 | N134 U |
| 25922 | C₆H₁₃—O— | —H | K80.5 | N134 U |
| 25923 | C₇H₁₅—O— | —H | K73.5 | N149.5 U |
| 25924 | C₈H₁₇—O— | —H | K83 | N142.5 U |
| 25925 | C₉H₁₉—O— | —H | K96 | A126 I |
| 25926 | C₁₀H₂₁—O— | —H | K99 | A126 I |
| 25931 | C₆H₁₃—O— | —F | K97 | A198 I |
| 25932 | C₆H₁₃—O— | —Cl | K132 | A244 I |
| 25933 | C₆H₁₃—O— | —Br | K135 | A239 I |
| 25934 | C₆H₁₃— | —CN | K118 | A220 N233 I |
| 25935 | C₅H₁₁—O— | —CN | K142 | A246 N265 I |
| 25936 | C₆H₁₃—O— | —CN | K146 | A258 N264 I |
| 25937 | C₆H₁₃—O— | —NO₂ | K123 | A241 I |
| 25938 | C₁₀H₂₁— | —O—C₄H₆—SiMe₂C₄H₉ | K46 | C122 E |
| 25943 | C₅H₁₁— | —C₅H₁₁ | K93 | C123 N164 I |
| 25944 | C₆H₁₃— | —C₆H₁₃ | K89 | C137 N154 B |
| 25945 | C₆H₁₃— | —C₁₀H₂₁ | K66 | C168 N172.9 I |
| 25946 | C₇H₁₅— | —C₇H₁₅ | K81 | C149 N158 I |
| 25947 | C₈H₁₇— | —C₈H₁₇ | K78 | C151 N152 B |

TABLE 22

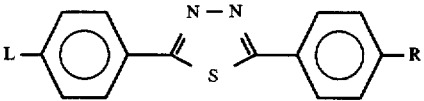

| No | L | R | | Cr | LC |
|---|---|---|---|---|---|
| 25949 | C₂H₅— | —O—C₇H₁₅ | | K67 | A142 N178 I |
| 25952 | C₅H₁₁— | —C—C₆H₁₃ | | K55 | C158 N186 I |
| 25953 | C₅H₁₁— | —O—C₈H₁₇ | | K80 | C167 N182 I |
| 25954 | C₆H₁₃— | —O—C₄H₉ | | K80.6 | C141 N183.5 I |
| 25955 | C₆H₁₃— | —O—C₇H₁₅ | | K69 | A166 N179 I |
| 25956 | C₆H₁₃— | —O—C₉H₁₉ | | K77 | C171 N175 I |
| 25957 | C₇H₁₅— | —O—C₈H₁₇ | | K79 | C174 N178 I |
| 25958 | C₈H₁₇— | —O—C₇H₁₅ | | K72 | A170 N177 I |
| 25960 | C₁₀H₂₁— | —O—C₇H₁₅ | | K76 | C171 N181 B |
| 25961 | C₁₀H₂₁— | —O—C₆H₁₇ | | K79 | C173 I |
| 25962 | C₁₀H₂₁— | —O—C₁₀H₂₁ | | K78 | A154 I |
| 25963 | C₁₂H₂₅— | —O—C₉H₁₉ | | K74 | C169 I |
| 25965 | C₁₀H₂₁— | —COO—CH₃ | | K140 | A224 I |
| 25966 | C₆H₁₃— | —OOC—C₈H₁₇ | | K58.2 | S68.1 C172.6 N176.1 I |
| 25967 | C₁₀H₂₁— | —OOC—CH₃ | | K117 | C134 N183 I |
| 25968 | C₁₀H₂₁— | —OOC—C₂H₅ | | K107 | C153 N181 I |
| 25969 | C₁₀H₂₁— | —OOC—CHMe—C—CH₃ | 1 | K108 | C*139 N*140 I |
| 25970 | C₁₀H₂₁— | —OOC—CHMe—C—C₆H₁₃ | 1 | K110 | C*121 I |
| 25971 | C₁₀H₂₁— | —OCOO—C₄H₉ | | K64 | C146 A147 N166 I |
| 25972 | C₁₀H₂₁— | —OCOO—C₇H₁₅ | | K80 | C153 N157 I |
| 25974 | CH₃—O— | —C—C₆H₁₃ | | K93 | A109 N215 I |
| 25977 | C₄H₉—O— | —C—C₄H₉ | | K145 | A156 N222 I |

TABLE 23

L—⟨phenyl⟩—C(=N-N=C)—S—⟨cyclohexyl⟩—R

| No | L | R | Cr | LC |
|---|---|---|---|---|
| 27803 | NC— | —C$_6$H$_{13}$ | K128 | A169 N199 I |
| 27804 | C$_4$H$_9$— | —C$_3$H$_7$ | K76 | A96 N150 I |
| 27805 | C$_4$H$_9$— | —C$_4$H$_9$ | K71 | A120 N146 I |
| 27806 | C$_4$H$_9$— | —C$_5$H$_{11}$ | K52 | A115 N138 I |
| 27807 | C$_4$H$_9$— | —C$_6$H$_{13}$ | K58 | A117 N151 I |
| 27808 | C$_6$H$_{13}$— | —C$_2$H$_5$ | K50 | A77 N115 I |
| 27809 | C$_6$H$_{13}$— | —C$_3$H$_7$ | K61 | A126 N146 I |
| 27810 | C$_6$H$_{13}$— | —C$_4$H$_9$ | K47 | A133 N139 I |
| 27811 | C$_6$H$_{13}$— | —C$_5$H$_{11}$ | K50 | A148 N150 I |
| 27812 | C$_6$H$_{13}$— | —C$_6$H$_{13}$ | K50 | A145 I |
| 27815 | C$_9$H$_{19}$—O— | —C$_4$H$_9$ | K111 | A166 N167 I |
| 27816 | C$_9$H$_{19}$—O— | —C$_6$H$_{13}$ | K108 | C130 N169 I |
| 27817 | C$_{10}$H$_{21}$—O— | —C$_6$H$_{13}$ | K105 | C122 N165 I |
| 27818 | C$_{10}$H$_{21}$—O— | —C$_7$H$_{15}$ | K87 | C143 A169 I |
| 27819 | C$_{12}$H$_{25}$—O— | —C$_6$H$_{13}$ | K58 | C136 A146 I |
| 27820 | C$_4$H$_9$—CMe$_2$—C$_4$H$_9$—O— | —C$_6$H$_{13}$ | K93 | C101 A111 N112 I |
| 27821 | C$_4$H$_9$—CMe$_2$—C$_6$H$_{12}$—O— | —C$_6$H$_{13}$ | K90 | C117 A129 N129 I |
| 27823 | C$_6$H$_{13}$—O—CHMe—COO— | —C$_2$H$_5$ | 1 K75 | A61 I |
| 27824 | H$_2$C/CH$_2$ CH—C$_{11}$H$_{22}$—O— | —C$_5$H$_{11}$ | K111 | C113 A156 N157 I |

L—⟨phenyl⟩—C(=N-N=C)—S—⟨naphthyl⟩—R

| No | L | R | Cr | LC |
|---|---|---|---|---|
| 28262 | C$_6$H$_{13}$— | —O—C$_4$H$_9$ | K79.5 | C155.1 N230.7 I |
| 28263 | C$_{10}$H$_{21}$— | —O—C$_{10}$H$_{21}$ | K80.3 | C198.2 I |
| 28265 | C$_6$H$_{13}$— | —OOC—C$_6$H$_{13}$ | K82.3 | C199.4 N225.2 I |

TABLE 24

L—⟨phenyl⟩—C(=N-N=C)—S—CH=CH—⟨phenyl⟩—R

| No | L | R | Cr | LC |
|---|---|---|---|---|
| 32163 | H— | —O—C$_9$H$_{19}$ | K105 | S126 I |
| 32165 | C$_6$H$_{13}$— | —O—C$_4$H$_9$ | K68 | S115 N165 I |
| 32166 | C$_6$H$_{13}$— | —O—C$_9$H$_{19}$ | K83 | S167 N177 I |
| 32167 | C$_4$H$_9$—O— | —O—C$_4$H$_9$ | K103 | S117 N210 I |
| 32168 | C$_4$H$_9$—O— | —O—C$_9$H$_{19}$ | K105 | S141 N195 I |
| 32170 | C$_6$H$_{13}$—O— | —O—C$_5$H$_{11}$ | K95 | S145 N199 I |

L—⟨phenyl⟩—C(=N-N=C)—S—CH$_2$CH$_2$—⟨phenyl⟩—R

| No | L | R | Cr | LC |
|---|---|---|---|---|
| 32162 | C$_5$H$_{13}$— | —C$_4$H$_9$ | K56 | C89 A123 I |

L—⟨phenyl⟩—⟨pyridazine⟩—C(=N-N=C)—S—R

TABLE 24-continued

| No | L | R | Cr | LC |
|---|---|---|---|---|
| 27671 | C$_6$H$_{13}$— | —H | K82 | S128 I |
| 27672 | C$_6$H$_{13}$—O— | —H | K95 | S152 I |
| 27673 | C$_4$H$_9$— | —C$_5$H$_{11}$ | K47 | S143 I |

TABLE 25

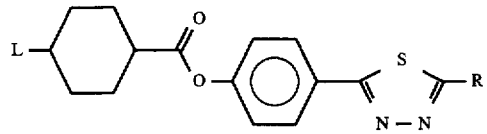

| No | L | R | | Cr | LC |
|---|---|---|---|---|---|
| 8296 | C$_6$H$_{13}$— | —C$_8$H$_{17}$ | | K50.9 | A126.6 I |
| 8297 | C$_{10}$H$_{21}$— | —C$_8$H$_{17}$ | | K37.1 | A128.7 I |
| 8299 | C$_8$H$_{13}$—CHF— | —C$_8$H$_{17}$ | 1 | K63.4 | A132.9 I |

| No | L | R | Cr | LC |
|---|---|---|---|---|
| 37286 | C$_3$H$_7$— | —C$_7$H$_{15}$ | K95.5 | S88 G99.5 C118 A154 N174.5 I |
| 37287 | C$_3$H$_7$— | —C$_{10}$H$_{21}$ | K76.5 | S94.5 S95.5 C120.9 A159.7 N164.4 I |
| 37288 | C$_4$H$_9$— | —C$_9$H$_{19}$ | K81 | S87 S98 C102 A103 N164 I |
| 37289 | C$_5$H$_{11}$— | —C$_7$H$_{15}$ | K50 | G101 C105 A173 N176 I |
| 37290 | C$_5$H$_{11}$— | —C$_{10}$H$_{21}$ | K69.2 | S98.4 S107.3 S119.9 S170.6 I |
| 37291 | C$_6$H$_{13}$— | —C$_7$H$_{15}$ | K52 | G83 C126 A159 N166 I |
| 37292 | C$_7$H$_{15}$— | —C$_7$H$_{15}$ | K50 | G101 B133 A173 I |
| 37293 | C$_8$H$_{17}$— | —C$_7$H$_{15}$ | K62 | G94 B134 A172 I |
| 37294 | C$_5$H$_{11}$— | —CHMe—C$_2$H$_5$ 2 | K55.1 | S103.8 A114.7 N120.6 I |

TABLE 26

| No | L | R | Cr | LC |
|---|---|---|---|---|
| 36949 | C$_3$H$_7$—O— | —C$_7$H$_{15}$ | K94 | C136 A144 N153 I |
| 36950 | C$_4$H$_9$—O— | —C$_7$H$_{15}$ | K68 | C144 A147 N154 I |
| 36951 | C$_4$H$_9$—O— | —C$_{11}$H$_{23}$ | K90 | C145 A155 I |
| 36952 | C$_6$H$_{13}$—O— | —C$_7$H$_{15}$ | K68 | C103 A171 I |

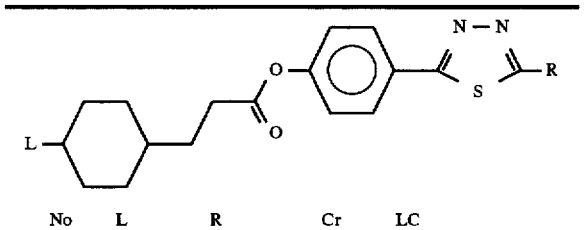

| No | L | R | Cr | LC |
|---|---|---|---|---|
| 37296 | C$_2$H$_5$— | —C$_9$H$_{19}$ | K76 | G94 C117 A124 I |
| 37297 | C$_3$H$_7$— | —C$_9$H$_{19}$ | K83 | G105 C112 A130 I |
| 37298 | C$_4$H$_9$— | —C$_9$H$_{19}$ | K72 | G110 C119 A142 I |

| No | L | R | Cr | LC |
|---|---|---|---|---|
| 26651 | C$_8$H$_{17}$—O— | —O—C$_8$H$_{17}$ | K? | G259 C339.5 N344 I |
| 26652 | C$_{12}$H$_{25}$—O— | —O—C$_{12}$H$_{25}$ | K? | H235 C308 I |
| 26653 | C$_{16}$H$_{33}$—O— | —O—C$_{16}$H$_{33}$ | K? | H229 F272 C290 I |

TABLE 27

| No | L | R | Cr | LC |
|---|---|---|---|---|
| 26625 | Cl— | —Cl | K298 | C258 N313 I |
| 26628 | C$_4$H$_9$— | —C$_4$H$_9$ | K145 | C166 N244 I |
| 26629 | C$_6$H$_{13}$— | —C$_6$H$_{13}$ | K142 | B135 C194 N225 I |
| 26633 | C$_4$H$_9$—O— | —O—C$_4$H$_9$ | K197.7 | C210.6 N294.2 I |
| 26634 | C$_5$H$_{11}$—O— | —O—C$_5$H$_{11}$ | K179.8 | 1224.1 C270.7 I |
| 26635 | C$_6$H$_{13}$—O— | —O—C$_6$H$_{13}$ | K167.4 | 1232.6 C262.7 I |
| 26636 | C$_7$H$_{15}$—O— | —O—C$_7$H$_{15}$ | K160.7 | 1236.1 C250.3 I |
| 26637 | C$_8$H$_{17}$—O— | —O—C$_8$H$_{17}$ | K153.1 | 1237.1 C244 I |
| 26638 | C$_9$H$_{19}$—O— | —O—C$_9$H$_{19}$ | K147.6 | 1233.7 I |
| 26639 | C$_{10}$H$_{21}$—O— | —O—C$_{10}$H$_{21}$ | K140.6 | 1226.8 I |
| 26640 | C$_{12}$H$_{25}$—O— | —O—C$_{12}$H$_{25}$ | K129 | 1221.1 I |

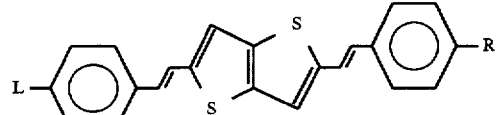

| No | L | R | Cr | LC |
|---|---|---|---|---|
| 43323 | C$_4$H$_9$— | —C$_4$H$_9$ | K319 | S340 A? Z |

TABLE 28

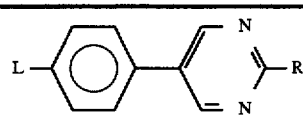

| No | L | R | Cr | LC |
|---|---|---|---|---|
| 3978 | $C_6H_{13}-O-$ | $-S-C_5H_{11}$ | K24 | A71.5 I |
| 3979 | $C_6H_{13}-O-$ | $-S-C_6H_{13}$ | K30 | A74.5 I |
| 3980 | $C_6H_{13}-O-$ | $-S-C_7H_{15}$ | K39.5 | A72.5 I |
| 3981 | $C_6H_{13}-O-$ | $-S-C_8H_{17}$ | K27 | A73 I |
| 3982 | $C_6H_{13}-O-$ | $-S-C_9H_{19}$ | K42.5 | A72 I |
| 3983 | $C_6H_{13}-O-$ | $-S-C_{10}H_{21}$ | K31.5 | A71.5 I |
| 3984 | $C_7H_{15}-O-$ | $-S-CH_3$ | K62.5 | A73 I |
| 3985 | $C_7H_{15}-O-$ | $-S-C_6H_{13}$ | K40 | A74.5 I |
| 3986 | $C_7H_{15}-O-$ | $-S-C_7H_{15}$ | K41 | C42 A73 I |
| 3987 | $C_7H_{15}-O-$ | $-S-C_{10}H_{21}$ | K53 | A71 I |
| 3988 | $C_7H_{15}-O-$ | $-S-C_{11}H_{23}$ | K61 | A69.5 I |
| 3989 | $C_8H_{17}-O-$ | $-S-C_6H_{13}$ | K47 | A76 I |
| 3990 | $C_8H_{17}-O-$ | $-S-C_7H_{15}$ | K39 | G34 C51 A75 I |
| 3991 | $C_8H_{17}-O-$ | $-S-C_8H_{17}$ | K51 | G40 C55 A75 I |
| 3992 | $C_8H_{17}-O-$ | $-S-C_9H_{19}$ | K47.6 | G40.5 C54.5 A74.1 I |
| 3993 | $C_8H_{17}-O-$ | $-S-C_{10}H_{21}$ | K54.8 | G42.2 C59.7 A74 I |
| 3994 | $C_8H_{17}-O-$ | $-S-C_{11}H_{23}$ | K61.4 | C53.4 A74.5 I |
| 3995 | $C_9H_{19}-O-$ | $-S-CH_3$ | K73 | A77.5 I |
| 3996 | $C_9H_{19}-O-$ | $-S-C_6H_{13}$ | K48 | A76 I |
| 3997 | $C_9H_{19}-O-$ | $-S-C_8H_{17}$ | K52 | G38.1 C58 A75.8 I |
| 3998 | $C_9H_{19}-O-$ | $-S-C_9H_{19}$ | K48.5 | G38.5 C57 A74.8 I |
| 3999 | $C_9H_{19}-O-$ | $-S-C_{10}H_{21}$ | K54.7 | G42.2 C59.7 A73.9 I |
| 4000 | $C_9H_{19}-O-$ | $-S-C_{11}H_{23}$ | K60 | C54.7 A73.4 I |
| 4001 | $C_{10}H_{21}-O-$ | $-S-C_6H_{13}$ | K56 | A76.5 I |
| 4002 | $C_{10}H_{21}-O-$ | $-S-C_9H_{19}$ | K58.8 | G54 C69.3 A75.7 I |
| 4003 | $C_{10}H_{21}-O-$ | $-S-C_{10}H_{21}$ | K62.1 | G57.8 C71 A75 I |
| 4004 | $C_{10}H_{21}-O-$ | $-O-C_{11}H_{23}$ | K62 | 558.6 C70.9 A74.8 I |
| 4005 | $C_{11}H_{23}-O-$ | $-S-C_{10}H_{21}$ | K64.5 | G61.8 C73.9 A75 I |
| 4006 | $C_{11}H_{23}-O-$ | $-O-C_{11}H_{23}$ | K65 | S63 C74.2 A74.7 I |
| 4016 | $C_6H_{13}-S-$ | $-C_6H_{13}$ | K50 | A57.5 I |

TABLE 29

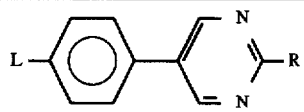

| No | L | R | Cr | LC |
|---|---|---|---|---|
| 4017 | $C_4H_9-S-$ | $-S-C_6H_{13}$ | | K42.5 A42 I |
| 4018 | $C_6H_{13}-S-$ | $-S-C_6H_{13}$ | | K40 A48.5 I |
| 4019 | $CH_3-CMe_2-C_5H_{10}-O-$ | $-C_8H_{17}$ | | K73 C64 A71 W |
| 4020 | $CH_3-CMe_2-C_5H_{10}-O-$ | $-O-C_9H_{19}$ | | K86 C80 A82 W |
| 4021 | $CH_3-CMe_2-C_5H_{10}-O-$ | $-S-C_{10}H_{21}$ | | K60 C53 A55 W |
| 4023 | $C_6H_{13}-O-C_2H_4-O-C_2H_4-O-$ | $-O-C_9H_{19}$ | | K48 A44 I |
| 4028 | $C_5H_{11}-COO-$ | $-C_6H_{13}$ | | K79 B85.5 A95 I |
| 4030 | $C_{10}H_{21}-O-$ | $-O-CH_2-CHMe-C_2H_5$ | S | K63 A69 I |
| 4031 | $C_8H_{17}-$ | $-O-C_3H_6-CHMe-C_2H_5$ | 1 | K51.8 A55 I |
| 4032 | $C_{10}H_{21}-O$ | $-O-C_3H_6-CHMe-C_2H_5$ | 1 | K63 C*57.5 A82 I |
| 4033 | $C_{10}H_{21}-O-$ | $-O-C_2H_4-CHMe-C_3H_6-CHMe-CH_3$ | 1 | K45 C*37 A58 I |
| 4034 | $C_8H_{17}-$ | $-O-C_5H_{10}-CHMe-C_2H_5$ | 1 | K46 C*35 A60 I |
| 4035 | $C_8H_{17}-O-$ | $-C_5H_{10}-CHMe-C_2H_5$ | S | K36 S46 C*55 A71 I |
| 4036 | $C_{10}H_{21}-O-$ | $-O-C_5H_{10}-CHMe-C_2H_5$ | 1 | K77 C*76 A86 I |
| 4037 | $C_8H_{17}-O-$ | $-S-C_5H_{10}-CHMe-C_2H_5$ | S | K55.8 S24 C*55.6 A64.3 I |
| 4041 | $C_5H_{11}-$ | $-S-CF_2-H$ | | K50.8 N-17 E |
| 4042 | $C_{10}H_{21}-O-$ | $-O-C_9H_{18}-CH/CH_2$  $CH_2$ | | K88 S70.6 C84 A87.6 I |
| 4049 | $CH_3-CHMe-CHF-COO-$ | $-O-C_9H_{18}-CH/CH_2$  $CH_2$ | S | K78 A64 I |
| 4051 | $C_2H_5-CHMe-CH_2-O-$ | $-C_8H_{17}$ | 1 | K51 A66 I |
| 4053 | $C_2H_5-CHMe-CH_2-O-$ | $-O-C_{10}H_{21}$ | 1 | K82 A63 I |
| 4055 | $C_2H_5-CHMe-C_3H_6-O-$ | $-C_{12}H_{25}$ | 1 | K46 A62 I |
| 4056 | $C_2H_5-CHMe-C_3H_6-O-$ | $-S-C_8H_{17}$ | 2 | K24 C36 A49.8 I |
| 4058 | $C_2H_5-CHMe-C_5H_{10}-O-$ | $-C_8H_{17}$ | S | K40.2 G*43.4 C*57.8 A72.3 I |
| 4059 | $C_2H_5-CHMe-C_5H_{10}-O-$ | $-C_{12}H_{25}$ | 1 | K57.1 C*58 A68 I |
| 4060 | $C_2H_5-CHMe-C_5H_{10}-O-$ | $-O-C_8H_{17}$ | 1 | K73 C*78 A86 I |
| 4061 | $C_2H_5-CHMe-C_5H_{10}-O-$ | $-O-C_9H_{19}$ | S | K77.7 C*79.2 A84.7 I |
| 4062 | $C_2H_5-CHMe-C_5H_{10}-O-$ | $-S-C_6H_{13}$ | S | K46 C*51.5 A63 I |
| 4063 | $C_2H_5-CHMe-C_5H_{10}-O-$ | $-S-C_7H_{15}$ | S | K44.6 C*52.5 A59.8 I |
| 4064 | $C_2H_5-CMMe-C_5H_{10}-O-$ | $-S-C_8H_{17}$ | 1 | K43 C*55 A60 I |
| 4065 | $C_2H_5-CMMe-C_5H_{10}-O-$ | $-S-C_9H_{19}$ | S | K28.1 C*53.5 A60.5 I |

TABLE 30

TABLE 31

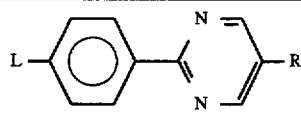

| No | L | R | Cr | LC |
|---|---|---|---|---|
| 4229 | $C_6H_{13}$—OCOO— | —CN | K83 | A96 N121 I |
| 4230 | $C_8H_{17}$—O— | —O—$C_6H_{12}$—$SiMe_3$ | K38.7 | C64.5 I |
| 4231 | $C_8H_{17}$—O— | —O—$C_{11}H_{22}$—$SiMe_3$ | K69.4 | C92 I |
| 4232 | $C_{12}H_{25}$—O— | —O—$C_{11}H_{22}$—$SiMe_3$ | K81.6 | C89.9 I |
| 4233 | $C_8H_{17}$—O— | —O—$C_4H_8$—$SiMe_2C_4H_9$ | K36.4 | A30.6 N30.7 I |
| 4234 | $C_8H_{17}$—O— | —O—$C_6H_{12}$—$SiMe_2Et$ | K28.7 | C56 I |
| 4235 | $C_{12}H_{25}$—O— | —O—$C_{11}H_{22}$—$SiMe_2Et$ | K75.4 | C84.9 I |
| 4236 | $C_5H_{11}$— | —$C_6H_{13}$ | K10 | A26.5 I |
| 4237 | $C_5H_{11}$— | —$C_7H_{15}$ | K30.6 | S47.7 I |
| 4239 | $C_6H_{13}$— | —$C_7H_{15}$ | K21.1 | A47.3 I |
| 4240 | $C_6H_{13}$— | —$C_8H_{17}$ | K20.5 | A48.4 I |
| 4241 | $C_7H_{15}$— | —$C_6H_{13}$ | K15 | A29 I |
| 4242 | $C_7H_{15}$— | —$C_8H_{17}$ | K23.4 | A50.3 I |
| 4243 | $C_7H_{15}$— | —$C_9H_{19}$ | K41.1 | F24 A59.7 I |
| 4244 | $C_7H_{15}$— | —$C_{10}H_{21}$ | K29.8 | F33.8 C43.3 A60.6 I |
| 4245 | $C_7H_{15}$— | —$C_{11}H_{23}$ | K39.2 | F48.4 C53.5 A64.7 I |
| 4246 | $C_7H_{15}$— | —$C_{12}H_{25}$ | K41.4 | F53.8 C58 A65.2 I |
| 4247 | $C_7H_{15}$— | —$C_{14}H_{29}$ | K38.5 | F62.7 A67.2 I |
| 4248 | $C_8H_{17}$— | —$C_6H_{13}$ | K18 | A29.5 I |
| 4249 | $C_8H_{17}$— | —$C_7H_{15}$ | K18.5 | A48.1 I |
| 4250 | $C_8H_{17}$— | —$C_8H_{17}$ | K31.5 | A50.2 I |
| 4251 | $C_8H_{17}$— | —$C_9H_{19}$ | K29 | F24.6 A59.8 I |
| 4252 | $C_8H_{17}$— | —$C_{10}H_{21}$ | K33.6 | F36.7 C46.2 A59.8 I |
| 4253 | $C_8H_{17}$— | —$C_{11}H_{23}$ | K41 | F50.8 C55.4 A64.2 I |
| 4254 | $C_8H_{17}$— | —$C_{12}H_{25}$ | K47.5 | F55.6 C62.2 A64.2 I |
| 4255 | $C_8H_{17}$— | —$C_{14}H_{29}$ | K57.7 | F64.5 C66.3 I |

TABLE 32

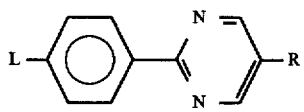

| No | L | R | Cr | LC |
|---|---|---|---|---|
| 4256 | $C_8H_{17}$— | —$C_{16}H_{33}$ | K56 | F67 I |
| 4257 | $C_9H_{19}$— | —$C_6H_{13}$ | K23.5 | A30.5 N33 I |
| 4258 | $C_9H_{19}$— | —$C_8H_{17}$ | K27.3 | A51.2 I |
| 4259 | $C_9H_{19}$— | —$C_{10}H_{21}$ | K32.5 | F36.5 C44 A60.7 I |
| 4260 | $C_9H_{19}$— | —$C_{12}H_{25}$ | K41 | F56.8 C63.2 A65.6 I |
| 4261 | $C_{10}H_{21}$— | —$C_6H_{13}$ | K31 | A29.3 N31 I |
| 4262 | $C_{10}H_{21}$— | —$C_8H_{17}$ | K35.5 | A49.7 I |
| 4263 | $C_{10}H_{21}$— | —$C_{10}H_{21}$ | K46.3 | C45 A59.8 I |
| 4264 | $C_{10}H_{21}$— | —$C_{11}H_{23}$ | K41.2 | F52.6 C54.8 A64.6 I |
| 4265 | $C_{10}H_{21}$— | —$C_{12}H_{25}$ | K48.8 | F58 C64 A65 I |
| 4266 | $C_{12}H_{25}$— | —$C_8H_{17}$ | K46.8 | A48.3 I |
| 4267 | $C_{12}H_{25}$— | —$C_{11}H_{23}$ | K52.9 | F52.2 A63.6 I |
| 4268 | $C_{12}H_{25}$— | —$C_{12}H_{25}$ | K59.9 | F59.7 C64 A64.7 I |
| 4269 | $C_4H_9$— | —O—$C_6H_{13}$ | K42 | A72 I |
| 4271 | $C_6H_{13}$— | —O—$C_4H_9$ | K40 | A56.5 N60.5 I |
| 4272 | $C_6H_{13}$— | —O—$C_5H_{11}$ | K48 | A62 I |
| 4273 | $C_6H_{13}$— | —O—$C_6H_{13}$ | K49 | A77 I |
| 4274 | $C_6H_{13}$— | —O—$C_7H_{15}$ | K32.5 | C50.6 A76.6 I |
| 4275 | $C_6H_{13}$— | —O—$C_8H_{17}$ | K29 | C68 A85 I |
| 4276 | $C_6H_{13}$— | —O—$C_9H_{19}$ | K47.7 | C77.2 A83.6 I |
| 4277 | $C_6H_{13}$— | —O—$C_{10}H_{21}$ | K38 | S35 C82 A87 I |
| 4278 | $C_6H_{13}$— | —O—$C_{11}H_{23}$ | K38.8 | S42.3 C84.3 A86.4 I |
| 4279 | $C_6H_{13}$— | —O—$C_{12}H_{25}$ | K35 | S47.4 C85.6 A87.1 I |
| 4280 | $C_6H_{13}$— | —O—$C_{14}H_{29}$ | K34.4 | S54.9 C85.2 A86.6 I |
| 4281 | $C_6H_{13}$— | —O—$C_{15}H_{31}$ | K49.9 | S56.7 C83.3 A85.2 I |
| 4283 | $C_7H_{15}$— | —O—$C_5H_{11}$ | K46 | A64 N66 I |
| 4284 | $C_7H_{15}$— | —O—$C_6H_{13}$ | K51 | A78 I |
| 4285 | $C_7H_{15}$— | —O—$C_7H_{15}$ | K32.2 | C45 A77.5 I |

TABLE 33

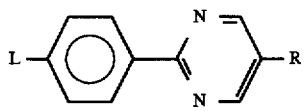

| No | L | R | Cr | LC |
|---|---|---|---|---|
| 4286 | $C_7H_{15}-$ | $-O-C_8H_{17}$ | K32 | C64 A87 I |
| 4287 | $C_7H_{15}-$ | $-O-C_9H_{19}$ | K34.2 | C76.3 A85.1 I |
| 4288 | $C_7H_{15}-$ | $-O-C_{10}H_{21}$ | K32 | S33 C83 A88 I |
| 4289 | $C_7H_{15}-$ | $-O-C_{11}H_{23}$ | K38.7 | S45.2 C86.8 A88.6 I |
| 4290 | $C_7H_{15}-$ | $-O-C_{12}H_{25}$ | K46 | S54 C88 A89 I |
| 4292 | $C_8H_{17}-$ | $-O-C_5H_{11}$ | K47 | A61 I |
| 4293 | $C_8H_{17}-$ | $-O-C_6H_{13}$ | K46 | A76 I |
| 4294 | $C_8H_{17}-$ | $-O-C_7H_{15}$ | K46.5 | C39 A77.5 I |
| 4295 | $C_8H_{17}-$ | $-O-C_8H_{17}$ | K39 | C58 A84 I |
| 4296 | $C_8H_{17}-$ | $-O-C_9H_{19}$ | K40.5 | C76 A84.6 I |
| 4297 | $C_8H_{17}-$ | $-O-C_{10}H_{21}$ | K42 | C84 A88 I |
| 4298 | $C_8H_{17}-$ | $-O-C_{11}H_{23}$ | K54.3 | C87.2 I |
| 4299 | $C_8H_{17}-$ | $-O-C_{12}H_{25}$ | K57 | S58 C89 I |
| 4300 | $C_8H_{17}-$ | $-O-C_{14}H_{29}$ | K59.8 | S67.2 C88.3 I |
| 4301 | $C_8H_{17}-$ | $-O-C_{15}H_{31}$ | K57.9 | S69.6 C87.5 I |
| 4303 | $C_9H_{19}-$ | $-O-C_5H_{11}$ | K49 | A62 N63 I |
| 4304 | $C_9H_{19}-$ | $-O-C_6H_{13}$ | K48 | A77 I |
| 4305 | $C_9H_{19}-$ | $-O-C_7H_{15}$ | K40 | A78 I |
| 4306 | $C_9H_{19}-$ | $-O-C_8H_{17}$ | K36 | C53 A85 I |
| 4307 | $C_9H_{19}-$ | $-O-C_9H_{19}$ | K39 | C73.9 A84.9 I |
| 4308 | $C_9H_{19}-$ | $-O-C_{10}H_{21}$ | K37 | 532 C83 A87 I |
| 4309 | $C_9H_{19}-$ | $-O-C_{11}H_{23}$ | K45 | S46 C87 I |
| 4310 | $C_9H_{19}-$ | $-O-C_{12}H_{25}$ | K47 | S59 C89 I |
| 4311 | $C_{10}H_{21}-$ | $-O-C_9H_{19}$ | K46.6 | C71.4 A83.8 I |
| 4312 | $C_{10}H_{21}-$ | $-O-C_{11}H_{23}$ | K51.4 | S47 C86.5 I |
| 4326 | $C_8H_{17}-$ | $-OOC-C_7H_{15}$ | K79.4 | A74.4 I |
| 4334 | $C_3H_7-O-C_5H_{10}-$ | $-O-C_8H_{17}$ | K8 | C47 A69 I |
| 4335 | $C_3H_7-O-C_5H_{10}-$ | $-OOC-C_7H_{15}$ | K70 | |

TABLE 34

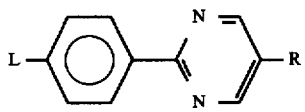

| No | L | R | Cr | LC |
|---|---|---|---|---|
| 4336 | $C_6H_{13}-O-CHMe-$ | $-O-C_{10}H_{21}$ | 1 K<-40 | C*-40 A-23 I |
| 4337 | $C_2H_5-O-CHMe-C_5H_{10}$ | $-O-C_6H_{13}$ | 1 K-22 | C*-21 A48 I |
| 4338 | $C_2H_5-O-CHMe-C_5H_{10}$ | $-O-C_8H_{17}$ | 1 K? | S8 C*49 A55 I |
| 4339 | $C_2H_5-O-CHMe-C_5H_{10}$ | $-O-C_{10}H_{21}$ | 1 K? | S10 C*55 I |
| 4340 | $C_2H_5-O-CHMe-C_5H_{10}$ | $-O-C_{11}H_{23}$ | 1 K27 | C*56 I |
| 4341 | $C_2H_5-CHMe-C_5H_{10}$ | $-O-C_{12}H_{25}$ | 1 K13 | C*56 I |
| 4342 | $C_3H_7-O-CHMe-C_5H_{10}$ | $-O-C_8H_{17}$ | 1 K? | S-6 C*46 A52 I |
| 4343 | $C_5H_{11}-O-CHMe-C_5H_{10}$ | $-O-C_8H_{17}$ | 1 K? | S-4 C*37 A44 I |
| 4346 | $CH_3-O-$ | $-C_9H_{19}$ | K40 | S31 N41 I |
| 4349 | $C_2H_5-O-$ | $-C_8H_{17}$ | K42.5 | A43.5 N58.5 I |
| 4353 | $C_3H_7-O-$ | $-C_7H_{15}$ | K42 | A43.5 N52 I |
| 4354 | $C_3H_7-O-$ | $-C_8H_{17}$ | K45 | A49.5 I |
| 4358 | $C_4H_9-O-$ | $-C_7H_{15}$ | K40.5 | A42 N64 I |
| 4359 | $C_4H_9-O-$ | $-C_8H_{17}$ | K35 | A53.5 N60 I |
| 4363 | $C_5H_{11}-O-$ | $-C_7H_{15}$ | K49 | C48.5 A52 N66 I |
| 4364 | $C_5H_{11}-O-$ | $-C_8H_{17}$ | K38 | A54 N58 I |
| 4365 | $C_5H_{11}-O-$ | $-C_9H_{19}$ | K41 | A65.5 I |
| 4366 | $C_5H_{11}-O-$ | $-C_{10}H_{21}$ | K47.5 | A67 I |

TABLE 35

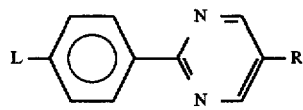

| No | L | R | Cr | LC |
|---|---|---|---|---|
| 4370 | C₆H₁₃—O— | —C₇H₁₅ | K45.5 | A33 N69.5 I |
| 4371 | C₆H₁₃—O— | —C₈H₁₇ | K27.5 | C44.5 A57.5 N65 I |
| 4372 | C₆H₁₃—O— | —C₉H₁₉ | K33.5 | C49.5 A71 N71.5 I |
| 4373 | C₆H₁₃—O— | —C₁₀H₂₁ | K32.5 | C62 A74.5 I |
| 4377 | C₇H₁₅—O— | —C₇H₁₅ | K44 | C44 A49 N68 I |
| 4378 | C₇H₁₅—O— | —C₈H₁₇ | K46 | C49 A61 N66 I |
| 4379 | C₇H₁₅—O— | —C₉H₁₉ | K35 | C51.5 A71.5 I |
| 4380 | C₇H₁₅—O— | —C₁₀H₂₁ | K46 | C62.5 A72 I |
| 4384 | C₈H₁₇—O— | —C₇H₁₅ | K49 | A44 N69.5 I |
| 4385 | C₈H₁₇—O— | —C₈H₁₇ | K35 | C57 A64 N70 I |
| 4386 | C₈H₁₇—O— | —C₉H₁₉ | K33 | C60 A74.5 I |
| 4387 | C₈H₁₇—O— | —C₁₀H₂₁ | K37 | C68.5 A73.5 I |
| 4391 | C₉H₁₉—O— | —C₇H₁₅ | K48 | C51 A57 N70 I |
| 4392 | C₉H₁₉—O— | —C₈H₁₇ | K33 | C56 A65 N68.5 I |
| 4393 | C₉H₁₉—O— | —C₉H₁₉ | K34 | C61 A75 I |
| 4394 | C₉H₁₉—O— | —C₁₁H₂₃ | K45 | C78 A80 I |
| 4397 | C₁₀H₂₁—O— | —C₇H₁₅ | K53 | A54.5 N71.5 I |

TABLE 36

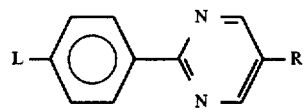

| No | L | R | Cr | LC |
|---|---|---|---|---|
| 4398 | C₁₀H₂₁—O— | —C₈H₁₇ | K32 | C59.5 A65.5 N69.5 I |
| 4399 | C₁₀H₂₁—O— | —C₁₀H₂₁ | K41 | C74 A77 I |
| 4401 | C₁₁H₂₃—O— | —C₇H₁₅ | K55 | C54.5 A62.5 N70 I |
| 4402 | C₁₁H₂₃—O— | —C₈H₁₇ | K44.5 | C60 A67 N69 I |
| 4405 | C₁₂H₂₅—O— | —C₇H₁₅ | K59.5 | C57.5 A63 N71 I |
| 4406 | C₁₂H₂₅—O— | —C₈H₁₇ | K42 | C61.5 A68.5 N70 I |
| 4408 | C₁₀H₂₁—O— | —C₅H₁₀—CHMe—O—C₂H₅ 1 | K43 | C*13 N*27 I |
| 4409 | C₃H₇—O— | —O—C₇H₁₅ | K68.6 | C65 A78.7 N83.6 I |
| 4410 | C₃H₇—O— | —O—C₈H₁₇ | K49.8 | C70.5 A88.2 N88.7 I |
| 4411 | C₃H₇—O— | —O—C₉H₁₉ | K43.7 | C72 A89.4 I |
| 4412 | C₃H₇—O— | —O—C₁₀H₂₁ | K45.6 | C71 A92.6 I |
| 4413 | C₃H₇—O— | —O—C₁₁H₂₃ | K41.9 | C68 A93 I |
| 4414 | C₃H₇—O— | —O—C₁₂H₂₅ | K43.4 | C61.6 A94.1 I |
| 4415 | C₄H₉—O— | —O—C₇H₁₅ | K53.4 | C75.1 A82.4 N92.1 I |
| 4416 | C₄H₉—O— | —O—C₈H₁₇ | K54.4 | C84 A94.7 N96.6 I |
| 4417 | C₄H₉—O— | —O—C₉H₁₉ | K44.4 | C87.7 A96.6 I |
| 4418 | C₄H₉—O— | —O—C₁₀H₂₁ | K41.8 | C90 A99.4 I |
| 4419 | C₄H₉—O— | —O—C₁₁H₂₃ | K42.3 | C89 A99.8 I |
| 4420 | C₄H₉—O— | —O—C₁₂H₂₅ | K41.8 | C88.4 A101 I |
| 4422 | C₅H₁₁—O— | —O—C₆H₁₃— | K62 | C65.9 A76.6 N92.7 I |
| 4423 | C₅H₁₁—O— | —O—C₇H₁₅ | K54.4 | C77.4 A84.2 N91.3 I |
| 4424 | C₅H₁₁—O— | —O—C₈H₁₇ | K50.2 | C85.9 A93.9 N94.8 I |
| 4425 | C₅H₁₁—O— | —O—C₉H₁₉ | K66.7 | C90 A95 I |
| 4426 | C₅H₁₁—O— | —O—C₁₀H₂₁ | K41.4 | C93.9 A97.2 I |
| 4427 | C₅H₁₁—O— | —O—C₁₁H₂₃ | K51.4 | C95.9 A98.2 I |
| 4428 | C₅H₁₁—O— | —O—C₁₂H₂₅ | K41.7 | C96.2 A98.6 I |

TABLE 37

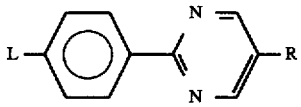

| No | L | R | Cr | LC |
|---|---|---|---|---|
| 4429 | C₆H₁₃—O— | —O—C₆H₁₃ | K62 | A68 N69 I |
| 4430 | C₆H₁₃—O— | —O—C₇H₁₅ | K45.8 | C80.6 A84.7 N94.9 I |
| 4431 | C₆H₁₃—O— | —O—C₈H₁₇ | K42.6 | C89.8 A96.6 N98.7 I |
| 4432 | C₆H₁₃—O— | —O—C₉H₁₉ | K49.9 | C94.4 A97.9 I |
| 4433 | C₆H₁₃—O— | —O—C₁₀H₂₁ | K43.8 | C98.7 A100.3 I |
| 4434 | C₆H₁₃—O— | —O—C₁₁H₂₃ | K55.4 | C100.4 A101 I |
| 4435 | C₆H₁₃—O— | —O—C₁₂H₂₅ | K52.2 | C102.2 I |
| 4436 | C₇H₁₅—O— | —O—C₆H₁₃ | K60.8 | C68.2 A79.4 N94.6 I |

TABLE 37-continued

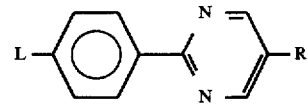

| No | L | R | Cr | LC |
|---|---|---|---|---|
| 4437 | C₇H₁₅—O— | —O—C₇H₁₅ | K59.2 | C79.9 A87.6 N93.6 I |
| 4438 | C₇H₁₅—O— | —O—C₈H₁₇ | K51.6 | C87.2 A96.4 N97.1 I |
| 4439 | C₇H₁₅—O— | —O—C₉H₁₉ | K56 | C94.9 A97.8 I |
| 4440 | C₇H₁₅—O— | —O—C₁₀H₂₁ | K55.6 | C99.6 A100.3 I |
| 4441 | C₇H₁₅—O— | —O—C₁₁H₂₃ | K67.4 | C100.1 I |
| 4442 | C₇H₁₅—O— | —O—C₁₂H₂₅ | K54.8 | C100.3 I |
| 4444 | C₈H₁₇—O— | —O—C₆H₁₃ | K59.3 | C73 A80 N96.2 I |
| 4445 | C₈H₁₇—O— | —O—C₇H₁₅ | K53.4 | C81.5 A88.3 N95.4 I |
| 4446 | C₈H₁₇—O— | —O—C₈H₁₇ | K51 | C92.3 A99.5 N100.3 I |
| 4447 | C₈H₁₇—O— | —O—C₉H₁₉ | K48.2 | C96.4 A99 I |
| 4448 | C₈H₁₇—O— | —O—C₁₀H₂₁ | K51.7 | C101.7 A102.1 I |
| 4449 | C₈H₁₇—O— | —O—C₁₁H₂₃ | K59.9 | C101.7 I |
| 4450 | C₈H₁₇—O— | —O—C₁₂H₂₅ | K57.1 | C102.9 I |
| 4451 | C₉H₁₉—O— | —O—C₆H₁₃ | K61.6 | C68.9 A83.2 N93.7 I |
| 4452 | C₉H₁₉—O— | —O—C₇H₁₅ | K55.2 | C78.7 A89.6 N93.6 I |
| 4453 | C₉H₁₉—O— | —O—C₈H₁₇ | K55.1 | C87.5 A96.2 I |
| 4454 | C₉H₁₉—O— | —O—C₉H₁₉ | K65 | C97 A101 I |

TABLE 37-continued

L—⟨phenyl⟩—⟨pyrimidine⟩—R

| No | L | R | Cr | LC |
|---|---|---|---|---|
| 4455 | $C_9H_{19}-O-$ | $-O-C_{10}H_{21}$ | K52.5 | C101.1 I |
| 4456 | $C_9H_{19}-O-$ | $-O-C_{11}H_{23}$ | K62 | C101 I |
| 4457 | $C_9H_{19}-O-$ | $-O-C_{12}H_{25}$ | K60.3 | C100.3 I |
| 4458 | $C_{10}H_{21}-O-$ | $-O-C_6H_{13}$ | K62.3 | C71.6 A83.8 N93.6 I |

TABLE 38

L—⟨phenyl⟩—⟨pyrimidine⟩—R

| No | L | R | Cr | LC |
|---|---|---|---|---|
| 4459 | $C_{10}H_{21}-O-$ | $-O-C_7H_{15}$ | K50.4 | C79.7 A90.1 N93.6 I |
| 4460 | $C_{10}H_{21}-O-$ | $-O-C_8H_{17}$ | K50 | C89 A99.6 I |
| 4461 | $C_{10}H_{21}-O-$ | $-O-C_9H_{19}$ | K52.3 | C96.2 A99 I |
| 4462 | $C_{10}H_{21}-O-$ | $-O-C_{10}H_{21}$ | K52.7 | C101.4 I |
| 4463 | $C_{10}H_{21}-O-$ | $-O-C_{11}H_{23}$ | K62.9 | C101.2 I |
| 4464 | $C_{10}H_{21}-O-$ | $-O-C_{12}H_{25}$ | K65.4 | C102.8 I |
| 4465 | $C_{10}H_{21}-O-$ | $-O-C_{14}H_{29}$ | K67 | C103 I |
| 4466 | $C_{11}H_{23}-O-$ | $-O-C_6H_{13}$ | K69.3 | C69 A86.2 N91.8 I |
| 4467 | $C_{11}H_{23}-O-$ | $-O-C_7H_{15}$ | K58.2 | C77 A90.1 N91.9 I |
| 4468 | $C_{11}H_{23}-O-$ | $-O-C_8H_{17}$ | K56 | C84.9 A97.1 I |
| 4469 | $C_{11}H_{23}-O-$ | $-O-C_9H_{18}$ | K56.2 | C92.7 A96.1 I |
| 4470 | $C_{11}H_{23}-O-$ | $-O-C_{10}H_{21}$ | K53.1 | C100.6 I |
| 4471 | $C_{11}H_{23}-O-$ | $-O-C_{11}H_{23}$ | K69.8 | C99.8 I |
| 4472 | $C_{11}H_{23}-O-$ | $-O-C_{12}H_{25}$ | K65.6 | C101 I |
| 4473 | $C_{11}H_{23}-O-$ | $-O-C_{16}H_{33}$ | K71.3 | S75.6 C100.9 I |
| 4474 | $C_{12}H_{25}-O-$ | $-O-C_6H_{13}$ | K70.3 | C70.7 A86.2 N91.4 I |
| 4475 | $C_{12}H_{25}-O-$ | $-O-C_7H_{15}$ | K57.1 | C77.2 A89.4 N90.9 I |
| 4476 | $C_{12}H_{25}-O-$ | $-O-C_8H_{17}$ | K50 | C86 A98 I |
| 4477 | $C_{12}H_{25}-O-$ | $-O-C_9H_{19}$ | K53.8 | C93.5 A96.9 I |
| 4478 | $C_{12}H_{25}-O-$ | $-O-C_{10}H_{21}$ | K54.6 | C100.3 I |
| 4479 | $C_{12}H_{25}-O-$ | $-O-C_{11}H_{23}$ | K59.5 | C100.7 I |
| 4480 | $C_{12}H_{25}-O-$ | $-O-C_{12}H_{25}$ | K63.7 | C104.3 I |
| 4481 | $C_{12}H_{25}-O-$ | $-O-C_{16}H_{33}$ | K71.2 | S73.7 C99 I |
| 4484 | $C_8H_{17}-O-$ | $-O-C_4H_8-CMe_2-C_4H_9$ | K54 | C34 N37 I |
| 4485 | $C_8H_{17}-O-$ | $-O-C_6H_{12}-CMe_2-C_4H_9$ | K43 | C55 I |
| 4498 | $C_7H_{15}-O-$ | $-OOC-C_6H_{13}$ | K64.9 | C66.2 N85.8 I |
| 4499 | $C_7H_{15}-O-$ | $-OOC-C_9H_{19}$ | K74.8 | C96.5 I |
| 4500 | $C_7H_{15}-O-$ | $-OOC-C_{13}H_{27}$ | K81 | S73 C101 I |
| 4501 | $C_8H_{17}-O-$ | $-OOC-C_6H_{13}$ | K63.4 | C69.7 N89.7 I |
| 4502 | $C_8H_{17}-O-$ | $-OOC-C_7H_{15}$ | K75 | C74.4 N91.3 I |

TABLE 39

L—⟨phenyl⟩—⟨pyrimidine⟩—R

| No | L | R | Cr | LC |
|---|---|---|---|---|
| 4614 | $C_7H_{15}-COO-$ | $-C_7H_{15}$ | K54 | A40 N57 I |
| 4615 | $C_7H_{15}-COO-$ | $-C_8H_{17}$ | K51 | C52 A54 N56 I |
| 4616 | $C_7H_{15}-COO-$ | $-C_9H_{19}$ | K53 | C64 A65 I |
| 4619 | $C_8H_{17}-COO-$ | $-C_8H_{17}$ | K49 | C53.5 A54.8 N56.5 I |

TABLE 39-continued

L—⌬—pyrimidine—R

| No | L | R | | Cr | LC |
|---|---|---|---|---|---|
| 4620 | $C_8H_{17}$—COO— | —$C_{10}H_{21}$ | | K53 | S50 C70 I |
| 4623 | $C_9H_{19}$—COO— | —$C_8H_{17}$ | | K42 | C55.5 N59.8 I |
| 4626 | $C_{10}H_{21}$—COO— | —$C_8H_{17}$ | | K57 | C56.5 A56.7 N59 I |
| 4629 | $C_{11}H_{23}$—COO— | —$C_8H_{17}$ | | K56 | C57.5 N60.8 I |
| 4630 | $C_7H_{15}$—COO— | —O—$C_8H_{17}$ | | K73 | C89 A92 N93 I |
| 4636 | $C_4H_9$—$CMe_2$—$CH_2$—COO— | —O—$C_8H_{17}$ | | K53 | C49 N50 I |
| 4637 | $C_6H_{13}$—$CMe_2$—$CH_2$—COO— | —O—$C_8H_{17}$ | | K45 | C42 N46 I |
| 4643 | $C_5H_{11}$—OCOO— | —$C_{12}H_{25}$ | | K48 | A52 |
| 4645 | $C_9H_{19}$—OCOO— | —$C_{12}H_{25}$ | | K46 | C59 I |
| 4647 | $C_{12}H_{25}$—OCOO— | —$C_{12}H_{25}$ | | K57 | C60 I |
| 4661 | $C_8H_{17}$—O— | —$C_3H_6$—CHMe—$C_2H_5$ | 1 | K33.5 | N*19U |
| 4662 | $C_9H_{19}$—O— | —$C_3H_6$—CHMe—$C_2H_5$ | 1 | K35 | N*20U |
| 4663 | $C_{10}H_{21}$—O— | —$C_3H_6$—CHMe—$C_2H_5$ | 1 | K38 | N*21.5U |
| 4664 | $C_{12}H_{25}$—O— | —$C_3H_6$—CHMe—$C_2H_5$ | 1 | K43.5 | N*40.5U |
| 4665 | $C_8H_{17}$— | —O—$C_5H_{10}$—CHMe—$C_2H_5$ | 1 | K-13 | S10 S18 C*51 A51.4 I |
| 4666 | $C_8H_{17}$— | —O—$C_5H_{10}$—CHMe—$C_2H_5$ | 2 | K16 | C57.5 A59 I |

TABLE 40

L—⌬—pyrimidine—R

| No | L | R | | Cr | LC |
|---|---|---|---|---|---|
| 4697 | $C_8H_{17}$—O— | —O—$CH_2$—CHF—$C_8H_{17}$ | 1 | K62.5 | C*92 A97 I |
| 4698 | $C_9H_{19}$—O— | —O—$CH_2$—CHF—$C_6H_{13}$ | 1 | K61 | C*90.3 A96.2 I |
| 4699 | $C_{10}H_{21}$—O— | —O—$CH_2$—CHF—$C_6H_{13}$ | 1 | K47 | C*90 A97 I |
| 4700 | $C_{12}H_{25}$—O— | —O—$CH_2$—CHF—$C_6H_{13}$ | 1 | K66 | C*89 A96 I |
| 4701 | $C_8H_{17}$— | —$C_2H_4$—CHF—$C_6H_{13}$ | 1 | K31 | C*25 A62 I |
| 4702 | $C_8H_{17}$—O— | —$C_2H_4$—CHF—$C_6H_{13}$ | S | K74 | A82 I |
| 4703 | $C_{10}H_{21}$—O— | —$C_2H_4$—CHF—$C_6H_{13}$ | 1 | K71 | C*69 A82 I |
| 4704 | $C_{10}H_{21}$—O— | —$C_2H_4$—CHF—$C_8H_{17}$ | S | K85 | C*84 A86 I |
| 4705 | $C_{12}H_{25}$—O— | —$C_2H_4$—CHF—$C_6H_{13}$— | S | K74 | A82 I |
| 4706 | $C_{10}H_{21}$—O— | —O—$C_2H_4$—CHF—$C_6H_{13}$ | 1 | K50 | C*96 N*97 I |
| 4707 | $C_{10}H_{21}$—O— | —O—$C_3H_6$—CHF—$C_6H_{13}$ | 1 | K61 | C*102 A103 I |
| 4715 | $C_3H_7$—O—$C_5H_{10}$ | —OOC—CH=CH—$C_7H_{15}$ | | K63 | C61 N69 I |
| 4716 | $C_3H_7$—O—$C_5H_{10}$ | —OOC—CH=CH—$C_8H_{17}$ | | K53 | C62 A64 N68 I |
| 4717 | $C_3H_7$—O—$C_5H_{10}$ | —OOC—CH=CH—$C_9H_{19}$ | | K63 | C73 I |
| 4718 | $C_6H_{13}$— | —O—$CH_2$—CH=CH—$C_2H_5$ | | K57 | A63 I |
| 4719 | $C_6H_{13}$— | —O—$CH_2$—CH=CH—$C_3H_7$ | | K67 | A76 I |
| 4720 | $C_6H_{13}$— | —O—$CH_2$—CH=CH—$C_4H_9$ | | K62 | C65 A71 I |
| 4721 | $C_6H_{13}$— | —O—$CH_2$—CH=CH—$C_5H_{11}$ | | K61 | C76 A80 I |
| 4722 | $C_6H_{13}$— | —O—$CH_2$—CH=CH—$C_6H_{13}$ | | K74 | C78 I |
| 4723 | $C_6H_{13}$— | —O—$CH_2$—CH=CH—$C_7H_{15}$ | | K65 | C82 I |
| 4724 | $C_6H_{13}$— | —O—$CH_2$—CH=CH—$C_8H_{17}$ | | K73 | C82 I |
| 4725 | $C_6H_{13}$— | —O—$CH_2$—CH=CH—$C_9H_{19}$ | | K56 | S72 C84 I |
| 4726 | $C_7H_{15}$— | —O—$CH_2$—CH=CH—$C_2H_5$ | | K53 | A66 I |
| 4727 | $C_7H_{15}$— | —O—$CH_2$—CH=CH—$C_3H_7$ | | K69 | A78 I |
| 4728 | $C_7H_{15}$— | —O—$CH_2$—CH=CH—$C_4H_9$ | | K60 | C61 A73 I |
| 4729 | $C_7H_{15}$— | —O—$CH_2$—CH=CH—$C_5H_{11}$ | | K59 | C75 A82 I |
| 4730 | $C_7H_{15}$— | —O—$CH_2$—CH=CH—$C_6H_{13}$— | | K67 | C80 I |

TABLE 41

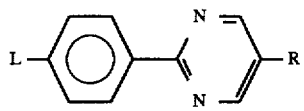

| No | L | R | Cr | LC |
|---|---|---|---|---|
| 4731 | C$_7$H$_{15}$— | —O—CH$_2$—CH=CH—C$_7$H$_{15}$ | K64 | C86 I |
| 4732 | C$_7$H$_{15}$— | —O—CH$_2$—CH=CH—C$_8$H$_{17}$ | K72 | C85 I |
| 4733 | C$_7$H$_{15}$— | —O—CH$_2$—CH=CH—C$_9$H$_{19}$ | K67 | S74 C87 I |
| 4734 | C$_8$H$_{17}$— | —O—CH$_2$—CH=CH—C$_2$H$_5$ | K53 | A65 I |
| 4735 | C$_8$H$_{17}$— | —O—CH$_2$—CH=CH—C$_3$H$_7$ | K68 | A77 I |
| 4736 | C$_8$H$_{17}$— | —O—CH$_2$—CH=CH—C$_4$H$_9$ | K57 | A73 I |
| 4737 | C$_8$H$_{17}$— | —O—CH$_2$—CH=CH—C$_5$H$_{11}$ | K56 | C69.5 A81 I |
| 4738 | C$_8$H$_{17}$— | —O—CH$_2$—CH=CH—C$_6$H$_{13}$ | K67 | C79 I |
| 4739 | C$_8$H$_{17}$— | —O—CH$_2$—CH=CH—C$_7$H$_{15}$ | K39 | S62 C84 I |
| 4740 | C$_8$H$_{17}$— | —O—CH$_2$—CH=CH—C$_8$H$_{17}$ | K51 | S67 C85 I |
| 4741 | C$_8$H$_{17}$— | —O—CH$_2$—CH=CH—C$_9$H$_{19}$ | K66 | S74 C86 I |
| 4742 | C$_9$H$_{19}$— | —O—CH$_2$—CH=CH—C$_2$H$_5$ | K57 | A66 I |
| 4743 | C$_9$H$_{19}$— | —O—CH$_2$—CH=CH—C$_3$H$_7$ | K70 | A77 I |
| 4744 | C$_9$H$_{19}$— | —O—CH$_2$—CH=CH—C$_4$H$_9$ | K57 | C48 A73 I |
| 4745 | C$_9$H$_{19}$— | —O—CH$_2$—CH=CH—C$_5$H$_{11}$ | K56 | C65 A82 I |
| 4746 | C$_9$H$_{19}$— | —O—CH$_2$—CH=CH—C$_6$H$_{13}$ | K62 | C78 A80 I |
| 4747 | C$_9$H$_{19}$— | —O—CH$_2$—CH=CH—C$_7$H$_{15}$ | K60 | S58 C84 I |
| 4748 | C$_9$H$_{19}$— | —O—CH$_2$—CH=CH—C$_8$H$_{17}$ | K50 | S63 C86 I |
| 4749 | C$_9$H$_{19}$— | —O—CH$_2$—CH=CH—C$_9$H$_{19}$ | K61 | S74 C87 I |
| 4750 | C$_3$H$_7$—O—C$_5$H$_{10}$— | O—CH$_2$—CH=CH—C$_3$H$_7$ | K47 | A56 I |
| 4751 | C$_3$H$_7$—O—C$_5$H$_{10}$— | O—CH$_2$—CH=CH—C$_4$H$_9$ | K20 | A41 I |
| 4752 | C$_3$H$_7$—O—C$_5$H$_{10}$— | —O—CH$_2$—CH=CH—C$_5$H$_{11}$ | K36 | C58 A63 I |
| 4753 | C$_3$H$_7$—O—C$_5$H$_{10}$— | —O—CH$_2$—CH=CH—C$_6$H$_{13}$ | K51 | C60 I |
| 4754 | C$_3$H$_7$—O—C$_5$H$_{10}$— | —O—CH$_2$—CH=CH—C$_7$H$_{15}$ | K44 | C65 I |
| 4755 | C$_3$H$_7$—O—C$_5$H$_{10}$— | —O—CH$_2$—CH=CH—C$_8$H$_{17}$ | K50 | S49 C68 I |
| 4756 | C$_3$H$_7$—O—C$_5$H$_{10}$— | —O—CH$_2$—CH=CH—C$_9$H$_{19}$ | K53 | S59 C71 I |
| 4760 | C$_6$H$_{13}$— | —O—C$_3$H$_6$—CH=CH$_2$ | K39 | A69 I |
| 4761 | C$_6$H$_{13}$— | —O—C$_3$H$_6$—CH=CH—C$_3$H$_7$ | K57 | C68 A80 I |
| 4762 | C$_7$H$_{15}$— | —O—C$_3$H$_6$—CH=CH$_2$ | K48 | A72 I |

TABLE 42

| No | L | R | Cr | LC |
|---|---|---|---|---|
| 4763 | C$_7$H$_{15}$— | —O—C$_3$H$_6$—CH=CH—C$_3$H$_7$ | K57 | C66 A82 I |
| 4764 | C$_8$H$_{17}$— | —O—C$_3$H$_6$—CH=CH$_2$ | K43 | A69 I |
| 4765 | C$_8$H$_{17}$— | —O—C$_3$H$_6$—CH=CH—C$_3$H$_7$ | K53 | C55 A82 I |
| 4766 | C$_9$H$_{19}$— | —O—C$_3$H$_6$—CH=CH$_2$ | K50 | A70 I |
| 4767 | C$_9$H$_{19}$— | —O—C$_3$H$_6$—CH=CH—C$_3$H$_7$ | K47 | C52 A82 I |
| 4769 | C$_6$H$_{13}$— | —O—C$_4$H$_8$—CH=CH$_2$ | K35 | A64 I |
| 4770 | C$_7$H$_{15}$— | —O—C$_4$H$_8$—CH=CH$_2$ | K37 | A67 I |
| 4771 | C$_8$H$_{17}$— | —O—C$_4$H$_8$—CH=CH$_2$ | K33 | A64 I |
| 4772 | C$_9$H$_{19}$— | —O—C$_4$H$_8$—CH=CH$_2$ | K33 | A65 I |
| 4774 | C$_3$H$_7$—O—C$_5$H$_{10}$— | —O—C$_4$H$_8$—CH=CH$_2$ | K18 | A55 I |
| 4776 | C$_6$H$_{13}$— | —O—C$_5$H$_{10}$—CH=CH$_2$ | K34 | A79 I |
| 4777 | C$_6$H$_{13}$— | —O—C$_5$H$_{10}$—CH=CH—CH$_3$ | K45 | C50 A85 I |
| 4778 | C$_7$H$_{15}$— | —O—C$_5$H$_{10}$—CH=CH$_2$ | K35 | A81 I |
| 4779 | C$_7$H$_{15}$— | —O—C$_5$H$_{10}$—CH=CH—CH$_3$ | K48 | A87 I |
| 4780 | C$_8$H$_{17}$— | —O—C$_5$H$_{10}$—CH=CH$_2$ | K37 | A80 I |
| 4781 | C$_8$H$_{17}$— | —O—C$_5$H$_{10}$—CH=CH—CH$_3$ | K44 | A85 I |
| 4782 | C$_9$H$_{19}$— | —O—C$_5$H$_{10}$—CH=CH$_2$ | K38 | A81 I |
| 4783 | C$_9$H$_{19}$— | —O—C$_5$H$_{10}$—CH=CH—CH$_3$ | K51 | A86 I |
| 4785 | C$_3$H$_7$—O—C$_5$H$_{10}$— | —O—C$_5$H$_{10}$—CH=CH$_2$ | K10 | A59 I |
| 4786 | C$_3$H$_7$—O—C$_5$H$_{10}$— | —O—C$_5$H$_{10}$—CH=CH—CH$_3$ | K21 | A70 I |
| 4788 | C$_6$H$_{13}$— | —O—C$_6$H$_{12}$—CH=CH$_2$ | K26 | C54 A75 I |
| 4789 | C$_7$H$_{15}$— | —O—C$_6$H$_{12}$—CH=CH$_2$ | K24 | C50 A78 I |
| 4790 | C$_8$H$_{17}$— | —O—C$_6$H$_{12}$—CH=CH$_2$ | K42 | C43 A76 I |
| 4791 | C$_9$H$_{19}$— | —O—C$_6$H$_{12}$—CH=CH$_2$ | K34 | C38 A77 I |
| 4792 | C$_3$H$_7$—O—C$_5$H$_{10}$— | —O—C$_6$H$_{12}$—CH=CH$_2$ | K15 | C35 A60 I |
| 4793 | C$_6$H$_{13}$— | —O—C$_7$H$_{14}$—CH=CH$_2$ | K20 | C65 A81 I |

TABLE 42-continued

L—⟨phenyl⟩—⟨pyrimidine(N,N)⟩—R

| No | L | R | Cr | LC |
|---|---|---|---|---|
| 4794 | C$_7$H$_{15}$— | —O—C$_7$H$_{14}$—CH=CH$_2$ | K16 | S23 C62 A84 I |
| 4795 | C$_8$H$_{17}$— | —O—C$_7$H$_{14}$—CH=CH$_2$ | K20 | C60 A83 I |
| 4796 | C$_9$H$_{19}$— | —O—C$_7$H$_{14}$—CH=CH$_2$ | K30 | C53 A84 I |
| 4797 | C$_3$H$_7$—O—C$_9$H$_{10}$— | —O—C$_7$H$_{14}$—CH=CH$_2$ | K-30 | C30 A61 I |

TABLE 43

L—⟨phenyl⟩—⟨pyrimidine(N,N)⟩—R

| No | L | R | Cr | LC |
|---|---|---|---|---|
| 4798 | C$_6$H$_{13}$— | —O—C$_8$H$_{16}$—CH=CH$_2$ | K33 | S35 C73 A80 I |
| 4799 | C$_7$H$_{15}$— | —O—C$_8$H$_{16}$—CH=CH$_2$ | K32 | S33 C72 A82 I |
| 4800 | C$_8$H$_{17}$— | —O—C$_8$H$_{16}$—CH=CH$_2$ | K36 | C72 A81 I |
| 4801 | C$_9$H$_{19}$— | —O—C$_8$H$_{16}$—CH=CH$_2$ | K35 | C71 A82 I |
| 4802 | C$_3$H$_7$—O—C$_5$H$_{10}$ | —O—C$_8$H$_{16}$—CH=CH$_2$ | K-3 | C57 A64 I |
| 4803 | C$_6$H$_{13}$— | —O—C$_9$H$_{18}$—CH=CH$_2$ | K29 | S28 C76 A82 I |
| 4804 | C$_6$H$_{13}$— | —O—C$_{10}$H$_{20}$—CH=CH$_2$ | K33 | S35 C76 A81 I |
| 4805 | C$_7$H$_{15}$— | —O—C$_9$H$_{18}$—CH=CH$_2$ | K28 | S29 C77 A85 I |
| 4806 | C$_7$H$_{15}$— | —O—C$_{10}$H$_{20}$—CH=CH$_2$ | K38 | S40 C79 A84 I |
| 4807 | C$_8$H$_{17}$— | —O—C$_9$H$_{18}$—CH=CH$_2$ | K38 | C78 A84 I |
| 4808 | C$_8$H$_{17}$— | —O—C$_{10}$H$_{20}$—CH=CH$_2$ | K43 | C80 A82 I |
| 4809 | C$_9$H$_{19}$ | —O—C$_9$H$_{18}$—CH=CH$_2$ | K38 | C78 A85 I |
| 4810 | C$_9$H$_{19}$ | —O—C$_{10}$H$_{20}$—CH=CH$_2$ | K43 | C82 A83 I |
| 4811 | C$_3$H$_7$—O—C$_5$H$_{10}$ | —O—C$_9$H$_{18}$—CH=CH$_2$ | K0 | C55 A65 I |
| 4812 | C$_3$H$_7$—O—C$_5$H$_{10}$ | —O—C$_{10}$H$_{20}$—CH=CH$_2$ | K19 | S36 S59 C70 I |
| 4817 | C$_8$H$_{17}$— | —O—C$_2$H$_4$—CH%CH—C$_4$H$_9$ | K52 | A43 I |
| 4818 | C$_9$H$_{19}$ | —O—C$_2$H$_4$—CH%CH—C$_4$H$_9$ | K52 | A44 I |
| 4822 | C$_6$H$_{13}$— | —O—C$_4$H$_8$—CH%CH—C$_2$H$_5$ | K45 | C52 A55 I |
| 4823 | C$_7$H$_{15}$ | —O—C$_4$H$_8$—CH%CH—C$_2$H$_5$ | K42 | C52 A55 I |
| 4824 | C$_8$H$_{17}$— | —O—C$_4$H$_8$—CH%CH—C$_2$H$_5$ | K38 | C46 A57 I |
| 4825 | C$_9$H$_{19}$ | —O—C$_4$H$_8$—CH%CH—C$_2$H$_5$ | K38 | C44 A58 I |
| 4826 | C$_3$H$_7$—O—C$_5$H$_{10}$ | —O—C$_4$H$_8$—CH%CH—C$_2$H$_5$ | K10 | C33 A37 I |
| 4828 | C$_9$H$_{19}$—O— | —O—C$_4$H$_8$—O—CH$_2$—CH/CH$_2$ CH$_2$ | K72.4 | C58.4 N72 I |
| 4829 | C$_6$H$_{13}$—O— | —O—C$_4$H$_8$—CH/CH$_2$ CH$_2$ | K64 | C48 N88 U |
| 4830 | C$_4$H$_9$—O—C$_4$H$_8$—O— | —O—C$_4$H$_8$—CH/CH$_2$ CH$_2$ | K42 | C45 A47 N64 I |
| 4831 | C$_6$H$_{13}$—O— | —O—C$_5$H$_{10}$—CH/CH$_2$ CH$_2$ | K53 | C73 A75 N86 I |
| 4832 | C$_4$H$_9$—O—C$_4$H$_8$—O— | —O—C$_5$H$_{10}$—CH/CH$_2$ CH$_2$ | K39 | C63 A65 N67 I |
| 4833 | C$_8$H$_{17}$—O— | —O—C$_6$H$_{12}$—CH/CH$_2$ CH$_3$ | K56 | C78 A84 N89 I |
| 4834 | C$_8$H$_{19}$—O— | —O—C$_6$H$_{12}$—CH/CH$_2$ CH$_2$ | K56.5 | C79 A85 N89.5 I |

TABLE 44

L—⟨phenyl⟩—⟨pyrimidine(N,N)⟩—R

| No | L | R | Cr | LC |
|---|---|---|---|---|
| 4835 | C$_{11}$H$_{23}$—O— | —O—C$_6$H$_{12}$—CH/CH$_2$ CH$_2$ | K57.5 | C76.5 A86.7 N87 I |
| 4836 | C$_{12}$H$_{25}$—O— | —O—C$_6$H$_{12}$—CH/CH$_2$ CH$_2$ | K61 | C>70 A87 I |
| 4837 | C$_4$H$_9$—O—C$_4$H$_8$—O— | —O—C$_6$H$_{12}$—CH/CH$_2$ CH$_2$ | K46 | C66 A67 N69 I |

TABLE 44-continued

L—⌬—(pyrimidine)—R

| No | L | R | Cr | LC |
|---|---|---|---|---|
| 4838 | C₆H₁₃—O— | —O—C₇H₁₄—CH/CH₂  CH₂ | K51.8 | C86.5 A89.6 N89.8 I |
| 4839 | C₉H₁₉—O— | —O—C₇H₁₄—CH/CH₂  CH₂ | K60 | C87.9 A90.4 I |
| 4840 | C₁₀H₂₁—O— | —O—C₇H₁₄—CH/CH₂  CH₂ | K55.7 | C90 A92.5 I |
| 4841 | C₁₁H₂₃—O— | —O—C₇H₁₄—CH/CH₂  CH₂ | K53.4 | C87.6 A90.5 I |
| 4842 | C₁₂H₂₅—O— | —O—C₇H₁₄—CH/CH₂  CH₂ | K67.4 | C86.1 A90.5 I |
| 4843 | C₄H₉—O—C₄H₈—O— | —O—C₇H₁₄—CH/CH₂  CH₂ | K43 | C73 I |
| 4844 | C₄H₉—O— | —O—C₈H₁₆—CH/CH₂  CH₂ | K55.4 | C81 A87.8 I |
| 4845 | C₆H₁₃—O— | —O—C₈H₁₆—CH/CH₂  CH₂ | K54.1 | C88.2 A90.8 I |
| 4846 | C₈H₁₇—O— | —O—C₈H₁₆—CH/CH₂  CH₂ | K56.4 | C91.7 A92.9 I |
| 4847 | C₉H₁₉—O— | —O—C₈H₁₆—CH/CH₂  CH₂ | K56.2 | C91.8 A93 I |
| 4848 | C₁₀H₂₁—O— | —O—C₈H₁₆—CH/CH₂  CH₂ | K58.5 | C91.6 A92 I |
| 4849 | C₁₁H₂₃—O— | —O—C₈H₁₆—CH/CH₂  CH₂ | K53.6 | C92.3 A93.1 I |
| 4850 | C₁₂H₂₅ O— | —O—C₈H₁₆—CH/CH₂  CH₂ | K54.9 | C92.3 A93 I |
| 4851 | C₇H₁₅—O— | —O—C₉H₁₈—CH/CH₂  CH₂ | K64.7 | C91 I |
| 4852 | C₈H₁₇—O— | —O—C₉H₁₈—CH/CH₂  CH₂ | K63.7 | C93.2 I |
| 4853 | C₁₂H₂₅—O— | —O—C₁₁H₂₂—CH/CH₂  CH₂ | K64.6 | C73.8 I |
| 4854 | C₈H₁₇— | —O—CH₂—CH/O  CH(t)—C₃H₇  1 | K55 | B90 A102 I |
| 4855 | C₈H₁₇— | —O—CH₂—CH/O  CH(t)—C₅H₁₁  1 | K70 | F*101 A104 I |
| 4857 | C₂H₅—CMe₂—C₄H₈—O— | —O—CH₂—CH/O  CH(t)—C₄H₉  1 | K83 | S87 A92 I |
| 4858 | C₂H₅—CMe₂—C₆H₁₂—O— | —O—CH₂—CH/O  CH(t)—C₄H₉  1 | K90 | C*96 A106 I |
| 4859 | C₂H₅—CHMe—O—CH₂ | —C₁₀H₂₁  1 | K15.6 | S15.2 I |
| 4861 | C₆H₁₃—CHMe—O—CH₂ | —C₁₀H₂₁  2 | K16.9 | A-8.5 I |
| 4869 | C₂H₅—CHMe—COO— | —C₁₁H₂₃  S | K52.2 | S40.7 I |
| 4871 | C₂H₅—CHMe—COO— | —O—C₈H₁₇  S | K66 | C*62.2 I |
| 4872 | C₂H₅—CHMe—COO— | —O—C₁₁H₂₃  S | K43 | C*64.1 S67.2 I |
| 4873 | CH₃—CHMe—CHCl—COO— | —C₇H₁₅  S | K64 | X-10 I |
| 4875 | C₂H₅—CHMe—CHCl—COO— | —C₇H₁₅  3 | K59 | X-20 I |

TABLE 45

L—⌬—(pyrimidine)—R

| No | L | R | Cr | LC |
|---|---|---|---|---|
| 4919 | C₂H₅—CHMe—C₃H₆—O— | —C₈H₁₇ | S K31.2 | B16.8 C*46.8 A50.8 I |
| 4920 | C₂H₅—CHMe—C₃H₆—O— | —C₉H₁₉ | S K23 | S28 C*30 A51.5 N*52 I |
| 4921 | C₂H₅—CHMe—C₃H₆—O— | —C₁₀H₂₁ | S K33 | S38.5 C*58 I |
| 4922 | C₂H₅—CHMe—C₃H₆—O— | —C₁₁H₂₃ | S K35.9 | C*60 I |
| 4923 | C₂H₅—CHMe—C₃H₆—O— | —C₁₂H₂₅ | S K41 | S23.8 C*62.2 I |
| 4924 | C₂H₅—CHMe—C₃H₆—O— | —C₁₄H₂₉ | S K32 | B45 C*59.8 I |
| 4925 | C₃H₇—CHMe—C₃H₆—O— | —C₉H₁₉ | 2 K15.5 | C44.5 A54.5 I |
| 4926 | C₅H₁₁—CHMe—C₃H₆—O— | —C₈H₁₇ | 2 K15 | C9 A42.5 I |
| 4927 | C₂H₅—CHMe—C₃H₆—CHMe—CH₂—O— | —C₈H₁₇ | 7 K37 | A34 I |
| 4928 | CH₃—CHMe—C₃H₆—CHMe—C₂H₄—O— | —C₉H₁₉ | S K27 | A40 I |
| 4931 | CH₃—CHMe—C₃H₆—CHMe—CH₂—COO— | —C₉H₁₉ | S K44 | C*<7 I |
| 4932 | C₂H₅—CHMe—C₄H₈—O— | —C₆H₁₃ | S K-5 | A27 N*42 I |
| 4933 | C₂H₅—CHMe—C₄H₈—O— | —C₇H₁₅ | S K-6 | A46.3 N*49 I |
| 4934 | C₂H₅—CHMe—C₄H₈—O— | —C₈H₁₇ | S K12 | C*34.7 A49.5 I |
| 4935 | C₂H₅—CHMe—C₄H₈—O— | —C₉H₁₉ | S K10 | C*46 A59 I |
| 4936 | C₂H₅—CHMe—C₄H₈—O— | —C₁₀H₂₁ | S K17 | C*53.8 A63 I |
| 4937 | C₂H₅—CHMe—C₄H₈—O— | —C₁₁H₂₃ | S K20 | C*59 I |
| 4938 | C₂H₅—CHMe—C₄H₈—O— | —C₁₂H₂₅ | S K23 | S16 C*61.5 I |
| 4939 | C₃H₇—CHMe—C₄H₈—O— | —C₈H₁₇ | 2 K3.5 | S31.5 A47.5 I |
| 4940 | C₂H₅—CHMe—C₄H₈—CO— | —C₈H₁₇ | S K67 | C*69 A79.3 I |
| 4941 | C₂H₅—CHMe—C₄H₈—COO— | —C₈H₁₇ | S K38.5 | S24 C*44.8 I |
| 4942 | C₂H₅—CHMe—C₄H₈—COO— | —C₁₁H₂₃ | S K62.3 | S46.5 C*60 I |
| 4943 | C₂H₅—CHMe—C₄H₈—COO— | —C₁₄H₂₉ | S K46 | S50 C*62.8 I |
| 4944 | C₂H₅—CHMe—C₄H₈—COO— | —O—C₈H₁₇ | S K76 | C*79.5 I |
| 4945 | C₂H₅—CHMe—C₅H₁₀—O— | —C₆H₁₃ | S K12 | C*23.8 N*45.6 I |

TABLE 45-continued

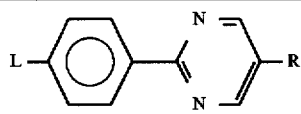

| No | L | R | Cr | LC |
|---|---|---|---|---|
| 4946 | C₂H₅—CHMe—C₅H₁₀—O— | —C₇H₁₅ | S K10 | S16 C*39 A54 N*61 I |
| 4947 | C₂H₅—CHMe—C₅H₁₀—O— | —C₈H₁₇ | S K3 | B14.2 C*48.6 A56.3 I |
| 4948 | C₂H₅—CHMe—C₅H₁₀—O— | —C₉H₁₉ | S K16 | C*49.1 A61 I |
| 4949 | C₂H₅—CHMe—C₅H₁₀—O— | —C₁₀H₂₁ | S K41 | S<? C*61 I |
| 4950 | C₂H₅—CHMe—C₅H₁₀—O— | —C₁₁H₂₃ | S K? | B36.7 C*68 I |

TABLE 46

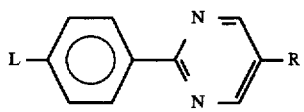

| No | L | R | Cr | LC |
|---|---|---|---|---|
| 4951 | C₂H₅—CHMe—C₅H₁₀—O— | —C₁₂H₂₅ | S K40.5 | C*70 I |
| 4952 | C₂H₅—CHMe—C₅H₁₀—O— | —C₁₄H₂₉ | S K43 | B45 C*66 I |
| 4953 | C₂H₅—CHMe—C₅H₁₀—O— | —C₈H₁₇ | 2 K3 | C47.5 A58 I |
| 4954 | C₂H₅—CHMe—C₅H₁₀—O— | —O—C₈H₁₇ | S K40.7 | C*82.8 A89.1 I |
| 4955 | C₂H₅—CHMe—C₅H₁₀—O— | —COO—C₈H₁₇ | S K76.5 | C*79.7 I |
| 4956 | CH₃—CHMe—C₆H₁₂— | —C₉H₁₉ | K29.5 | F31 A58.2 I |
| 4957 | CH₃—CHMe—C₅H₁₂— | —C₁₀H₂₁ | K38.6 | F41.3 C51.4 A58.4 I |
| 4962 | C₂H₅—CHF—COO— | —C₉H₁₉ | 1 K70 | S58 I |
| 4964 | C₂H₅—CHF—COO— | —C₁₂H₂₅ | 1 K69 | A59 I |
| 4965 | C₄H₉—CHF—COO— | —C₁₀H₂₁ | S K46 | S30 A49 I |
| 4966 | C₄H₉—CHF—COO— | —C₁₂H₂₅ | S K59 | C*45 A52 I |
| 4968 | C₅H₁₁—CHF—COO— | —C₁₂H₂₅ | S K14 | S? A50 I |
| 4969 | C₆H₁₃—CHF—COO— | —C₈H₁₇ | 1 K56 | A38 I |
| 4970 | C₆H₁₃—CHF—COO— | —C₉H₁₉ | 1 K53 | A46 I |
| 4971 | C₆H₁₃—CHF—COO— | —C₁₀H₂₁ | 1 K57 | S32 C*45 I |
| 4972 | C₆H₁₃—CHF—COO— | —C₁₂H₂₅ | 1 K62 | C*52 I |
| 4973 | C₇H₁₅—CHF—COO— | —C₁₀H₂₁ | S K59 | A46 I |
| 4974 | C₇H₁₅—CHF—COO— | —C₁₂H₂₅ | S K22 | S? A61 I |
| 4976 | C₈H₁₇—CHF—COO— | —C₉H₁₉ | 1 K64 | A46 I |
| 4977 | C₈H₁₇—CHF—COO— | —C₁₀H₂₁ | 1 K59 | C*43 A46 N*48 I |
| 4978 | C₈H₁₇—CHF—COO— | —C₁₂H₂₅ | S K23 | S87 I |
| 4979 | C₄H₉—CHF—CH₂—O— | —C₁₀H₂₁ | S K48 | C*43 A66 I |
| 4980 | C₄H₉—CHF—CH₂—O— | —C₁₂H₂₅ | S K59 | S37 S39 C*43 A71 I |
| 4981 | C₅H₁₁—CHF—CH₂—O— | —C₈H₁₇ | S K24 | A35 I |
| 4982 | C₅H₁₁—CHF—CH₂—O— | —C₁₀H₂₁ | S K49 | C*60 A66 I |
| 4983 | C₅H₁₁—CHF—CH₂—O— | —C₁₂H₂₅ | S K60 | S49 C*61 A72 I |
| 4984 | C₆H₁₃—CHF—CH₂—O— | —C₈H₁₇ | S K62 | A59 I |
| 4985 | C₆H₁₃—CHF—CH₂—O— | —C₉H₁₉ | S K63 | A67 I |
| 4986 | C₆H₁₃—CHF—CH₂—O— | —C₁₀H₂₁ | S K61 | S49 C*62 A71 I |
| 4987 | C₆H₁₃—CHF—CH₂—O— | —C₁₂H₂₅ | S K56 | C*70 A74 I |

TABLE 47

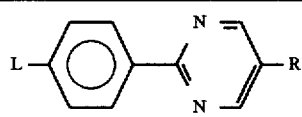

| No | L | R | Cr | LC |
|---|---|---|---|---|
| 5039 | CF₃—O— | —C₃H₇ | K43.1 | S48.2 N-17 E |

TABLE 47-continued

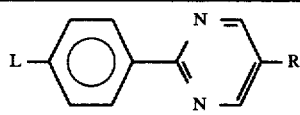

| No | L | R | Cr | LC |
| --- | --- | --- | --- | --- |
| 5040 | CF$_3$—O— | —C$_5$H$_{11}$ | K32 | A45.2 N- 6 |
| 5041 | CF$_3$—O— | —C$_7$H$_{15}$ | K25 | A34 N-20 E |
| 5042 | C$_9$F$_{19}$—O— | —C$_8$H$_{17}$ | K65.1 | A115.1 I |
| 5043 | C$_3$F$_7$—CH$_2$—O— | —C$_{10}$H$_{21}$ | K36 | C52 A64 I |
| 5044 | C$_5$F$_{11}$—CH$_2$—O— | —C$_{10}$H$_{21}$ | K47 | C73 A84 I |
| 5045 | C$_6$F$_{13}$—CH$_2$—O— | —C$_7$H$_{15}$ | K? | C? A? I |
| 5046 | C$_7$F$_{15}$—CH$_2$—O— | —C$_6$H$_{13}$ | K50 | C56 A133 I |
| 5047 | C$_7$F$_{15}$—CH$_2$—O— | —C$_7$H$_{15}$ | K54 | C67 A125 I |
| 5048 | C$_7$F$_{15}$—CH$_2$—O— | —C$_8$H$_{17}$ | K71 | C80 A117 I |
| 5049 | C$_7$F$_{15}$—CH$_2$—O— | —C$_9$H$_{19}$ | K71 | C85 A112 I |
| 5050 | C$_7$F$_{15}$—CH$_2$—O— | —C$_{10}$H$_{21}$ | K75 | C87 A104 I |
| 5051 | C$_8$F$_{17}$—CH$_2$—O— | —C$_7$H$_{15}$ | K? | C? A? I |
| 5052 | C$_9$F$_{19}$—CH$_2$—O— | —C$_7$H$_{15}$ | K? | C? A? I |
| 5053 | C$_{10}$F$_{21}$—CH$_2$—O— | —C$_3$H$_7$ | K? | C? A? I |
| 5054 | C$_{10}$F$_{21}$—CH$_2$—O— | —C$_5$H$_{11}$ | K? | C? A? I |
| 5055 | C$_6$F$_{13}$—C$_3$H$_6$—O— | —C$_8$H$_{17}$ | K63 | C95 A132 I |
| 5056 | C$_4$F$_9$—C$_4$H$_8$—O— | —C$_8$H$_{17}$ | K66 | A114 I |
| 5057 | C$_4$F$_9$—C$_4$H$_8$—O— | —C$_{10}$H$_{21}$ | K58 | C80 A106 I |
| 5061 | H—CF$_2$—O— | —C$_3$H$_7$ | K41 | NO E |
| 5062 | H—CF$_2$—O— | —C$_5$H$_{11}$ | K21 | A26 NO E |
| 5063 | H—CF$_2$—O— | —C$_7$H$_{15}$ | K26 | A32 NO E |
| 5064 | H—CF$_2$—O— | —C$_8$H$_{17}$ | K26.3 | S31.6 N-3 E |
| 5065 | H—C$_2$F$_4$—O— | —C$_7$H$_{15}$ | K46 | X43 I |
| 5066 | H—CF$_2$—S— | —C$_3$H$_7$ | K53.2 | N-16 E |
| 5067 | H—CF$_2$—S— | —C$_5$H$_{11}$ | K43.1 | N-6 E |
| 5068 | C$_6$H$_{13}$—CHCF$_3$—O—CH$_2$— | —C$_{10}$H$_{21}$ | 1 K56.8 | S18.4 I |
| 5070 | C$_4$H$_9$—CHCF$_3$—CH$_2$—COO— | —C$_{10}$H$_{21}$ | 1 K28 | S1 S7 I |
| 5072 | H$_2$C=CH—COO—C$_6$H$_{12}$—O— | —C$_8$H$_{17}$ | K50 | S52.5 N53 I |

TABLE 48

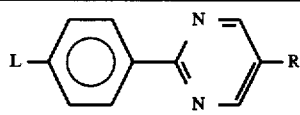

| No | L | R | Cr | LC |
| --- | --- | --- | --- | --- |
| 5106 | CH$_3$—CH=CH—CH$_2$—O— | —C$_9$H$_{19}$ | K59 | A65 N75 I |
| 5107 | C$_2$H$_5$—CH=CH—CH$_2$—O— | —C$_7$H$_{15}$ | K31 | C30 N62 I |
| 5108 | C$_2$H$_5$—CH=CH—CH$_2$—O— | —C$_8$H$_{17}$ | K53 | C49 A55 N61 I |
| 5109 | C$_2$H$_5$—CH=CH—CH$_2$—O— | —C$_9$H$_{19}$ | K56 | C42 A68 I |
| 5111 | C$_3$H$_7$—CH=CH—CH$_2$—O— | —C$_9$H$_{17}$ | K43 | C51 N66 I |
| 5112 | C$_3$H$_7$—CH=CH—CH$_2$—O— | —C$_9$H$_{19}$ | K49 | C63 A70 N72 I |
| 5113 | C$_3$H$_7$—CH=CH—CH$_2$—O— | —C$_{10}$H$_{21}$ | K30 | C53 A65.5 I |
| 5114 | C$_4$H$_9$—CH=CH—CH$_2$—O— | —C$_7$H$_{15}$ | K22 | C33 N63 I |
| 5115 | C$_4$H$_9$—CH=CH—CH$_2$—O— | —C$_8$H$_{17}$ | K30 | C55 N64 I |
| 5116 | C$_4$H$_9$—CH=CH—CH$_2$—O— | —C$_9$H$_{19}$ | K46 | C66 A70 I |
| 5117 | C$_5$H$_{11}$—CH=CH—CH$_2$—O— | —C$_7$H$_{15}$ | K38 | C35 N68 I |
| 5118 | C$_5$H$_{11}$—CH=CH—CH$_2$—O— | —C$_8$H$_{17}$ | K24 | C56 N68 I |
| 5119 | C$_5$H$_{11}$—CH=CH—CH$_2$—O— | —C$_9$H$_{19}$ | K42 | C70 A72 N73 I |
| 5120 | C$_6$H$_{13}$—CH=CH—CH$_2$—O— | —C$_7$H$_{15}$ | K40 | C41 N66 I |
| 5121 | C$_6$H$_{13}$—CH=CH—CH$_2$—O— | —C$_8$H$_{17}$ | K29 | C58 N66 I |
| 5122 | C$_6$H$_{13}$—CH=CH—CH$_2$—O— | —C$_9$H$_{19}$ | K20 | C70 A71 N72 I |
| 5123 | C$_7$H$_{15}$—CH=CH—CH$_2$—O— | —C$_7$H$_{15}$ | K49 | C42 N68 I |
| 5124 | C$_7$H$_{15}$—CH=CH—CH$_2$—O— | —C$_8$H$_{17}$ | K31 | C59 N68 I |
| 5125 | C$_7$H$_{15}$—CH=CH—CH$_2$—O— | —C$_9$H$_{19}$ | K37 | C72 A73 N74 I |
| 5126 | C$_8$H$_{17}$—CH=CH—CH$_2$—O— | —C$_7$H$_{15}$ | K43 | C47 N66 I |
| 5127 | C$_8$H$_{17}$—CH=CH—CH$_2$—O— | —C$_8$H$_{17}$ | K40 | C60 N66 I |
| 5128 | C$_8$H$_{17}$—CH=CH—CH$_2$—O— | —C$_9$H$_{19}$ | K36 | C72 A73 I |
| 5129 | C$_9$H$_{19}$—CH=CH—CH$_2$—O— | —C$_7$H$_{15}$ | K55 | C49 N68 I |
| 5130 | C$_9$H$_{19}$—CH=CH—CH$_2$—O— | —C$_8$H$_{17}$ | K44 | C62 N68 I |

TABLE 48-continued

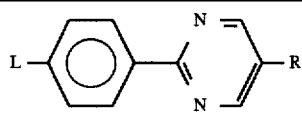

| No | L | R | Cr | LC |
|---|---|---|---|---|
| 5131 | $C_9H_{19}-CH=CH-CH_2-O-$ | $-C_9H_{19}$ | K42 | C74 I |
| 5132 | $H_2C=CH-C_2H_4-O-$ | $-C_4H_9$ | K37.3 | N12.5 U |
| 5133 | $H_2C=CH-C_2H_4-O-$ | $-C_7H_{15}$ | K38 | A41 N49 I |
| 5134 | $H_2C=CH-C_2H_4-O-$ | $-C_8H_{17}$ | K34 | A46 I |
| 5135 | $H_2C=CH-C_2H_4-O-$ | $-C_9H_{19}$ | K55 | A56 I |

TABLE 49

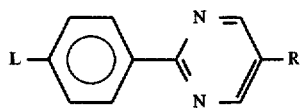

| No | L | R | Cr | LC |
|---|---|---|---|---|
| 5139 | $C_3H_7-CH=CH-C_2H_4-COO-$ | $-C_8H_{17}$ | K54 | A45 N50 I |
| 5140 | $C_3H_7-CH=CH-C_2H_4-COO-$ | $-C_9H_{19}$ | K67 | A61 I |
| 5142 | $H_2C=CH-C_3H_6-O-$ | $-C_7H_{15}$ | K46 | A45 N63 I |
| 5143 | $H_2C=CH-C_3H_6-O-$ | $-C_8H_{17}$ | K38 | A54 N58 I |
| 5144 | $H_2C=CH-C_3H_6-O-$ | $-C_9H_{19}$ | K40 | A65 I |
| 5145 | $CH_3-CH=CH-C_3H_6-O-$ | $-C_9H_{19}$ | K48 | C35 A70 N72 I |
| 5146 | $C_3H_7-CH=CH-C_3H_6-O-$ | $-C_7H_{15}$ | K39 | C45 N65 I |
| 5147 | $C_3H_7-CH=CH-C_3H_6-O-$ | $-C_8H_{17}$ | K32 | C56 A59 N63 I |
| 5148 | $C_3H_7-CH=CH-C_3H_6-O-$ | $-C_9H_{19}$ | K42 | C64 A73 I |
| 5151 | $H_2C=CH-C_4H_8-O-$ | $-C_7H_{15}$ | K27 | A43 N57 I |
| 5152 | $H_2C=CH-C_4H_8-O-$ | $-C_8H_{17}$ | K44 | A51 N55 I |
| 5153 | $H_2C=CH-C_4H_8-O-$ | $-C_9H_{19}$ | K48 | A62 I |
| 5154 | $H_2C=CH-C_4H_8-O-$ | $-C_{10}H_{21}$ | K55.5 | C33 A62 I |
| 5155 | $CH_3-CH=CH-C_4H_8-COO-$ | $-C_7H_{15}$ | K51 | A34 N55 I |
| 5156 | $CH_3-CH=CH-C_4H_8-COO-$ | $-C_8H_{17}$ | K48 | C39 A46 N52 I |
| 5157 | $CH_3-CH=CH-C_4H_8-COO-$ | $-C_9H_{19}$ | K56 | C48 A60 I |
| 5160 | $H_2C=CH-C_5H_{10}-O-$ | $-C_7H_{15}$ | K56 | C34 A47 N67 I |
| 5161 | $H_2C=CH-C_5H_{10}-O-$ | $-C_8H_{17}$ | K37 | C30 A58 N64 I |
| 5162 | $H_2C=CH-C_5H_{10}-O-$ | $-C_9H_{19}$ | K31 | A69 I |
| 5163 | $CH_3-CH=CH-C_5H_{10}-O-$ | $-C_7H_{15}$ | K39 | C45 A65 I |
| 5164 | $CH_3-CH=CH-C_5H_{10}-O-$ | $-C_8H_{17}$ | K40 | C52 A57 N67 I |
| 5165 | $CH_3-CH=CH-C_5H_{10}-O-$ | $-C_9H_{19}$ | K39 | C53 A71 N72 I |
| 5166 | $H_2C=CH-C_5H_{10}-COO-$ | $-C_7H_{15}$ | K43 | A36 N46 I |
| 5167 | $H_2C=CH-C_5H_{10}-COO-$ | $-C_8H_{17}$ | K37 | C34 A43 N44 I |
| 5168 | $H_2C=CH-C_5H_{10}-COO-$ | $-C_9H_{19}$ | K48 | C42 A56 I |
| 5169 | $H_2C=CH-C_5H_{10}-O-$ | $-C_4H_8-CHMe-C_2H_5$ S | K35 | C*29 N*46 I |
| 5170 | $H_2C=CH-C_5H_{10}-O-$ | $-C_5H_{10}-CHMe-C_2H_5$ S | K7 | C*19 N*39 I |

TABLE 50

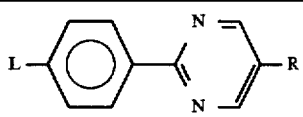

| No | L | R | Cr | LC |
|---|---|---|---|---|
| 5171 | $H_2C=CH-C_6H_{12}-O-$ | $-C_7H_{15}$ | K36 | C33 A48 N62 I |
| 5172 | $H_2C=CH-C_6H_{12}-O-$ | $-C_8H_{17}$ | K19.2 | C33.3 A56.1 N60.2 I |
| 5173 | $H_2C=CH-C_6H_{12}-O-$ | $-C_9H_{19}$ | K37 | A67 I |
| 5174 | $H_2C=CH-C_6H_{12}-O-$ | $-C_{10}H_{21}$ | K38.2 | C49.6 A67.9 I |

TABLE 50-continued

| No | L | R | | Cr | LC |
|---|---|---|---|---|---|
| 5175 | $H_2C=CH-C_6H_{12}-O-$ | $-O-C_8H_{17}$ | | K48.5 | C76.3 A92 N92.6 I |
| 5176 | $H_2C=CH-C_6H_{12}-O-$ | $-C_4H_8-CHMe-C_2H_5$ | S | K29 | C*28 N*40 I |
| 5177 | $H_2C=CH-C_6H_{12}-O-$ | $-C_5H_{10}-CHMe-C_2H_5$ | S | K4 | C*15 N*32 I |
| 5178 | $H_2C=CH-C_7H_{14}-O-$ | $-C_7H_{15}$ | | K52 | C43 A54 N67 I |
| 5179 | $H_2C=CH-C_7H_{14}-O-$ | $-C_8H_{17}$ | | K27 | C45 A62 N66 I |
| 5180 | $H_2C=CH-C_7H_{14}-O-$ | $-C_9H_{19}$ | | K19 | C39 A71 I |
| 5181 | $H_2C=CH-C_7H_{14}-O-$ | $-C_{10}H_{21}$ | | K32.5 | C55 A72 I |
| 5182 | $H_2C=CH-C_7H_{14}-O-$ | $-C_4H_8-CHMe-C_2H_5$ | S | K16 | C*35 N*48 I |
| 5183 | $H_2C=CH-C_7H_{14}-O-$ | $-C_5H_{10}-CHMe-C_2H_5$ | S | K-1 | C*28 N*42 I |
| 5184 | $H_2C=CH-C_8H_{16}-O-$ | $-C_7H_{15}$ | | K43 | C42 A55 N64 I |
| 5185 | $H_2C=CH-C_8H_{16}-O-$ | $-C_8H_{17}$ | | K24 | C46 A60 N63 I |
| 5186 | $H_2C=CH-C_8H_{16}-O-$ | $-C_9H_{19}$ | | K35 | C45 A70 I |
| 5187 | $H_2C=CH-C_8H_{16}-O-$ | $-C_{10}H_{21}$ | | K33 | C57 A70 I |
| 5188 | $H_2C=CH-C_8H_{16}-O-$ | $-C_4H_8-CHMe-C_2H_5$ | S | K17 | C*34 N*44 I |
| 5189 | $H_2C=CH-C_8H_{16}-O-$ | $-C_5H_{10}-CHMe-C_2H_5$ | S | K12 | C*27 N*38 I |
| 5191 | $H_2C=CH-C_9H_{18}-O-$ | $-C_7H_{15}$ | | K49 | C46 A59 N67 I |
| 5192 | $H_2C=CH-C_9H_{18}-O-$ | $-C_8H_{17}$ | | K33.9 | C53 A64.4 N66.2 I |
| 5193 | $H_2C=CH-C_9H_{18}-O-$ | $-C_9H_{19}$ | | K31.3 | C52.8 A71.7 I |
| 5194 | $H_2C=CH-C_9H_{18}-O-$ | $-C_{10}H_{21}$ | | K39.9 | C65.2 A72.5 I |
| 5195 | $H_2C=CH-C_9H_{18}-O-$ | $-C_{12}H_{25}$ | | K45.9 | C75.5 A76.5 I |
| 5196 | $H_2C=CH-C_{10}H_{20}-O-$ | $-C_7H_{15}$ | | K50 | C45 A60 N65 I |
| 5197 | $H_2C=CH-C_{10}H_{20}-O-$ | $-C_8H_{17}$ | | K36 | C50 A63 N64 I |
| 5198 | $H_2C=CH-C_{10}H_{20}-O-$ | $-C_9H_{19}$ | | K46 | C50 A70 I |
| 5199 | $H_2C=CH-C_9H_{18}-O-$ | $-O-C_8H_{17}$ | | K44.1 | C78.5 A94.5 I |
| 5200 | $H_2C=CH-C_9H_{18}-O-$ | $-C_4H_8-CHMe-C_2H_5$ | S | K20 | C*40 N*49 I |
| 5201 | $H_2C=CH-C_{10}H_{20}-O-$ | $-C_4H_8-CHMe-C_2H_5$ | S | K35 | C*40 N*47 I |

TABLE 51

| No | L | R | | Cr | LC |
|---|---|---|---|---|---|
| 5202 | $H_2C=CH-C_9H_{18}-O-$ | $-C_5H_{10}-CHMe-C_2H_5$ | S | K17 | C*36 N*45 I |
| 5203 | $H_2C=CH-C_{10}H_{20}-O-$ | $-C_5H_{10}-CHMe-C_2H_5$ | S | K33 | C*37 N*43 I |
| 5204 | $C_3H_7-CH\%CH-CH_2-O-$ | $-C_9H_{19}$ | | K32 | A17 I |
| 5208 | $CH_3-CH\%CH-C_2H_4-O-$ | $-C_7H_{15}$ | | K45 | A41 N47 I |
| 5209 | $CH_3-CH\%CH-C_2H_4-O-$ | $-C_8H_{17}$ | | K34 | A45 I |
| 5210 | $CH_3-CH\%CH-C_2H_4-O-$ | $-C_9H_{19}$ | | K48 | C25 A55 I |
| 5211 | $C_2H_5-CH\%CH-C_2H_4-O-$ | $-C_7H_{15}$ | | K43 | A45 N48 I |
| 5212 | $C_2H_5-CH\%CH-C_2H_4-O-$ | $-C_8H_{17}$ | | K42 | C32 A47 I |
| 5213 | $C_2H_5-CH\%CH-C_2H_4-O-$ | $-C_9H_{19}$ | | K58 | C41 A56 I |
| 5214 | $C_3H_7-CH\%CH-C_2H_4-O-$ | $-C_7H_{15}$ | | K20 | A44 I |
| 5215 | $C_3H_7-CH\%CH-C_2H_4-O-$ | $-C_8H_{17}$ | | K33 | C35 A46 I |
| 5216 | $C_3H_7-CH\%CH-C_2H_4-O-$ | $-C_9H_{19}$ | | K34 | C45 A54 I |
| 5217 | $C_4H_9-CH\%CH-C_2H_4-O-$ | $-C_7H_{15}$ | | K28 | A43 N44 I |
| 5218 | $C_4H_9-CH\%CH-C_2H_4-O-$ | $-C_8H_{17}$ | | K25 | C34 A46 I |
| 5219 | $C_4H_9-CH\%CH-C_2H_4-O-$ | $-C_9H_{19}$ | | K24 | C43 A54 I |
| 5220 | $C_5H_{11}-CH\%CH-C_2H_4-O-$ | $-C_7H_{15}$ | | K25 | A40 I |
| 5221 | $C_5H_{11}-CH\%CH-C_2H_4-O-$ | $-C_8H_{17}$ | | K12 | C30 A42 I |
| 5222 | $C_5H_{11}-CH\%CH-C_2H_4-O-$ | $-C_9H_{19}$ | | K6 | C38 A51 I |
| 5223 | $C_6H_{13}-CH\%CH-C_2H_4-O-$ | $-C_7H_{15}$ | | K33 | A39 I |
| 5224 | $C_6H_{13}-CH\%CH-C_2H_4-O-$ | $-C_8H_{17}$ | | K22 | C25 A41 I |
| 5225 | $C_6H_{13}-CH\%CH-C_2H_4-O-$ | $-C_9H_{19}$ | | K19 | C34 A49 I |
| 5226 | $C_7H_{15}-CH\%CH-C_2H_4-O-$ | $-C_7H_{15}$ | | K40 | A37 I |
| 5227 | $C_7H_{15}-CH\%CH-C_2H_4-O-$ | $-C_8H_{17}$ | | K30 | C20 A39 I |
| 5228 | $C_7H_{15}-CH\%CH-C_2H_4-O-$ | $-C_9H_{19}$ | | K26 | C24 A47 I |
| 5229 | $C_8H_{17}-CH\%CH-C_2H_4-O-$ | $-C_7H_{15}$ | | K31 | A35 I |
| 5230 | $C_8H_{17}-CH\%CH-C_2H_4-O-$ | $-C_8H_{17}$ | | K32 | C14 A41 I |

TABLE 51-continued

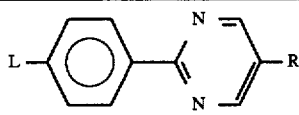

| No | L | R | Cr | LC |
|---|---|---|---|---|
| 5231 | $C_8H_{17}-CH\%CH-C_2H_4-O-$ | $-C_9H_{19}$ | K29 | C14 A50 I |
| 5232 | $CH_3-CH\%CH-C_3H_6-O-$ | $-C_9H_{19}$ | K22 | A46 I |
| 5233 | $C_2H_5-CH\%CH-C_3H_6-COO-$ | $-C_7H_{15}$ | K26 | A31 I |

TABLE 52

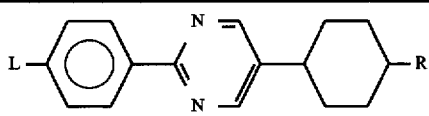

| No | L | R | | Cr | LC |
|---|---|---|---|---|---|
| 27740 | $Cl-CF_2-O-$ | $-C_4H_9$ | | K30 | S130.6 N135.2 I |
| 27749 | $NC-$ | $-C_7H_{15}$ | | K82 | A158 N223 I |
| 27750 | $NC-$ | $-O-C_2H_5$ | | K144.5 | N232 B |
| 27751 | $NC-$ | $-O-C_3H_7$ | | K114.5 | N223.5 B |
| 27752 | $NC-$ | $-O-C_5H_{11}$ | | K93 | N205 B |
| 27753 | $NC-$ | $-CH_2-CHMe-C_2H_5$ | l | K76 | S125 N*178 I |
| 27754 | $NC-$ | $-C_2H_4-CHMe-C_2H_5$ | l | K101 | S159 N*189.5 I |
| 27755 | $C_2H_5-$ | $-C_7H_{15}$ | | K68 | S179 N182 I |
| 27756 | $C_3H_7-$ | $-C_2H_5$ | | K125.5 | S128.5 N167 I |
| 27757 | $C_3H_7-$ | $-C_3H_7$ | | K116.5 | S175 N194.5 I |
| 27758 | $C_3H_7-$ | $-C_5H_{11}$ | | K51 | S190 I |
| 27759 | $C_4H_9-$ | $-C_2H_5$ | | K108.5 | S140 N163.5 I |
| 27760 | $C_4H_9-$ | $-C_5H_{11}$ | | K37.5 | S187 I |
| 27761 | $C_5H_{11}-$ | $-C_2H_5$ | | K101 | S139 N167 I |
| 27762 | $C_5H_{11}-$ | $-C_3H_7$ | | K93.5 | S179 N190 I |
| 27763 | $C_5H_{11}-$ | $-C_5H_{11}$ | | K39.5 | S189.2 I |
| 27764 | $C_5H_{11}-$ | $-C_7H_{15}$ | | K122.5 | S186.5 I |
| 27765 | $C_7H_{15}-$ | $-C_2H_5$ | | K80 | S136.5 N157 I |
| 27768 | $C_6H_{13}-CHMe-O-CH_2-$ | $-C_7H_{15}$ | l | K36.5 | A98.4 I |
| 27769 | $C_2H_5-CHMe-CH_2-O-$ | $-O-C_8H_{17}$ | S | K64.6 | B104.9 A160.5 I |
| 27770 | $C_2H_5-CHMe-CH_2-O-$ | $-O-C_9H_{19}$ | S | K61.7 | B108.2 A156 I |
| 27771 | $C_2H_5-CHMe-C_3H_6-O-$ | $-O-C_8H_{17}$ | S | K68 | B101 A160.9 I |
| 27772 | $C_2H_5-CHMe-C_3H_6-O-$ | $-O-C_9H_{19}$ | S | K63.5 | B103 A157.4 I |

45

TABLE 53

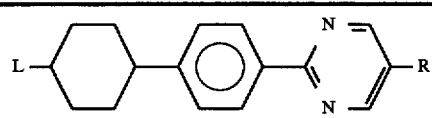

| No | L | R | | Cr | LC |
|---|---|---|---|---|---|
| 28508 | $C_5H_{11}-$ | $-OOC-C_{10}H_{21}$ | | K118 | C133 N172 I |
| 28509 | $C_5H_{11}-$ | $-OOC-C_{11}H_{23}$ | | K120 | C138 N169 I |
| 28510 | $C_4H_9-CHF-COO-$ | $-C_6H_{13}$ | S | K34 | B98 A137 I |
| 28511 | $C_4H_9-CHF-COO-$ | $-C_7H_{15}$ | S | K53 | B101 A143 I |
| 28512 | $C_4H_9-CHF-COO-$ | $-C_8H_{17}$ | S | K41 | B109 A143 I |
| 28513 | $C_4H_9-CHF-COO-$ | $-C_9H_{19}$ | S | K49 | B113 A145 I |
| 28514 | $C_4H_9-CHF-COO-$ | $-C_{10}H_{21}$ | S | K48 | B116 A145 I |
| 28515 | $C_4H_9-CHF-COO-$ | $-O-C_6H_{13}$ | R | K58 | C*81 A161 N*165 I |
| 28516 | $C_4H_9-CHF-COO-$ | $-O-C_7H_{15}$ | R | K44 | B78 C*95 A162 N*163 I |
| 28517 | $C_4H_9-CHF-COO-$ | $-O-C_8H_{17}$ | R | K53 | B88 C*102 A162 I |

TABLE 53-continued

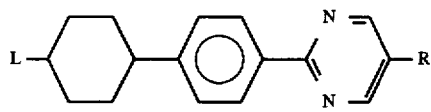

| No | L | R | Cr | LC |
|---|---|---|---|---|
| 28518 | $C_4H_9$—CHF—COO— | —O—$C_9H_{19}$ R | K60 | B92 C*106 A163 I |
| 28519 | $C_4H_9$—CHF—COO— | —O—$C_{10}H_{21}$ R | K35 | S70 B98 C*108 A165 I |
| 28522 | $C_5H_{11}$— | —O—$CH_2$—CH=CH—$C_5H_{11}$ | K97 | C115 N176 I |
| 28523 | $C_5H_{11}$— | —O—$CH_2$—CH=CH—$C_6H_{13}$ | K94 | C125 N170 I |
| 28524 | $C_5H_{11}$— | —O—$CH_2$—CH=CH—$C_7H_{15}$ | K86 | C135 N167 I |
| 28525 | $C_5H_{11}$— | —O—$CH_2$—CH=CH—$C_8H_{17}$ | K93 | C140 N163 I |
| 28526 | $C_5H_{11}$— | —O—$C_3H_6$—CH=CH—$C_3H_7$ | K87 | C93 N184 I |
| 28528 | $C_5H_{11}$— | —O—$C_5H_{10}$—CH=$CH_2$ | K55 | C65 A112 N185 I |
| 28529 | $C_5H_{11}$— | —O—$C_5H_{10}$—CH=CH—$CH_3$ | K81 | C111 A130 N185 I |
| 28530 | $C_5H_{11}$— | —O—$C_6H_{12}$—CH=$CH_2$ | K67 | C96 A121 N176 I |
| 28531 | $C_5H_{11}$— | —O—$C_7H_{14}$—CH=$CH_2$ | K59 | C91 A142 N176 I |
| 28532 | $C_5H_{11}$— | —O—$C_8H_{16}$—CH=$CH_2$ | K55 | C103 A145 N169 I |
| 28533 | $C_5H_{11}$— | —O—$C_9H_{18}$—CH=$CH_2$ | K57 | C97 A151 N168 I |
| 28535 | $C_5H_{11}$— | —O—$C_4H_8$—CH%CH—$C_2H_5$ | K86 | C85 N168 I |
| 28536 | $C_5H_{11}$— | —O—$C_4H_8$—CH/$CH_2$\$CH_2$ | K81 | S75 N180 I |
| 28537 | $C_3H_7$— | —O—$C_6H_{12}$—CH/$CH_2$\$CH_2$ | K80 | S70 C84 N174 I |

TABLE 54

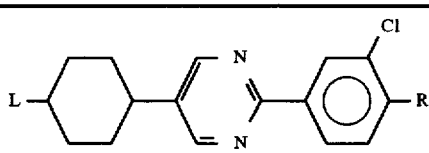

| No | L | R | Cr | LC |
|---|---|---|---|---|
| 28896 | $C_5H_{11}$— | —$C_5H_{11}$ | K33.4 | S121.2 I |

| No | L | R | Cr | LC |
|---|---|---|---|---|
| 28548 | $C_8H_{17}$—O— | —$C_6H_{17}$ | K51 | C63 A113 N121 I |

TABLE 54-continued

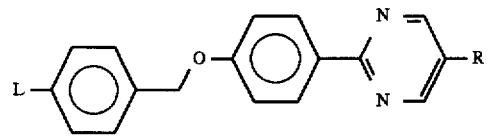

| No | L | R | Cr | LC |
|---|---|---|---|---|
| 33521 | $C_5H_{11}$— | —$C_6H_{13}$ | K72 | S65 N104 I |
| 33522 | $C_5H_{11}$— | —$C_7H_{15}$ | K76 | S86 N109 I |
| 33523 | $C_5H_{11}$— | —$C_9H_{19}$ | K52 | S107 N113 I |
| 33524 | $C_6H_{13}$— | —$C_6H_{13}$ | K61 | S76 N100.8 I |
| 33525 | $C_6H_{13}$— | —$C_7H_{15}$ | K48 | S92 N107 I |
| 33526 | $C_6H_{13}$— | —$C_9H_{19}$ | K66 | S109 N110 I |
| 33527 | $C_8H_{17}$— | —$C_8H_{17}$ | K73 | F66 C103.5 I |

TABLE 55

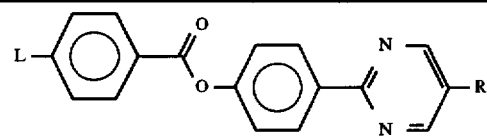

| No | L | R | | Cr | LC |
|---|---|---|---|---|---|
| 33600 | $C_4H_9$—O—CHMe—COO— | —$C_8H_{17}$ | S | K44 | C*60 N*96 I |
| 33601 | $C_4H_9$—O—CHMe—COO— | —O—$C_8H_{17}$ | S | K68 | C*103 N*138 I |
| 33603 | $C_6H_{13}$—O— | —$C_4H_8$—CHMe—$C_2H_5$ | S | K56 | C*54 N*152 I |
| 33604 | $C_7H_{15}$—O— | —$C_4H_8$—CHMe—$C_2H_5$ | S | K64 | C*65 N*148 I |
| 33605 | $C_8H_{17}$—O— | —$C_4H_8$—CHMe—$C_2H_5$ | S | K71 | C*70 N*142 I |
| 33606 | $C_9H_{19}$—O— | —$C_4H_8$—CHMe—$C_2H_5$ | S | K78 | C*77 N*142 I |
| 33607 | $C_{10}H_{21}$—O— | —$C_4H_8$—CHMe—$C_2H_5$ | S | K74 | C*82 N*141 I |
| 33608 | $C_{11}H_{23}$—O— | —$C_4H_8$—CHMe—$C_2H_5$ | S | K78 | C*85 N*136 I |
| 33609 | $C_{12}H_{25}$—O— | —$C_4H_8$—CHMe—$C_2H_5$ | S | K83 | C*88 N*133 I |
| 33610 | $C_6H_{13}$—O— | —$C_5H_{10}$—CHMe—$C_2H_5$ | S | K72 | C*50 N*148 I |

TABLE 55-continued

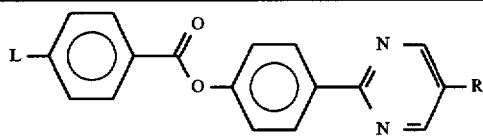

| No | L | R | Cr | LC |
|---|---|---|---|---|
| 33611 | $C_7H_{15}-O-$ | $-C_5H_{10}-CHMe-C_2H_5$ | S K56 | C*64 N*144 I |
| 33612 | $C_8H_{17}-O-$ | $-C_5H_{10}-CHMe-C_2H_5$ | S K56 | C*72 N*142 I |
| 33613 | $C_9H_{19}-O-$ | $-C_8H_{10}-CHMe-C_2H_5$ | S K68 | C*80 N*138 I |
| 33614 | $C_{10}H_{21}-O-$ | $-C_5H_{10}-CHMe-C_2H_5$ | S K86 | C*84 N*137 I |
| 33615 | $C_{11}H_{23}-O-$ | $-C_5H_{10}-CHMe-C_2H_5$ | S K83 | C*90 N*132 I |
| 33616 | $C_{12}H_{25}-O-$ | $-C_5H_{10}-CHMe-C_2H_5$ | S K69 | C*94 N*132 I |
| 33618 | $C_6H_{13}-CHMe-O-$ | $-O-C_8H_{17}$ | 1 K72 | C*48 N*115 I |
| 33620 | $CH_3-CHMe-CHCl-COO-$ | $-C_7H_{15}$ | S K70 | C*96 N*202 I |
| 33621 | $CH_3-CHMe-CHCl-COO-$ | $-C_9H_{19}$ | S K62 | C*69 N*157 I |
| 33622 | $C_2H_5-CHMe-CHCl-COO-$ | $-C_8H_{17}$ | 3 K? | C*77 N*124 I |

TABLE 56

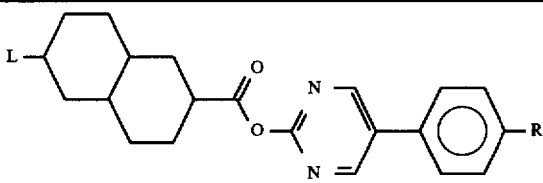

| No | L | R | Cr | LC |
|---|---|---|---|---|
| 36376 | $C_4H_9-$ | $-O-C_9H_{19}$ | 2 K66 | S190 I |

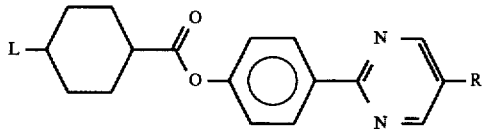

| No | L | R | Cr | LC |
|---|---|---|---|---|
| 37030 | $C_2H_5-$ | $-CN$ | K137 | S136 N243 I |
| 37031 | $C_5H_{11}-$ | $-CN$ | K117 | S192 N248 I |
| 37033 | $CH_3-$ | $-C_{10}H_{21}$ | K76 | C77 N124 I |
| 37035 | $C_2H_5-$ | $-C_{10}H_{21}$ | K82 | C82 N142 I |
| 37038 | $C_3H_7-$ | $-C_{10}H_{21}$ | K76 | C89 N161 I |
| 37039 | $C_3H_7-$ | $-C_{12}H_{25}$ | K64.9 | S76.3 C108.1 N152.8 I |
| 37041 | $C_4H_9-$ | $-C_{10}H_{21}$ | K40 | B82 C99 N160 I |
| 37042 | $C_4H_9-$ | $-C_{12}H_{25}$ | K80 | S82 S83.8 C115.3 N152.7 I |
| 37046 | $C_5H_{11}-$ | $-C_{10}H_{21}$ | K64 | B85 C104 N161 I |
| 37047 | $C_5H_{11}-$ | $-C_{11}H_{23}$ | K70 | S80 S82.7 C114.5 N160.5 I |
| 37048 | $C_5H_{11}-$ | $-C_{12}H_{25}$ | K67 | S83 S87.2 C121.5 N156 I |
| 37051 | $C_7H_{15}-$ | $-C_{10}H_{21}$ | K78 | B89 C116 N158 I |
| 37052 | $C_9H_{19}-$ | $-C_{10}H_{21}$ | K77 | S85 C123 N153 I |
| 37053 | $C_{10}H_{21}-$ | $-C_{10}H_{21}$ | K77 | S87 C125 N150 I |
| 37054 | $C_5H_{11}-$ | $-O-C_8H_{17}$ | K72.1 | S68 S74 C100 N193 I |
| 37055 | $C_5H_{11}-$ | $-O-C_9H_{19}$ | K74.3 | G69 C117.7 N189 I |
| 37056 | $C_5H_{11}-$ | $-O-C_{10}H_{21}$ | K74.7 | G72.5 C129.8 N186.5 I |
| 37058 | $H_2C=CH-C_2H_4-$ | $-C_{10}H_{21}$ | K71 | C92 N162 I |
| 37059 | $CH_3-CH=CH-C_2H_4-$ | $-C_{10}H_{21}$ | K52 | S56 S64 S69 C92 N170 I |

TABLE 57

| No | L | R | | Cr | LC |
|---|---|---|---|---|---|
| 37078 | (Me)$_2$C=CH—C$_2$H$_4$— | —C$_{10}$H$_{21}$ | 2 | K40 | C83 N106 I |
| 37079 | (Me)$_2$C=CH—C$_2$H$_4$— | —O—C$_{10}$H$_{21}$ | 2 | K82 | C112 N138 I |
| 37080 | CH$_3$— | —C$_{10}$H$_{21}$ | 2 | K50 | S54 C68 N107 I |

| No | L | R | Cr | LC |
|---|---|---|---|---|
| 37109 | H— | —C$_6$H$_{13}$ | K44 | N53 W |
| 37110 | H— | —C$_8$H$_{17}$ | K41.3 | C51 A57.6 N60.2 W |
| 37111 | H— | —C$_9$H$_{19}$ | K52.8 | C56.8 A67.2 W |
| 37112 | H— | —C$_{10}$H$_{21}$ | K44 | C64.9 A67.7 W |
| 37113 | H— | —C$_{11}$H$_{23}$ | K48 | C70.2 A71.6 W |
| 37114 | H— | —C$_{12}$H$_{25}$ | K52 | C72.3 W |
| 37115 | H— | —O—C$_7$H$_{15}$ | K56.4 | C71.3 A83.4 N85.1 W |
| 37116 | H— | —O—C$_8$H$_{17}$ | K69.2 | C75.8 A90.2 W |
| 37117 | H— | —O—C$_{11}$H$_{23}$ | K68 | C95 W |
| 37118 | C$_2$H$_5$—OOC— | —C$_8$H$_{17}$ 1 | K38 | C*36 I |

40

TABLE 58

| No | L | R | | Cr | LC |
|---|---|---|---|---|---|
| 9165 | C$_2$H$_5$—CHMe—CH$_2$—OOC— | —O—C$_{11}$H$_{22}$—O—H | S | K80 | C*58.9 A72.8 I |
| 9179 | C$_5$H$_{11}$— | —Cl | | K69 | N37 E |
| 9182 | C$_{10}$H$_{21}$—O— | —Cl | | K85.5 | C86.5 I |
| 9200 | CH$_3$— | —CN | | K160 | N65 E |
| 9201 | C$_2$H$_5$— | —CN | | K110 | N62 E |
| 9209 | C$_{10}$H$_{21}$— | —CN | | K64.4 | A47.9 N62.1 B |
| 9210 | C$_{11}$H$_{23}$— | —CN | | K64 | A61.4 N66.7 I |
| 9211 | C$_{12}$H$_{25}$— | —CN | | K72 | A64.7 N66 I |
| 9221 | C$_{14}$H$_{29}$—O— | —CN | | K96 | A91 I |
| 9226 | C$_7$H$_{15}$— | —O—C$_3$H$_6$—CN | | K85.5 | A70 N77 I |

| No | L | R | Cr | LC |
|---|---|---|---|---|

TABLE 58-continued

| | | | | | |
|---|---|---|---|---|---|
| 9227 | $C_7H_{15}-O-$ | $-O-C_3H_6-CN$ | | K105.5 | N102.5 U |
| 9228 | $C_5H_{11}-$ | $-O-C_5H_{10}-CN$ | | K63.4 | A53 N70 I |
| 9230 | $C_2H_5-CHMe-C_2H_4-$ | $-CN$ | S | K81 | N*23.5 B |
| 9237 | $H_2C=CH-CH_2-O-$ | $-CN$ | | K115.2 | N104.1 I |
| 9243 | $CH_3-NMe-$ | $-NO_2$ | | K217 | X220 Z |
| 9256 | $C_4H_9-$ | $-C_7H_{15}$ | | K6.2 | S-2.5 N17.5 I |
| 9257 | $C_4H_9-$ | $-C_8H_{17}$ | | K14.2 | S10.3 N16.5 I |
| 9258 | $C_4H_9-$ | $-C_9H_{19}$ | | K30 | S20.5 N27 I |
| 9259 | $C_5H_{11}-$ | $-C_6H_{13}$ | | K31.2 | S21 I |
| 9260 | $C_5H_{11}-$ | $-C_7H_{15}$ | | K27.3 | S17.5 N39.1 I |
| 9261 | $C_5H_{11}-$ | $-C_8H_{17}$ | | K8.6 | S30.5 N33.7 I |
| 9262 | $C_5H_{11}-$ | $-C_9H_{19}$ | | K28 | S37 N44.9 I |
| 9263 | $C_6H_{13}-$ | $-C_7H_{15}$ | | K19.3 | S20 N30 I |
| 9264 | $C_6H_{13}-$ | $-C_8H_{17}$ | | K22.2 | S27.8 I |
| 9265 | $C_6H_{13}-$ | $-C_9H_{19}$ | | K23.7 | S31.7 I |
| 9266 | $C_7H_{15}-$ | $-C_7H_{15}$ | | K41.6 | S35.2 N40.8 I |
| 9267 | $C_7H_{15}-$ | $-C_9H_{19}$ | | K20 | S43.8 I |
| 9271 | $CH_3-$ | $-O-CH_3$ | | K124.8 | N32.1 E |

TABLE 59

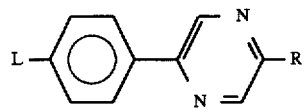

| No | L | R | | Cr | LC |
|---|---|---|---|---|---|
| 5352 | $C_{12}H_{25}-$ | $-CN$ | | K87 | A81 I |
| 5353 | $C_{13}H_{27}-$ | $-CN$ | | K87 | S80 B |
| 5355 | $C_8H_{17}-O-$ | $-CN$ | | K84 | A112 I |
| 5356 | $C_{10}H_{21}-O-$ | $-CN$ | | K70 | A111 I |
| 5357 | $C_{12}H_{25}-O-$ | $-CN$ | | K85 | A111 I |
| 5358 | $C_{12}H_{25}-$ | $-O-C_4H_9$ | | K48 | S43 I |
| 5360 | $CH_3-O-$ | $-C_8H_{17}$ | | K68 | A63 I |
| 5361 | $CH_3-O-$ | $-C_{12}H_{25}$ | | K90 | A83 I |
| 5362 | $C_8H_{17}-O-$ | $-C_8H_{17}$ | | K65 | C64 A79 I |
| 5367 | $C_{12}H_{25}-O-$ | $-O-CH_2-CHMe-C_2H_5$ | S | K63 | A45 I |
| 5369 | $C_8H_{17}-O-$ | $-COO-CH_2-CHMe-C_2H_5$ | S | K41 | S52 A60 I |
| 5370 | $C_{12}H_{25}-O-$ | $-COO-CH_2-CHMe-C_2H_5$ | S | K42 | A60 I |
| 5371 | $C_8H_{17}-O-$ | $-O-C_3H_6-CHMe-C_2H_5$ | S | K42 | C*61 A66 I |
| 5372 | $C_{12}H_{25}-O-$ | $-O-C_3H_6-CHMe-C_2H_5$ | S | K50 | C*63 A72 I |
| 5374 | $C_2H_5-CHMe-CH_2-O-$ | $-O-C_{12}H_{25}$ | S | K56 | A46 I |
| 5376 | $C_2H_5-CHMe-CH_2-OOC-$ | $-O-C_{12}H_{25}$ | S | K58 | C*45 A49 I |
| 5377 | $C_2H_5-CHMe-C_3H_6-OOC-$ | $-O-C_{12}H_{25}$ | 1 | K? | A<? I |
| 5378 | $C_3H_7-CHMe-C_4H_8-O-$ | $-C_8H_{17}$ | 2 | K48 | C56.5 I |
| 5379 | $C_2H_5-CHMe-C_5H_{10}-O-$ | $-C_8H_{17}$ | 2 | K49 | C62 I |

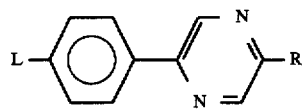

| No | L | R | Cr | LC |
|---|---|---|---|---|
| 5381 | $C_5H_{11}-CH=CH-CH_2-O-$ | $-C_8H_{17}$ | K48 | C77 I |

TABLE 60

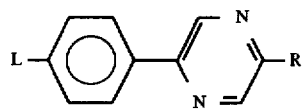

| No | L | R | | Cr | LC |
|---|---|---|---|---|---|
| 5352 | $C_{12}H_{25}-$ | $-CN$ | | K87 | A81 I |
| 5353 | $C_{13}H_{27}-$ | $-CN$ | | K87 | S80 B |
| 5355 | $C_8H_{17}-O-$ | $-CN$ | | K84 | A112 I |
| 5356 | $C_{10}H_{21}-O-$ | $-CN$ | | K70 | A111 I |
| 5357 | $C_{12}H_{25}-O-$ | $-CN$ | | K85 | A111 I |
| 5358 | $C_{12}H_{25}-$ | $-O-C_4H_9$ | | K48 | S43 I |
| 5360 | $CH_3-O-$ | $-C_8H_{17}$ | | K68 | A63 I |
| 5361 | $CH_3-O-$ | $-C_{12}H_{25}$ | | K90 | A83 I |
| 5362 | $C_8H_{17}-O-$ | $-C_8H_{17}$ | | K65 | C64 A79 I |
| 5367 | $C_{12}H_{25}-O-$ | $-O-CH_2-CHMe-C_2H_5$ | S | K63 | A45 I |
| 5369 | $C_8H_{17}-O-$ | $-COO-CH_2-CHMe-C_2H_5$ | S | K41 | S52 A60 I |
| 5370 | $C_{12}H_{25}-O-$ | $-COO-CH_2-CHMe-C_2H_5$ | S | K42 | A60 I |
| 5371 | $C_8H_{17}-O-$ | $-O-C_3H_6-CHMe-C_2H_5$ | S | K42 | C*61 A66 I |
| 5372 | $C_{12}H_{25}-O-$ | $-O-C_3H_6-CHMe-C_2H_5$ | S | K50 | C*63 A72 I |
| 5374 | $C_2H_5-CHMe-CH_2-O-$ | $-O-C_{12}H_{25}$ | S | K56 | A46 I |
| 5376 | $C_2H_5-CHMe-CH_2-OOC-$ | $-O-C_{12}H_{25}$ | S | K58 | C*45 A49 I |
| 5377 | $C_2H_5-CHMe-C_3H_6-OOC-$ | $-O-C_{12}H_{25}$ | 1 | K? | A<? I |
| 5378 | $C_3H_7-CHMe-C_4H_8-O-$ | $-C_8H_{17}$ | 2 | K48 | C56.5 I |
| 5379 | $C_2H_5-CHMe-C_5H_{10}-O-$ | $-C_5H_{17}$ | 2 | K49 | C62 I |

TABLE 61

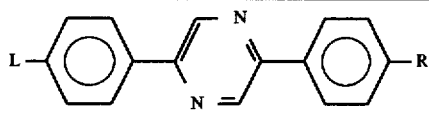

| No | L | R | Cr | LC |
|---|---|---|---|---|
| 25427 | $CH_3-$ | $-CN$ | K196 | A221 N296 I |
| 25428 | $C_2H_5-$ | $-CN$ | K190 | A197 N278 I |
| 25429 | $C_3H_7-$ | $-CN$ | K169 | A179 N277 I |
| 25430 | $C_4H_9-$ | $-CN$ | K129 | A139 N256 I |
| 25431 | $C_5H_{11}-$ | $-CN$ | K131 | A140 N263 I |
| 25432 | $C_6H_{13}-$ | $-CN$ | K107 | A125 N225 U |
| 25433 | $C_7H_{15}-$ | $-CN$ | K110 | A132 N242 I |
| 25434 | $C_8H_{17}-$ | $-CN$ | K125 | A133 N240 I |
| 25435 | $C_9H_{19}-$ | $-CN$ | K105 | A107 N232 I |
| 25436 | $C_{12}H_{25}-$ | $-CN$ | K109 | C119 A227 I |
| 25437 | $C_{16}H_{33}-$ | $-CN$ | K106 | C119 A221 I |
| 25438 | $CH_3-O-$ | $-CN$ | K182 | S169 N321 I |
| 25439 | $C_7H_{15}-O-$ | $-CN$ | K97 | X267 I |
| 25440 | $C_8H_{17}-O-$ | $-CN$ | K96 | X270 I |
| 25441 | $C_9H_{19}-O-$ | $-CN$ | K102 | X263 I |
| 25442 | $C_{10}H_{21}-O-$ | $-CN$ | K104 | X252 I |
| 25443 | $C_{11}H_{23}-O-$ | $-CN$ | K109 | X263 I |
| 25444 | $C_{12}H_{25}-O-$ | $-CN$ | K105 | X252 I |
| 25445 | $C_{13}H_{27}-O-$ | $-CN$ | K103 | X246 I |
| 25450 | $C_4H_9-$ | $-C_4H_9$ | K161.3 | C166.4 N181.9 I |
| 25451 | $C_5H_{11}-$ | $-C_5H_{11}$ | K134.3 | C173.6 A182.2 N191.3 I |
| 25452 | $C_6H_{13}-$ | $-C_6H_{13}$ | K116.1 | C172.3 A179.2 I |

TABLE 62

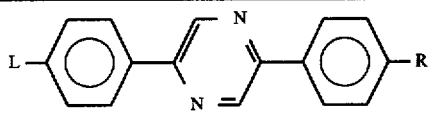

| No | L | R | Cr | LC |
|---|---|---|---|---|
| 25453 | $C_7H_{15}-$ | $-C_7H_{15}$ | K109.6 | C175 A187 I |
| 25454 | $C_8H_{17}-$ | $-C_8H_{17}$ | K104.6 | C178 A187 I |
| 25455 | $C_9H_{19}-$ | $-C_9H_{19}$ | K108.8 | C177 I |
| 25456 | $C_{10}H_{21}-$ | $-C_{10}H_{21}$ | K112 | S106 C170.5 I |
| 25458 | $C_2H_5-$ | $-O-CH_3$ | K162 | A163 N229 I |
| 25460 | $C_4H_9-$ | $-O-CH_3$ | K138 | A139 N230 I |
| 25462 | $C_6H_{13}-$ | $-O-CH_3$ | K137 | A138 N206 U |
| 25464 | $C_8H_{17}-$ | $-O-CH_3$ | K135 | A136 N225 U |
| 25466 | $C_{12}H_{25}-$ | $-O-CH_3$ | K131 | A169 N180 I |
| 25467 | $C_{16}H_{33}-$ | $-O-CH_3$ | K127 | A175 I |
| 25469 | $C_5H_{11}-$ | $-OOC-C_3H_7$ | K158 | S200 N219 I |
| 25473 | $C_4H_9-O-$ | $-O-C_4H_9$ | K170.3 | C218 N246 I |
| 25474 | $C_5H_{11}-O-$ | $-O-C_5H_{11}$ | K153.4 | C211 N224 I |
| 25475 | $C_6H_{13}-O-$ | $-O-C_6H_{13}$ | K135.7 | B139.6 C212 N220 I |
| 25476 | $C_7H_{15}-O-$ | $-O-C_7H_{15}$ | K126 | B128.5 C211 N212 I |
| 25477 | $C_8H_{17}-O-$ | $-O-C_8H_{17}$ | K118.8 | B121.1 C209 I |
| 25478 | $C_9H_{19}-O-$ | $-O-C_9H_{19}$ | K118.7 | C204 I |
| 25479 | $C_{10}H_{21}-O-$ | $-O-C_{10}H_{21}$ | K113 | C201 I |
| 25481 | $C_8H_{17}-O-$ | $-COO-CHMe-C_2H_5$ | l K11 | C*161 A184 I |
| 25482 | $C_{10}H_{21}-O-$ | $-COO-CHMe-C_6H_{13}$ | l K138 | C*139 A162 I |

TABLE 63

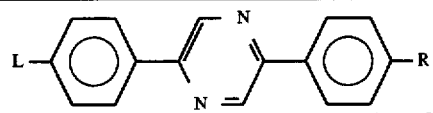

| No | L | R | Cr | LC |
|---|---|---|---|---|
| 25483 | $C_{12}H_{25}-$ | $-O-CH_2-CHMe-C_2H_5$ | S K67 | S100 C*155 A157 I |
| 25484 | $C_{10}H_{21}-$ | $-COO-CH_2-CHMe-C_2H_5$ | S K85 | C*120 A166 I |
| 25485 | $C_{12}H_{25}-$ | $-COO-CH_2-CHMe-C_2H_5$ | S K95 | C*130 A162 I |
| 25486 | $C_{16}H_{33}-$ | $-COO-CH_2-CHMe-C_2H_5$ | S K95 | C*100 A165 I |
| 25487 | $C_7H_{15}-O-$ | $-COO-CH_2-CHMe-C_2H_5$ | S K126 | C*175 A200 I |
| 25488 | $C_8H_{17}-O-$ | $-COO-CH_2-CHMe-C_2H_5$ | S K109 | C*131 A182 I |
| 25489 | $C_9H_{19}-O-$ | $-COO-CH_2-CHMe-C_2H_5$ | S K113 | C*171 A199 I |
| 25490 | $C_{10}H_{21}-O-$ | $-COO-CH_2-CHMe-C_2H_5$ | S K98 | C*168 A187 I |
| 25491 | $C_{11}H_{23}-O-$ | $-COO-CH_2-CHMe-C_2H_5$ | S K90 | C*160 A193 I |
| 25492 | $C_{12}H_{25}-O-$ | $-COO-CH_2-CHMe-C_2H_5$ | S K110 | C*166 A186 I |
| 25493 | $C_{13}H_{27}-O-$ | $-COO-CH_2-CHMe-C_2H_5$ | S K100 | C*160 A185 I |
| 25494 | $C_{10}H_{21}-O-$ | $-COO-C_3H_6-CHMe-C_2H_5$ | S K68 | C*168 A199 I |

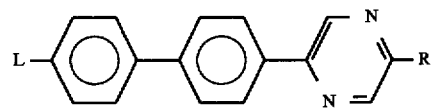

| No | L | R | Cr | LC |
|---|---|---|---|---|
| 26944 | F– | $-O-C_4H_9$ | K118.7 | A202.3 I |
| 26945 | F– | $-O-C_5H_{11}$ | K120 | A204 I |
| 26946 | F– | $-O-C_6H_{13}$ | K110.5 | A195.5 I |
| 26947 | F– | $-O-C_7H_{15}$ | K117.1 | A191.1 I |
| 26948 | F– | $-O-C_8H_{17}$ | K115.6 | A188 I |
| 26949 | F– | $-O-C_9H_{19}$ | K116.2 | A179.4 I |
| 26950 | F– | $-O-C_{10}H_{21}$ | K117.1 | A178.6 I |
| 26951 | F– | $-O-C_{12}H_{25}$ | K121.3 | A170.5 I |
| 26952 | $C_3H_7-$ | $-O-C_4H_9$ | K91.7 | E149.2 B161 A198.7 N201.3 I |
| 26953 | $C_3H_7-$ | $-O-C_5H_{11}$ | K92.4 | E143 B156 A191.2 N192.5 I |
| 26954 | $C_3H_7-$ | $-O-C_6H_{13}$ | K92.6 | E135.9 B149.8 A191.4 N192.1 I |
| 26955 | $C_3H_7-$ | $-O-C_7H_{15}$ | K77.3 | E132.7 B147.8 A187.9 I |

TABLE 63-continued

| 26956 | $C_3H_7-$ | $-O-C_8H_{17}$ | K86.8 | E130.5 B149.9 A198.5 U |
| 26957 | $C_3H_7-$ | $-O-C_9H_{19}$ | K91.8 | E120.7 B138.3 N180.5 I |
| 26958 | $C_3H_7-$ | $-O-C_{10}H_{21}$ | K93.2 | E118 B135 N181 I |
| 26959 | $C_3H_7-$ | $-O-C_{12}H_{25}$ | K105.4 | E108 B128.4 N171.7 I |

TABLE 64

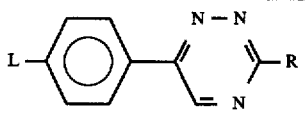

| No | L | R | Cr | LC |
|---|---|---|---|---|
| 5543 | $C_4H_9-$ | $-C_6H_{13}$ | K57.5 | A56.5 I |
| 5544 | $C_6H_{13}-$ | $-C_4H_9$ | K45 | A61.5 I |
| 5545 | $C_6H_{13}-$ | $-C_5H_{11}$ | K31 | A68 I |
| 5546 | $C_6H_{13}-$ | $-C_6H_{13}$ | K44 | A68 I |
| 5547 | $C_6H_{13}-$ | $-C_7H_{15}$ | K43 | A69.5 I |
| 5548 | $C_7H_{15}-$ | $-C_7H_{15}$ | K41 | A72 I |
| 5549 | $C_8H_{17}-$ | $-C_4H_9$ | K36.5 | A64.5 I |
| 5550 | $C_8H_{17}-$ | $-C_5H_{11}$ | K37 | B46 A71 I |
| 5551 | $C_8H_{17}-$ | $-C_6H_{13}$ | K44 | B49 A72 I |
| 5552 | $C_8H_{17}-$ | $-C_7H_{15}$ | K50 | B51.5 A73.5 I |
| 5553 | $C_9H_{19}-$ | $-C_4H_9$ | K37 | A63.5 I |
| 5554 | $C_9H_{19}-$ | $-C_5H_{11}$ | K42 | A78 I |
| 5555 | $C_9H_{19}-$ | $-C_6H_{13}$ | K34 | A73 I |
| 5556 | $C_9H_{19}-$ | $-C_7H_{15}$ | K44 | A73 I |
| 5560 | $C_5H_{11}-O-$ | $-C_4H_9$ | K55 | A101 I |
| 5561 | $C_5H_{11}-O-$ | $-C_6H_{13}$ | K58 | A103 I |
| 5562 | $C_6H_{13}-O-$ | $-CH_3$ | K99 | A101 I |
| 5563 | $C_6H_{13}-O-$ | $-C_4H_9$ | K57 | A100 I |
| 5564 | $C_6H_{13}-O-$ | $-C_6H_{13}$ | K55 | A103 I |

TABLE 65

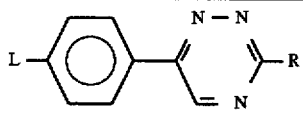

| No | L | R | Cr | LC |
|---|---|---|---|---|
| 5567 | $C_2H_5-CHMe-CH_2-O-$ | $-C_8H_{17}$ | S K57.8 | A53.9 I |
| 5568 | $C_2H_5-CHMe-C_3H_6-O-$ | $-C_4H_9$ | S K42.5 | C*66.2 A77.3 I |
| 5569 | $C_2H_5-CHMe-C_3H_6-O-$ | $-C_5H_{11}$ | S K50.5 | C*76.5 A82 I |
| 5570 | $C_2H_5-CHMe-C_3H_6-O-$ | $-C_6H_{13}$ | S K49 | C*75.1 A80.1 I |
| 5571 | $C_2H_5-CHMe-C_3H_6-O-$ | $-C_7H_{15}$ | S K55 | C*77.1 A82 I |
| 5572 | $C_2H_5-CHMe-C_3H_6-O-$ | $-C_8H_{17}$ | S K48 | C*72.1 A76.9 I |
| 5573 | $C_2H_5-CHMe-C_4H_8-O-$ | $-C_6H_{13}$ | S K34.5 | C*70.7 A78.1 I |
| 5574 | $C_2H_5-CHMe-C_4H_8-O-$ | $-C_8H_{17}$ | S K52.5 | C*70 A73 I |
| 5575 | $C_2H_5-CHMe-C_4H_8-COO-$ | $-C_8H_{17}$ | S K68 | C*79.6 A80.8 I |
| 5576 | $C_2H_5-CHMe-C_5H_{10}-O-$ | $-C_2H_5$ | S K33 | A85.4 I |
| 5577 | $C_2H_5-CHMe-C_5H_{10}-O-$ | $-C_3H_7$ | S K34.5 | A93.4 I |
| 5578 | $C_2H_5-CHMe-C_5H_{10}-O-$ | $-C_4H_9$ | S K29.8 | C*57.1 A85 I |
| 5579 | $C_2H_5-CHMe-C_5H_{10}-O-$ | $-C_5H_{11}$ | S K44 | C*76.5 A89.5 I |
| 5580 | $C_2H_5-CHMe-C_5H_{10}-O-$ | $-C_6H_{13}$ | S K37 | C*79.3 A85.7 I |
| 5581 | $C_2H_5-CHMe-C_5H_{10}-O-$ | $-C_7H_{15}$ | S K50.5 | C*86.9 A88.8 I |
| 5582 | $C_2H_5-CHMe-C_5H_{10}-O-$ | $-C_8H_{19}$ | S K44.5 | C*81.2 A84.6 I |
| 5583 | $C_2H_5-CHMe-C_5H_{10}-O-$ | $-C_9H_{19}$ | S K59.5 | C*86 I |
| 5584 | $C_2H_5-CHMe-C_5H_{10}-O-$ | $-C_{10}H_{21}$ | S K51.5 | C*81.2 I |

TABLE 66

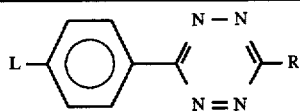

| No | L | R | Cr | LC |
|---|---|---|---|---|
| 5654 | $C_5H_{11}-O-$ | $-C_6H_{13}$ | K65 | C58.5 I |
| 5655 | $C_5H_{11}-O-$ | $-C_7H_{15}$ | K49 | C52.5 N63 I |
| 5656 | $C_6H_{13}-O-$ | $-C_5H_{11}$ | K55 | A68 I |
| 5657 | $C_6H_{13}-O-$ | $-C_7H_{15}$ | K58 | C67 A74 N76 I |
| 5658 | $C_4H_9-O-$ | $-O-C_4H_9$ | K75.5 | S57.5 N74 I |
| 5659 | $C_4H_9-O-$ | $-O-C_6H_{13}$ | K70 | S68.5 N80 I |
| 5660 | $C_5H_{11}-O-$ | $-O-C_4H_9$ | K53.5 | S61 N71 I |
| 5661 | $C_5H_{11}-O-$ | $-O-C_6H_{13}$ | K55.5 | S70 S72.5 N82 I |
| 5676 | $C_7H_{15}-COO-$ | $-C_6H_{13}$ | K56 | C50.5 A65 I |

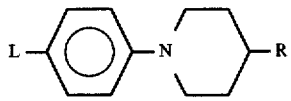

| No | L | R | Cr | LC |
|---|---|---|---|---|
| 7081 | $O_2N-$ | $-OOC-C_{10}H_{20}-Si_4O_4Me_7-cy$ | K? | A50 I |
| 7083 | $F-$ | $-C_2H_5$ | K<20 | N-36.2 I |
| 7084 | $F-$ | $-C_3H_7$ | K<20 | N-14.6 I |
| 7089 | $NC-$ | $-C_6H_{13}$ | K29.7 | N14.5 I |
| 7097 | $C_4H_9-$ | $-C_6H_{13}$ | K20 | B44 I |
| 7098 | $C_4H_9-O-$ | $-C_6H_{13}$ | K40 | B78 I |
| 7099 | $CH_3-OOC-$ | $-C_5H_{11}$ | K86.5 | A90.5 I |
| 7100 | $C_3H_7-OOC-$ | $-C_5H_{11}$ | K37.8 | A68 I |
| 7101 | $C_4H_9-OOC-$ | $-C_5H_{11}$ | K42 | A57.8 I |
| 7102 | $C_5H_{11}-OOC-$ | $-C_5H_{11}$ | K45.5 | A59 I |

TABLE 67

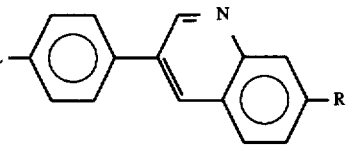

| No | L | R | Cr | LC |
|---|---|---|---|---|
| 7260 | $C_5H_{11}-$ | $-O-C_8H_{17}$ | K72 | A114 I |
| 7261 | $C_4H_9-O-$ | $-C_4H_9$ | K79 | C96 N108 I |
| 7262 | $C_5H_{11}-O-$ | $-C_4H_9$ | K86 | C101 N106.5 I |
| 7264 | $C_4H_9-O-$ | $-O-C_4H_9$ | K104 | C112 N142 N150 I |
| 7265 | $C_4H_9-O-$ | $-O-C_8H_{17}$ | K92 | C95 A140 N142.5 I |
| 7266 | $C_9H_{19}-O-$ | $-O-CH_3$ | K99 | A116 N127 I |
| 7267 | $C_9H_{19}-O-$ | $-O-C_8H_{17}$ | K74.5 | C135.5 A144 I |
| 7268 | $C_4H_9-S-$ | $-O-C_8H_{17}$ | K71.8 | A119 I |

TABLE 68

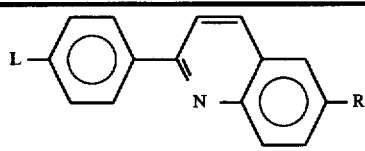

| No | L | R | Cr | LC |
|---|---|---|---|---|
| 7276 | $C_2H_5-O-$ | $-CN$ | K150 | S144 N189 I |
| 7277 | $C_8H_{17}-$ | $-C_6H_{13}$ | K68 | C106 N116 I |
| 7281 | $C_5H_{11}-$ | $-O-C_4H_9$ | K77 | S76 N118 I |
| 7285 | $C_5H_{11}-O-$ | $-C_5H_{11}$ | K73 | C77 N118 I |
| 7286 | $C_5H_{11}-O-$ | $-C_6H_{13}$ | K73 | C88 N114 I |
| 7287 | $C_5H_{11}-O-$ | $-C_7H_{15}$ | K71 | C96 A98 N118 I |
| 7288 | $C_5H_{11}-O-$ | $-C_8H_{17}$ | K73 | C92 A105 N112 I |
| 7289 | $C_6H_{13}-O-$ | $-C_5H_{11}$ | K68 | C93 N125 I |
| 7290 | $C_6H_{13}-O-$ | $-C_6H_{13}$ | K66 | C98 N117 I |
| 7291 | $C_6H_{13}-O-$ | $-C_7H_{15}$ | K65 | C104 A106 N121 I |
| 7292 | $C_6H_{13}-O-$ | $-C_8H_{17}$ | K69 | C104 A113 N117 I |
| 7293 | $C_7H_{15}-O-$ | $-C_5H_{11}$ | K73 | C98 N121 I |
| 7294 | $C_7H_{15}-O-$ | $-C_6H_{13}$ | K70 | C105 N116 I |
| 7295 | $C_7H_{15}-O-$ | $-C_7H_{15}$ | K70 | C109 A113 N120 I |
| 7296 | $C_7H_{15}-O-$ | $-C_8H_{17}$ | K71 | C109 A115 N116 I |
| 7297 | $C_8H_{17}-O-$ | $-C_5H_{11}$ | K72 | C104 N120 I |
| 7298 | $C_8H_{17}-O-$ | $-C_6H_{13}$ | K68 | C106 N116 I |
| 7299 | $C_8H_{17}-O-$ | $-C_7H_{15}$ | K70 | C109 A117 N120 I |

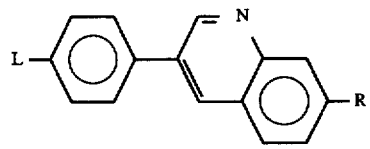

| No | L | R | Cr | LC |
|---|---|---|---|---|
| 7260 | $C_5H_{11}-$ | $-O-C_8H_{17}$ | K72 | A114 I |
| 7261 | $C_4H_9-O-$ | $-C_4H_9$ | K79 | C96 N108 I |
| 7262 | $C_5H_{11}-O-$ | $-C_4H_9$ | K86 | C101 N106.5 I |
| 7264 | $C_4H_9-O-$ | $-O-C_4H_9$ | K104 | C112 A142 N150 I |
| 7265 | $C_4H_9-O-$ | $-O-C_8H_{17}$ | K92 | C95 A140 N142.5 I |
| 7266 | $C_9H_{19}-O-$ | $-O-CH_3$ | K99 | A116 N127 I |
| 7267 | $C_9H_{19}-O-$ | $-O-C_8H_{17}$ | K74.5 | C135.5 A144 I |
| 7268 | $C_4H_9-S-$ | $-O-C_8H_{17}$ | K71.8 | A119 I |

TABLE 69

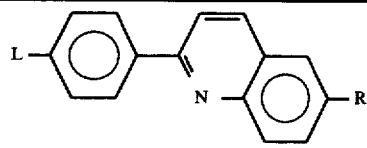

| No | L | R | Cr | LC |
|---|---|---|---|---|
| 7300 | $C_8H_{17}-O-$ | $-C_8H_{17}$ | K69 | C113 A118 I |
| 7301 | $C_9H_{19}-O-$ | $-C_5H_{11}$ | K76 | C107 A109 N118 I |
| 7302 | $C_9H_{19}-O-$ | $-C_6H_{13}$ | K76 | C111 A113 N116 I |
| 7303 | $C_9H_{19}-O-$ | $-C_7H_{15}$ | K76 | C113 A119 I |
| 7304 | $C_9H_{19}-O-$ | $-C_8H_{17}$ | K75 | C114 A117 I |
| 7305 | $C_{10}H_{21}-O-$ | $-C_5H_{11}$ | K77 | C107 A113 N118 I |
| 7306 | $C_{10}H_{21}-O-$ | $-C_6H_{13}$ | K75 | C110 A114 N116 I |
| 7307 | $C_{10}H_{21}-O-$ | $-C_7H_{15}$ | K74 | C114 A119 I |
| 7308 | $C_{10}H_{21}-O-$ | $-C_8H_{17}$ | K68 | C114 A116 I |
| 7309 | $C_{11}H_{23}-O-$ | $-C_5H_{11}$ | K83 | C105 A114 N116 I |
| 7310 | $C_{11}H_{23}-O-$ | $-C_6H_{13}$ | K82 | C110 A115 I |
| 7311 | $C_{11}H_{23}-O-$ | $-C_7H_{15}$ | K81 | C113 A118 I |
| 7312 | $C_{11}H_{23}-O-$ | $-C_8H_{17}$ | K80 | C115 A117 I |
| 7313 | $C_{12}H_{25}-O-$ | $-C_5H_{11}$ | K83 | C104 A114 N116 I |
| 7314 | $C_{12}H_{25}-O-$ | $-C_6H_{13}$ | K103 | C108 A113 I |
| 7315 | $C_{12}H_{25}-O-$ | $-C_7H_{15}$ | K79 | C112 A118 I |
| 7316 | $C_{12}H_{25}-O-$ | $-C_8H_{17}$ | K79 | C113 A115 I |
| 7317 | $C_5H_{11}-CFMe-COO-$ | $-C_8H_{17}$ | 1 K65.3 | S63.5 I |

TABLE 70

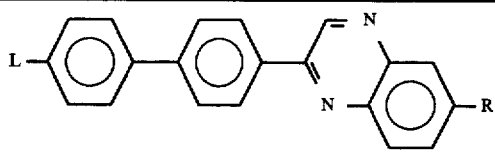

| No | L | R | Cr | LC |
|---|---|---|---|---|
| 27333 | $CH_3-$ | $-H$ | K153 | A151.5 N163.5 I |
| 27334 | $C_2H_5-$ | $-H$ | K142 | A164 I |
| 27335 | $C_3H_7-$ | $-H$ | K125 | A175.5 I |
| 27336 | $C_4H_9-$ | $-H$ | K120.5 | A170 I |
| 27337 | $C_5H_{11}-$ | $-H$ | K113 | A175 I |
| 27338 | $C_6H_{13}-$ | $-H$ | K99.5 | A176 I |
| 27339 | $C_7H_{15}-$ | $-H$ | K86 | E88 A170 I |
| 27340 | $C_8H_{17}-$ | $-H$ | K60 | E82 A176 I |
| 27341 | $C_9H_{19}-$ | $-H$ | K61 | S82 A173 I |
| 27342 | $C_{10}H_{21}-$ | $-H$ | K53 | E83 A171 I |
| 27343 | $CH_3-O-$ | $-H$ | K169 | A163 N203 I |
| 27344 | $C_2H_5-O-$ | $-H$ | K175 | A202 N216 I |
| 27345 | $C_3H_7-O-$ | $-H$ | K157 | A204 I |
| 27346 | $C_5H_{11}-O-$ | $-H$ | K145 | E130 A206 I |
| 27347 | $C_8H_{17}-O-$ | $-H$ | K96 | E115 A195 I |
| 27348 | $C_{10}H_{21}-O-$ | $-H$ | K98 | E120 A194 I |
| 27349 | $C_{16}H_{33}-O-$ | $-H$ | K109 | E106 A182.5 I |
| 27351 | $C_5H_{11}$-Oxazolidinyl-N-oxy-$C_4H_8-O-$ | $-H$ | 2 K118 | C101 A108 I |
| 27352 | $C_8H_{17}$-Oxazolidinyl-N-oxy-$C_7H_{14}-O-$ | $-H$ | 2 K79 | E99 C119 A134 I |
| 27353 | $CH_3$-Oxazolidinyl-N-oxy-$C_8H_{16}-O-$ | $-H$ | 2 K113 | C123 A158.5 I |

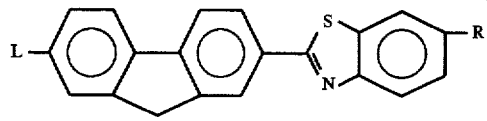

| No | L | R | Cr | LC |
|---|---|---|---|---|
| 8797 | $C_6H_{13}-$ | $-C_6H_{13}$ | K170 | S172 A236 I |

TABLE 71

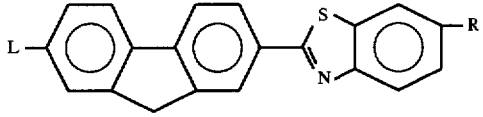

| No | L | R | Cr | LC |
|----|---|---|----|----|
| 8797 | C$_6$H$_{13}$— | —C$_6$H$_{13}$ | K170 | S172 A236 I |

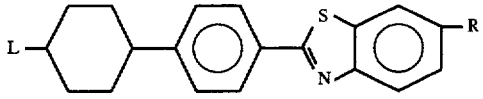

| No | L | R | Cr | LC |
|----|---|---|----|----|
| 28635 | C$_5$H$_{11}$— | —C$_6$H$_{13}$ | K67 | S125 A204 N214 I |

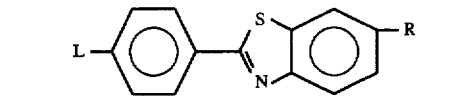

| No | L | R | Cr | LC |
|----|---|---|----|----|
| 7557 | C$_8$H$_{17}$—O— | —F | K71.5 | A128.5 I |
| 7558 | C$_8$H$_{17}$—O— | —Cl | K72 | E94.5 A164 I |
| 7559 | C$_8$H$_{17}$—O— | —Br | K75.5 | E107.5 A149.5 I |
| 7561 | C$_6$H$_{13}$— | —C$_6$H$_{13}$ | K54 | A45 N56 I |
| 7562 | C$_8$H$_{17}$— | —C$_6$H$_{13}$ | K62 | A69 I |
| 7563 | C$_8$H$_{17}$—O— | —C$_6$H$_{13}$ | K55 | C106 I |
| 7570 | C$_8$H$_{17}$—O— | —O—C$_4$H$_9$ | K70.8 | S99.8 N123.1 I |
| 7572 | C$_{12}$H$_{25}$—O— | —O—CH$_3$ | K90.7 | S96.9 N113.4 I |

EXAMPLE A1

44.6 g (0.34 mol) of 4-cyanobenzaldehyde and 54.4 g (0.64 mol) of o-aminobenzenethiol were dissolved in 300 ml of dimethyl sulfoxide, and the temperature of the solution was raised to 140° C. The produced water and the dimethyl sulfoxide were distilled off. After heating for one hr. the residue was cooled, water was added thereto, and the resultant precipitate was collected by filtration and washed with ethanol. The crude crystal thus obtained was recrystallized from ethyl acetate to give 2-(4'-cyanophenyl) benzothiazole. 22.4 g (0.095 mol) of the compound was dissolved in 250 ml of acetic acid, and 18.6 g (0.116 mol) of bromine was dropwise added thereto. As soon as bromine was added, a yellow bromine adduct was produced. Subsequently, 150 ml of water was added, and the mixture was stirred at 80° C. for 2 hr. It was then cooled, and the resultant precipitate was collected by filtration and washed with ethanol. The crude product thus obtained was recrystallized from ethyl acetate.

A 60% by weight dispersion of 0.8 g (0.02 mol) of sodium hydride in an oil was suspended in 50 ml of ether, 3.22 g (0.022 mol) of 1-octanethiol was dropwise added thereto, and the mixture was refluxed for 30 min. Thereafter, the ether was distilled off, 50 ml of N,N-dimethylimidazolidinone was added to the residue, and the temperature of the system was raised to 60° C. 0.01 mol of 2-(4'-cyanophenyl)-6-bromobenzothiazole was added to the solution, and stirring was continued for one hr. The solution was cooled, water was added thereto, and the resultant precipitate was collected by filtration and washed with ethanol. The product thus obtained was recrystallized from a hexane/ethyl acetate mixed solution to give a compound represented by the following formula:

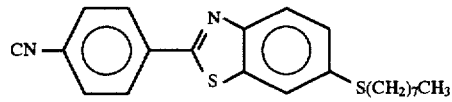

EXAMPLE A2

1.31 g (0.01 mol) of 4-cyanobenzaldehyde, 2.5 g (0.01 mol) of 2-amino-6-hexyloxybenzothiazole, and 30 ml of ethanol were heated at 70° C. for 2 hr. The reaction mixture was then cooled to room temperature, and the resultant solid matter was collected by filtration and recrystallized from ethanol to give a compound represented by the following formula:

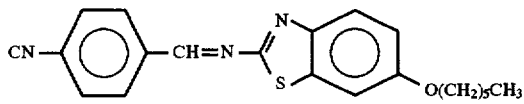

EXAMPLE A3

2.21 g (0.01 mol) of 2,5-diamino-1,4-benzenedithiol/dihydrochloric acid adduct, 5.34 g (0.024 mol) of 4-hexyloxybenzoic acid, 3 g of phosphorus pentaoxide, and 50 ml of methanesulfonic acid were allowed to react at 90° C. for one hr and then heated at 80° C. for 5 hr. The resultant product was collected by filtration and recrystallized from N-methylpyrrolidone to give a compound represented by the following formula:

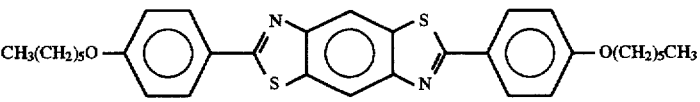

EXAMPLE A4

2.56 g (0.01 mol) of 2,6-dimercaptobenzo(1,2-d: 5,6-d') bisthiazole, 4.54 g (0.02 mol) of 4-hexyloxybenzyl chloride, 1.2 g of potassium carbonate, and 15 ml of N-methylpyrrolidone were heated at 80° C. for 3 hr. The reaction mixture was poured into water, and the resultant solid matter was collected by filtration and washed with water, methanol, and chloroform. It was then recrystallized from benzene to give a compound represented by the following formula:

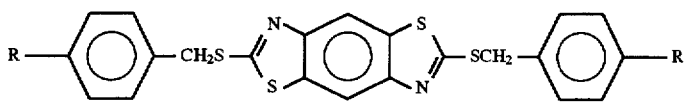

wherein R=CH$_3$(CH$_2$)$_5$O.

EXAMPLE A5

The procedure of Example A1 was repeated to prepare liquid crystalline compounds represented by the general formula (A) wherein R$_1$ and R$_2$ represent the following groups. The liquid crystalline compounds thus obtained had the same properties as the liquid crystalline compound prepared in Example A1.

| Example | R$_1$ | R$_2$ |
|---------|-------|-------|
| A5-1 | CH$_3$(CH$_2$)$_9$O | CN |
| A5-2 | CH$_3$CH$_2$C*H(CH$_3$)CH$_2$O | CN |
| A5-3 | CH$_3$(CH$_2$)$_5$O | O(CH$_2$)$_9$CH$_3$ |
| A5-4 | NO$_2$ | S(CH$_2$)$_7$CH$_3$ |
| A5-5 | NO$_2$ | O(CH$_2$)$_7$CH$_3$ |
| A5-6 | F | O(CH$_2$)$_9$CH$_3$ |

EXAMPLE A6

The procedure of Example A2 was repeated to prepare liquid crystalline compounds represented by the general formula (B) wherein R$_1$ and R$_2$ represent the following groups. The liquid crystalline compounds thus obtained had the same properties as the liquid crystalline compound prepared in Example A2.

| Example | R$_1$ | R$_2$ | Z |
|---------|-------|-------|---|
| A6-1 | NO$_2$ | O(CH$_2$)$_9$CH$_3$ | CH=N |
| A6-2 | CH$_3$(CH$_2$)$_5$O | O(CH$_2$)$_5$CH$_3$ | COO |
| A6-3 | CH$_3$CH$_2$C*H(CH$_3$)CH$_2$O | O(CH$_2$)$_7$CH$_3$ | CH=CH |
| A6-4 | CN | O(CH$_2$)$_6$CH$_3$ | CH=CH |
| A6-5 | CH$_3$(CH$_2$)$_9$O | O(CH$_2$)$_3$CH$_3$ | C≡C |
| A6-6 | CH$_3$(CH$_2$)$_5$O | O(CH$_2$)$_5$CH$_3$ | N=N |

EXAMPLE A7

The procedure of Example A3 was repeated to prepare liquid crystalline compounds represented by the general formula (C) wherein R$_1$ represents the following groups. The liquid crystalline compounds thus obtained had the same properties as the liquid crystalline compound prepared in Example A3.

| Example | R$_1$ |
|---------|-------|
| A7-1 | CH$_3$(CH$_2$)$_9$O |
| A7-2 | CH$_3$(CH$_2$)$_9$ |
| A7-3 | CH$_3$(CH$_2$)$_9$S |
| A7-4 | CH$_3$(CH$_2$)$_5$S |
| A7-5 | CH$_3$(CH$_2$)$_8$S |
| A7-6 | CH$_3$CH$_2$C*H(CH$_3$)CH$_2$O |

EXAMPLE A8

The procedure of Example A3 was repeated to prepare liquid crystalline compounds represented by the general formula (D) wherein R$_1$ represents the following group. The liquid crystalline compounds thus obtained had the same properties as the liquid crystalline compound prepared in Example A4.

| Example | R$_1$ | Z |
|---------|-------|---|
| A8-1 | CH$_3$(CH$_2$)$_5$O | COO |
| A8-2 | CH$_3$(CH$_2$)$_5$O | CH=N |
| A8-3 | CH$_3$CH$_2$C*H(CH$_3$)CH$_2$O | CH=CH |
| A8-4 | CH$_3$(CH$_2$)$_5$S | CH=N |
| A8-5 | CH$_3$(CH$_2$)$_3$O | N=N |
| A8-6 | CH$_3$(CH$_2$)$_9$O | COO |

According to the present invention, novel liquid crystalline compounds are provided which exhibit liquid crystallinity and, in addition, photoconductivity and fluorescence. The novel liquid crystalline compounds are useful as materials for liquid crystal displays, photosensitive materials for electrophotography and the like.

EXAMPLE B

[Synthesis of 2-(4'-heptyloxyphenyl)benzothiazole]74.2 g (0.34 mol) of 4-heptyloxybenzaldehyde and 54.4 g (0.46 mol) of o-aminobenzenethiol were dissolved in 300 ml of dimethyl sulfoxide, and the temperature of the solution was raised to 140° C. The produced water and the dimethyl sulfoxide were distilled off. After heating for one hr, the residue was cooled, water was added thereto, and the resultant precipitate was collected by filtration and washed with ethanol. The crude crystal thus obtained was recrystallized from ethyl acetate. The yield was 90%.

The above compound exhibited the following peaks in NMR spectrum:

$^1$H NMR (CDCl$_3$) δ=0.90 (3H, t, J=6.6 Hz), 1.25–1.47 (8H, m), 1.81 (2H, quint, J=6.6 Hz), 4.01 (2H, t, J=6.5 Hz), 6.97 (2H, d, J=8.5 Hz), 7.33 (1H, d, J=8.9 Hz), 7.45 (1H, t, J=8.5 Hz), 7.86 (1H, d, J=7.9 Hz), 8.01 (1H, d, J=8.9 Hz), 8.02 (2H, d, J=8.5 Hz)

Further, it exhibited the following peaks in IR (KBr disc) spectrum: 506, 568, 622, 648, 698, 730, 968, 1010, 1037, 1300, 1316, 1394, 1417, 1441, 1470, 1483, 1520, 1603, 2852, 2912 cm$^{-1}$

[Synthesis of 2-(4'-heptyloxyphenyl)-6-bromobenzothiazole]

31.0 g (0.095 mol) of 2-(4'-heptyloxyphenyl) benzothiazole was dissolved in 250 ml of acetic acid, and 18.6 g (0.116 mol) of bromine was dropwise added thereto. As soon as bromine was added, a yellow bromine adduct was produced. Subsequently, 150 ml of water was added, and the mixture was stirred at 80° C. for 2 hr. It was then cooled, and the resultant precipitate was collected by filtration and washed with ethanol. The crude product thus obtained was recrystallized from ethyl acetate. The yield was 68%.

The above compound exhibited the following peaks in NMR spectrum:

$^1$H NMR (CDCl$_3$) δ=0.90 (3H, t, J=6.6 Hz), 1.33–1.50 (8H, m), 1.81 (2H, quint, J=6.6 Hz), 4.03 (2H, t, J=6.6 Hz), 6.98 (2H, d, J=8.6 Hz), 7.55 (1H, d, J=2.0 and J2=8.6 Hz), 7.85 (1H, d, J=8.6 Hz), 7.98 (1H, d, J=2.0 Hz), 7.99 (2H, d, J=8.6 Hz)

Further, it exhibited the following peaks in IR (KBr disc) spectrum: 520, 563, 622, 666, 695, 723, 748, 859, 1015, 1040, 1090, 1115, 1224, 1393, 1438, 1474, 1488, 1520, 1541, 2855, 2922, 2937 cm$^{-1}$

[General process for synthesizing 2-(4'-alkoxyphenyl)-6-alkylthiobenzothiazole derivatives]

A 60% by weight dispersion of 0.8 g (0.02 mol) of sodium hydride in an oil was suspended in 50 ml of ether, 0.022 mol of a corresponding alkanethiol was dropwise added thereto, and the mixture was refluxed for 30 min. Thereafter, the ether was distilled off, 50 ml of N,N'-dimethylimidazolidinone was added to the residue, and the temperature of the system was raised to 600° C. 0.01 mol of 2-(4'-heptyloxyphenyl)-6-bromobenzothiazole was added to the solution, and stirring was continued for one hr. The solution was cooled, water was added thereto, and the resultant precipitate was collected by filtration and washed with ethanol. The crude product thus obtained was recrystallized from hexane.

2-(4'-alkoxyphenyl)-6-alkylthiobenzothiazole, having the same R (heptyl group) and different R', had the following properties.

[2-(4'-heptyloxyphenyl)-6-hexylthiobenzothiazole] (yield 65%):

$^1$H NMR (CDCl$_3$) δ=0.89 (3H, t, J=6.6 Hz), 0.90 (3H, t, J=6.6 Hz), 1.27–1.47 (14H, m), 1.67 (2H, quint, J=7.2 Hz), 1.82 (2H, quint, J=6.6 Hz), 2.98 (2H, t, J=7.2 Hz), 4.02 (2H, t, J=6.6 Hz), 6.98 (2H, d, J=8.6 Hz), 7.43 (1H, dd, J1 1.7 and J2=Hz), 7.82 (1H, d, J=1.7 Hz), 7.91 (1H, d, J=8.3 Hz), 7.99 (2H, d, J=8.6 Hz)

IR (KBr disc) 520, 570, 621, 701, 727, 966, 1010, 1040, 1112, 1276, 1306, 1396, 1418, 1441, 1474, 1485, 1520, 1543, 1575, 1606, 2855, 2956 cm$^{-1}$ Heating: Cryst (80.5° C.)—SmA (103.7° C.)—iso (2° C./min)

Cooling: Iso (103.2° C.)—SmA (83.9° C.)—Cryst (5° C./min)

[2-(4'-heptyloxyphenyl)-6-octylthiobenzothiazole] (yield 54%):

$^1$H NMR (CDCl$_3$) δ=0.87 (3H, t, J=6.9 Hz), 0.90 (3H, t, J=6.6 Hz), 1.18–1.47 (18H, m), 1.67 (2H, quint, J=7.3 Hz), 1.81 (2H, quint, J=6.6 Hz), 2.97 (2H, t, J=7.3 Hz), 4.02 (2H, t, J=6.6 Hz), 6.98 (2H, d, J=8.9 Hz), 7.42 (1H, dd, J1=1.6 and J2=8.6 Hz), 7.81 (1H, d, J=1.6 Hz), 7.90 (1H, d, J=8.6 Hz), 7.98 (2H, d, J=8.9 Hz)

IR (KBr disc) 520, 570, 621, 702, 727, 774, 843, 967, 1017, 1041, 1112, 1176, 1276, 1306, 1396, 1441, 1474, 1486, 1520, 1543, 1575, 1607, 2855, 2956 cm$^{-1}$ Heating: Cryst (94.0° C.)—SmA (102.0° C.)—iso (2° C./min)

Cooling: Iso (100.3° C.)—SmA (89.8° C.)—Sm? (78.2° C.)—Cryst (5° C./min)

[2-(4'-heptyloxyphenyl)-6-decylthiobenzothiazole] (yield 63%):

$^1$H NMR (CDCl$_3$) δ=0.87 (3H, t, J=6.9 Hz), 0.90 (3H, t, J=6.6 Hz), 1.25–1.47 (22H, m), 1.66 (2H, quint, J=7.3 Hz), 1.81 (2H, quint, J=6.6 Hz), 2.96 (2H, t, J=7.3 Hz), 4.02 (2H, t, J=6.6 Hz), 6.97 (2H, d, J=8.9 Hz), 7.43 (1H, dd, J1=2.0 and J2=8.6 Hz), 7.81 (1H, d, J=2.2 Hz), 7.89 (1H, d, J=8.6 Hz), 7.98 (2H, d, J=8.9 Hz)

IR (KBr disc) 570, 812, 842, 967, 1018, 1041, 1112, 1177, 1306, 1393, 1441, 1474, 1485, 1519, 1575, 1607, 2853, 2957 cm$^{-1}$ Heating: Cryst (95.5° C.)—SmA (100.9° C.)—iso (2° C./min)

Cooling: Iso (100.6° C.)—SmA (93.1° C.)—Cryst (5° C./min)

[2-(4'-heptyloxyphenyl)-6-dodecylthiobenzothiazole] (yield 67%):

$^1$H NMR (CDCl$_3$) δ=0.87 (3H, t, J=7.0 Hz), 0.90 (3H, t, J=6.6 Hz), 1.28–1.46 (26H, m), 1.62(2H, quint, J=7.6 Hz), 1.78 (2H, quint, J=7.6 Hz), 2.97 (2H, t, J=7.6 Hz), 4.02 (2H, t, J=6.6 Hz), 6.97 (2H, d, J=8.6 Hz), 7.42 (1H, dd, J1=2.0 and J2=8.6 Hz), 7.81 (1H, d, J=2.0 Hz), 7.90 (1H, d, J=8.6 Hz), 7.98 (2H, d, J=8.6 Hz)

IR (KBr disc) 571, 812, 841, 967, 1018, 1111, 1178, 1306, 1395, 1474, 1486, 1519, 1607, 2852, 2920, 2956 cm$^{-1}$ Heating: Cryst (90.0° C.)—SmA (98.0° C.)—iso (2° C./min)

Cooling: Iso (96.1° C.)—SmA (85.7° C.)—Cryst (5° C./min)

UV-VIS λmax=327 nm (10$^{-6}$M in CCl$_3$)

PL (He—Cd Laser 324 nm) λmax=420, 438 nm

EXAMPLE C

Synthesis Example 1 of Intermediate

[Synthesis of 2-(4'-heptyloxyphenyl)benzothiazole]

74.2 g (0.34 mol) of 4-heptyloxybenzaldehyde and 54.4 g (0.46 mol) of o-aminobenzenethiol were dissolved in 300 ml of dimethyl sulfoxide, and the temperature of the solution was raised to 140° C. The produced water and the dimethyl sulfoxide were distilled off. After heating for one hr, the residue was cooled, water was added thereto, and the resultant precipitate was collected by filtration and washed with ethanol. The crude crystal thus obtained was recrystallized from ethyl acetate. The yield was 90%.

The above compound exhibited the following peaks in NMR spectrum:

$^1$H NMR (CDCl$_3$) δ=0.90 (3H, t, J=6.6 Hz), 1.25–1.47 (8H, m), 1.81 (2H, quint, J=6.6 Hz), 4.01 (2H, t, J=6.5 Hz), 6.97 (2H, d, J=8.5 Hz), 7.33 (1H, d, J=8.9 Hz), 7.45 (1H, t, J=8.5 Hz), 7.86 (1H, d, J=7.9 Hz), 8.01 (1H, d, J=8.9 Hz), 8.02 (2H, d, J=8.5 Hz)

Further, it exhibited the following peaks in IR (KBr disc) spectrum: 506, 568, 622, 648, 698, 730, 968, 1010, 1037, 1300, 1316, 1394, 1417, 1441, 1470, 1483, 1520, 1603, 2852, 2912 cm$^{-1}$ Synthesis Example 2 of Intermediate

[Synthesis of 2-(4'-heptyloxyphenyl)-6-bromobenzothiazole]

31.0 g ( 0.095 mol) of 2-(4'-heptyloxyphenyl) benzothiazole was dissolved in 250 ml of acetic acid, and 18.6 g (0.116 mol) of bromine was dropwise added thereto. As soon as bromine was added, a yellow bromine adduct was produced. Subsequently, 150 ml of water was added, and the mixture was stirred at 80° C. for 2 hr. It was then cooled, and the resultant precipitate was collected by filtration and washed with ethanol. The crude product thus obtained was recrystallized from ethyl acetate. The yield was 68%.

The above compound exhibited the following peaks in NMR spectrum:

$^1$H NMR (CDCl$_3$) δ=0.90 (3H, t, J=6.6 Hz), 1.33–1.50 (8H, m), 1.81 (2H, quint, J=6.6 Hz), 4.03 (2H, t, J=6.6 Hz), 6.98 (2H, d, J=8.6 Hz), 7.55 (1H, dd, J1=2.0 and J2=8.6 Hz), 7.85 (1H, d, J=8.6 Hz), 7.98 (1H, d, J=2.0 Hz), 7.99 (2H, d, J=8.6 Hz)

Further, it exhibited the following peaks in IR (KBr disc) spectrum: 520, 563, 622, 666, 695, 723, 748, 859, 1015, 1040, 1090, 1115, 1224, 1393, 1438, 1474, 1488, 1520, 1541, 2855, 2922, 2937 cm$^{-1}$

EXAMPLES C1 to C4

[General process for synthesizing 2-(4'-alkoxyphenyl)-6-alkylthiobenzothiazole derivatives]

A 60% by weight dispersion of 0.8 g (0.02 mol) of sodium hydride in an oil was suspended in 50 ml of ether, 0.022 mol of a corresponding alkanethiol was dropwise added thereto, and the mixture was refluxed for 30 min. Thereafter, the ether was distilled off, 50 ml of N,N'-dimethylimidazolidinone was added to the residue, and the temperature of the system was raised to 60° C. 0.01 mol of 2-(4'-heptyloxyphenyl)-6-bromobenzothiazole was added to the solution, and stirring was continued for one hr. The solution was cooled, water was added thereto, and the resultant precipitate was collected by filtration and washed with ethanol. The crude product thus obtained was recrystallized from hexane.

2-(4'-alkoxyphenyl)-6-alkylthiobenzothiazole, having the same R (heptyl group) and different R', had the following properties.

EXAMPLE C1

[2-(4'-heptyloxyphenyl)-6-hexylthiobenzothiazole] (yield 65%):

$^1$H NMR (CDCl$_3$) δ=0.89 (3H, t, J=6.6 Hz), 0.90 (3H, t, J=6.6 Hz), 1.27–1.47 (14H, m), 1.67 (2H, quint, J=7.2 Hz), 1.82 (2H, quint, J=6.6 Hz), 2.98 (2H, t, J=7.2 Hz), 4.02 (2H, t, J=6.6 Hz), 6.98 (2H, d, J=8.6 Hz), 7.43 (1H, dd, J1=1.7 and J2=8.3 Hz), 7.82 (1H, d, J=1.7 Hz), 7.91 (1H, d, J=8.3 Hz), 7.99 (2H, d, J=8.6 Hz)

IR (KBr disc) 520, 570, 621, 701, 727, 966, 1010, 1040, 1112, 1276, 1306, 1396, 1418, 1441, 1474, 1485, 1520, 1543, 1575, 1606, 2855, 2956 cm$^{-1}$ Heating: Cryst (80.5° C.)—SmA (103.7° C.)—iso (2° C./min)

Cooling: Iso (103.2° C.)—SmA (83.9° C.)—Cryst (5° C./min)

Example C2

[2-(4'-heptyloxyphenyl)-6-octylthiobenzothiazole] (yield 54%):

$^1$H NMR (CDCl$_3$) δ=0.87 (3H, t, J=6.9 Hz), 0.90 (3H, t, J=6.6 Hz), 1.18–1.47 (18H, m), 1.67 (2H, quint, J=7.3 Hz), 1.81 (2H, quint, J=6.6 Hz), 2.97 (2H, t, J=7.3 Hz), 4.02 (2H, t, J=6.6 Hz), 6.98 (2H, d, J=8.9 Hz), 7.42 (1H, dd, J1=1.6 and J2=8.6 Hz), 7.81 (1H, d, J=1.6 Hz), 7.90 (1H, d, J=8.6 Hz), 7.98 (2H, d, J=8.9 Hz)

IR (KBr disc) 520, 570, 621, 702, 727, 774, 843, 967, 1017, 1041, 1112, 1176, 1276, 1306, 1396, 1441, 1474, 1486, 1520, 1543, 1575, 1607, 2855, 2956 cm$^{-1}$ Heating: Cryst (94.0° C.)—SmA (102.0° C.)—iso (2° C./min)

Cooling: Iso (100.3° C.)—SmA (89.8° C.)—Sm? (78.2° C.) -Cryst (5° C./min)

EXAMPLE C3

[2-(4'-heptyloxyphenyl)-6-decylthiobenzothiazole] (yield 63%):

$^1$H NMR (CDCl$_3$) δ=0.87 (3H, t, J=6.9 Hz), 0.90 (3H, t, J=6.6 Hz), 1.25–1.47 (22H, m), 1.66 (2H, quint, J=7.3 Hz), 1.81 (2H, quint, J=6.6 Hz), 2.96 (2H, t, J=7.3 Hz), 4.02 (2H, t, J=6.6 Hz), 6.97 (2H, d, J=8.9 Hz), 7.43 (1H, dd, J1=2.0 and J2=8.6 Hz), 7.81 (1H, d, J=2.2 Hz), 7.89 (1H, d, J=8.6 Hz), 7.98 (2H, d, J=8.9 Hz)

IR (KBr disc) 570, 812, 842, 967, 1018, 1041, 1112, 1177, 1306, 1393, 1441, 1474, 1485, 1519, 1575, 1607, 2853, 2957 cm$^{-1}$ Heating: Cryst (95.5° C.)—SmA (100.90° C.)—iso (2° C./min)

Cooling: Iso (100.6° C.)—SmA (93.1° C.)—Cryst (5° C./min)

EXAMPLE C4

[2-(4'-heptyloxyphenyl)-6-dodecylthiobenzothiazole] (yield 67%):

$^1$H NMR (CDCl$_3$) δ=0.87 (3H, t, J=7.0 Hz), 0.90 (3H, t, J=6.6 Hz), 1.28–1.46 (26H, m), 1.62(2H, quint, J=7.6 Hz), 1.78 (2H, quint, J=7.6 Hz), 2.97 (2H, t, J=7.6 Hz), 4.02 (2H, t, J=6.6 Hz), 6.97 (2H, d, J=8.6 Hz), 7.42 (1H, dd, J1=2.0 and J2=8.6 Hz), 7.81 (1H, d, J=2.0 Hz), 7.90 (1H, d, J=8.6 Hz), 7.98 (2H, d, J=8.6 Hz)

IR (KBr disc) 571, 812, 841, 967, 1018, 1111, 1178, 1306, 1395, 1474, 1486, 1519, 1607, 2852, 2920, 2956 cm$^{-1}$ Heating: Cryst (90.0° C.)—SmA (98.0° C.)—iso (2° C./min)

Cooling: Iso (96.1° C.)—SmA (85.7° C.)—Cryst (5° C./min)

UV–VIS λmax=327 nm (10$^{-6}$M in CCl$_3$)

PL (He—Cd Laser 324 nm) λmax=420, 438 nm

EXAMPLES C5 to C10

Liquid crystalline compounds represented by the above general formula wherein R and R' represent the following groups were prepared in the same manner as in the above examples and comparative examples. All the liquid crystalline compounds thus obtained had the same properties as those prepared in Examples C1 to C4.

| Example | R | R' |
| --- | --- | --- |
| Example C5 | Hexyl group | Heptyl group |
| Example C6 | Octyl group | Nonyl group |
| Example C7 | Hexyl group | Undecynyl group |
| Example C8 | Decyl group | Tetradecyl group |
| Example C9 | Amyl group | Tridecyl group |
| Example C10 | Dodecyl group | Heptyl group |

According to the present invention, novel liquid crystalline compounds which exhibit liquid crystallinity and, in addition, photoconductivity and fluorescence. The novel liquid crystalline compounds are useful as materials for liquid crystal displays, photosensitive materials for electrophotography and the like.

We claim:

1. A process for producing a liquid crystalline compound represented by the general formula (C), comprising the step of: reacting 2 moles of a compound represented by the general formula (6) with one mole of a compound represented by the general formula (7) to obtain the liquid crystalline compound (C):

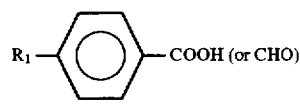 (6)

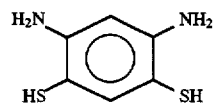 (7)

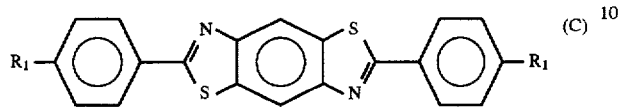 (C)

wherein $R_1$ is a $C_1$–$C_{22}$ straight-chain or branched saturated or unsaturated alkyl or alkoxy group attached to the aromatic ring through an oxygen or sulfur.

2. A process for producing a liquid crystalline compound represented by the general formula (D), comprising the step of: reacting two moles of a compound represented by the general formula (8) with one mole of a compound represented by the general formula (9) to obtain the liquid crystalline compound (D):

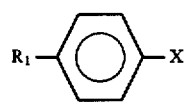 (8)

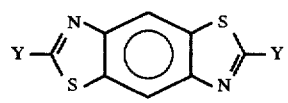 (9)

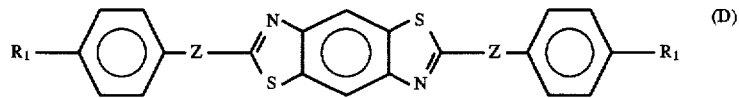 (D)

wherein $R_1$ is a $C_1$–$C_{22}$ straight-chain or branched saturated or unsaturated alkyl or alkoxy group attached to the aromatic ring through an oxygen or sulfur group; and X and Y are respectively groups which are reacted with each other to form Z selected from a —COO—, —OCO—, —N=N—, —CH=N—, —CH$_2$S—, —CH=CH—, or —C≡C— group.

3. A process for producing a liquid crystalline compound represented by the following general formula (I), comprising the steps of: reacting a 4-alkoxybenzaldehyde with o-aminobenzenethiol to synthesize a 2-(4'-alkoxyphenyl) benzothiazole; brominating the 2-(4'-alkoxyphenyl) benzothiazole to synthesize a 2-(4'-alkoxyphenyl)-6-bromobenzothiazole; and reacting the resultant bromide with an alkanethiol to obtain the liquid crystalline compound (I):

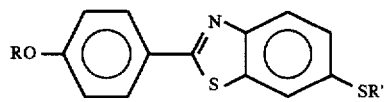 (I)

wherein R represents a $C_4$–$C_{20}$ alkyl group; and R' represents a $C_4$–$C_{20}$ alkyl group, provided that the total number of carbon atoms contained in R and R' is 10 or more.

4. A liquid crystalline compound represented by the following general formula (II):

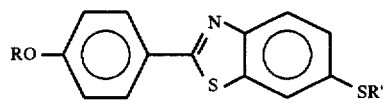 (II)

wherein R represents $C_7H_{15}$ and R' represents $C_6H_{13}$, $C_8H_{17}$, $C_{10}H_{21}$ or $C_{12}H_{25}$.

* * * * *